(12) United States Patent
Zhao et al.

(10) Patent No.: US 10,143,425 B1
(45) Date of Patent: Dec. 4, 2018

(54) METHODS OF DATA ACQUISITION QUALITY AND DATA FUSION FOR PERSONAL PORTABLE WIRELESS VITAL SIGNS SCANNER

(71) Applicant: SCANADU INCORPORATED, Moffett Field, CA (US)

(72) Inventors: Wenyi Zhao, Mountain View, CA (US); Brandon Dennis Woolsey, San Jose, CA (US); Walter De Brouwer, Los Altos, CA (US); Eron Anthony Villarreal, San Jose, CA (US); Whitney Morgan McGowan, San Jose, CA (US); Martin Zizi, Enines (BE)

(73) Assignee: Scanadu Incorporated, Sunnyvale, CA (US)

( * ) Notice: Subject to any disclaimer, the term of this patent is extended or adjusted under 35 U.S.C. 154(b) by 239 days.

(21) Appl. No.: 14/292,820

(22) Filed: May 30, 2014

Related U.S. Application Data

(60) Provisional application No. 61/875,681, filed on Sep. 9, 2013, provisional application No. 61/924,230, filed on Jan. 6, 2014.

(51) Int. Cl.
*A61B 5/00* (2006.01)
*A61B 5/0205* (2006.01)
*A61B 5/0402* (2006.01)
*A61B 5/1455* (2006.01)
*A61B 5/11* (2006.01)

(52) U.S. Cl.
CPC ........ *A61B 5/7221* (2013.01); *A61B 5/02055* (2013.01); *A61B 5/0402* (2013.01); *A61B 5/11* (2013.01); *A61B 5/14551* (2013.01); *A61B 5/742* (2013.01)

(58) Field of Classification Search
CPC .......................... A61B 1/00172; A61B 5/0002
See application file for complete search history.

(56) References Cited

U.S. PATENT DOCUMENTS

| 6,261,238 | B1* | 7/2001 | Gavriely | A61B 5/087 600/532 |
| 2005/0137653 | A1* | 6/2005 | Friedman | A61B 5/0002 607/60 |

(Continued)

*Primary Examiner* — Amanda Hulbert
*Assistant Examiner* — Natasha Patel
(74) *Attorney, Agent, or Firm* — Alford Law Group, Inc.; Tobi Clinton

(57) ABSTRACT

In one embodiment of the invention, an interactive vital signs scanning method is disclosed including concurrently scanning for a plurality of vital signs with a portable vital signs scanner; detecting movement of the portable vital signs scanner during the scanning for the plurality of vital signs; and determining a measure of quality of the scanning for the plurality of vital signs with the portable vital signs scanner. In another embodiment, a method of improving the quality of vital signs data is disclosed including concurrently sensing data from a plurality of vital signs sensors over a period of time with a portable vital signs scanner; determining a plurality of vital sign values for a respective plurality of vital signs in response to the sensed data from the plurality of vital signs sensors over the period of time; and fusing at least two vital sign values of the plurality of vital sign values for the respective plurality of vital signs.

34 Claims, 27 Drawing Sheets

(56) References Cited

U.S. PATENT DOCUMENTS

| | | | |
|---|---|---|---|
| 2007/0142715 A1* | 6/2007 | Banet | A61B 5/0006 600/301 |
| 2007/0219059 A1* | 9/2007 | Schwartz | A61B 5/0205 482/8 |
| 2008/0300504 A1* | 12/2008 | Lefkov | A61B 5/053 600/547 |
| 2009/0275805 A1* | 11/2009 | Lane | A61B 5/01 600/300 |
| 2011/0066051 A1* | 3/2011 | Moon | A61B 5/0002 600/509 |
| 2012/0029310 A1* | 2/2012 | Paquet | A61B 5/0008 600/301 |
| 2013/0217979 A1* | 8/2013 | Blackadar | A61B 5/0205 600/301 |

* cited by examiner

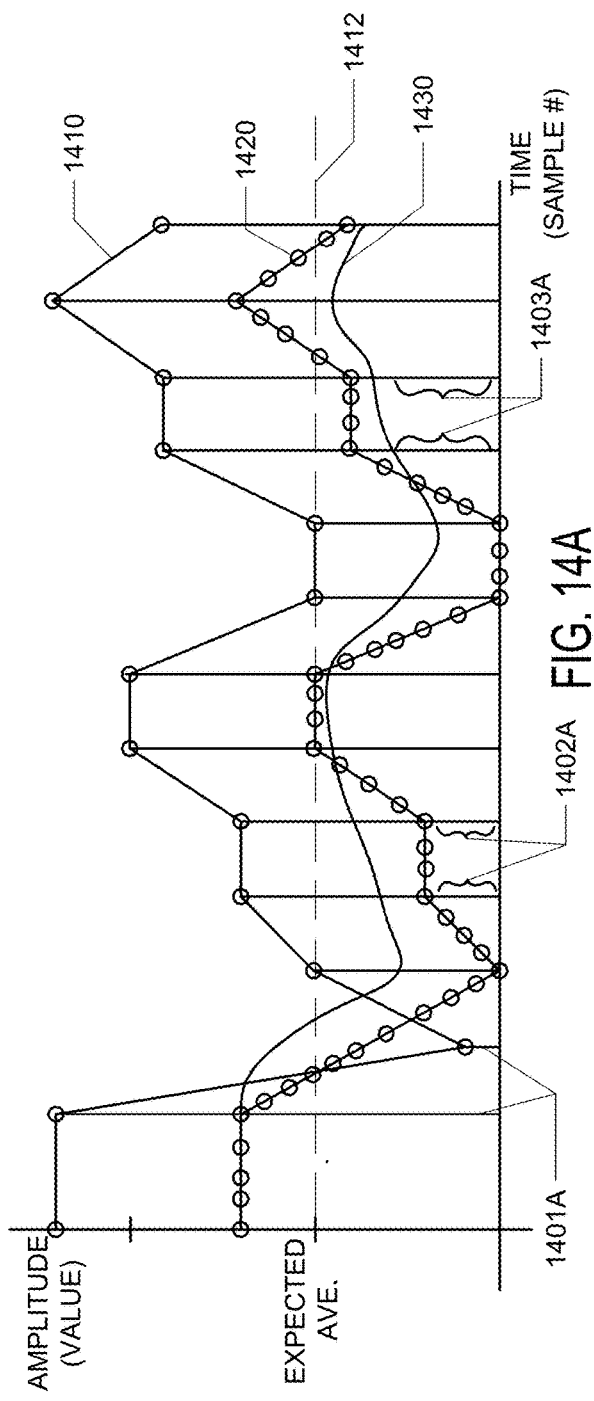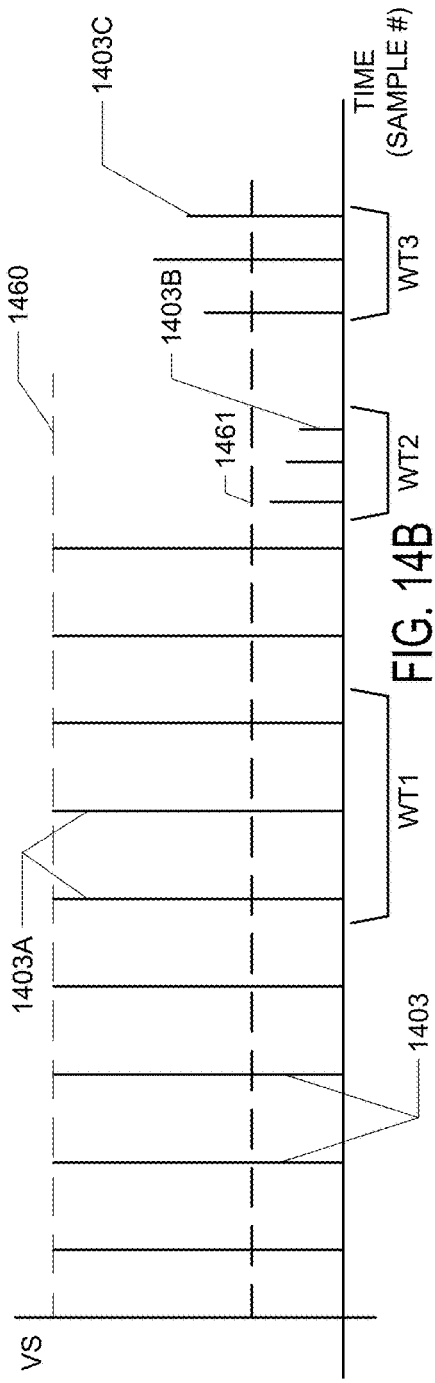

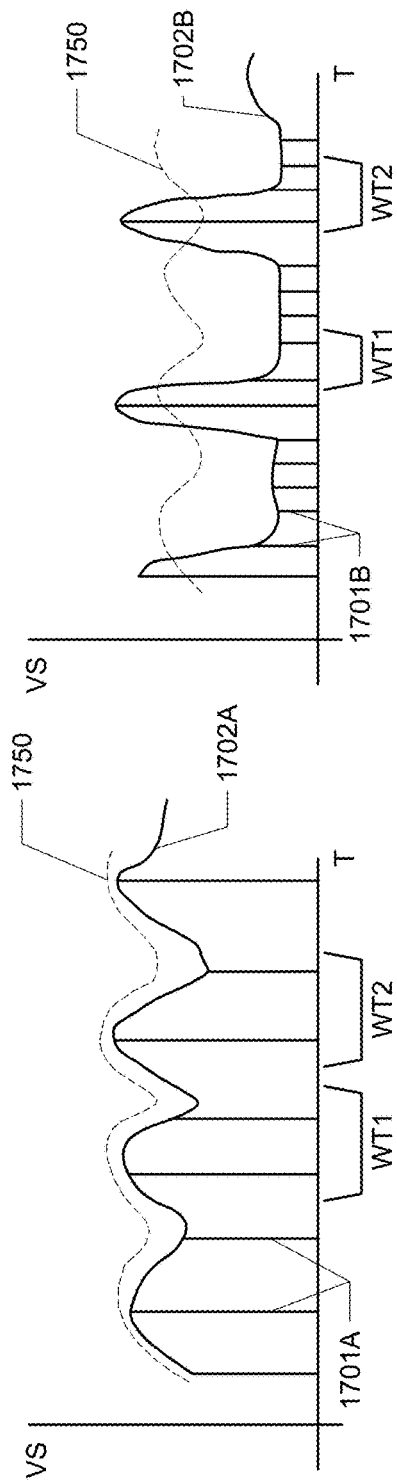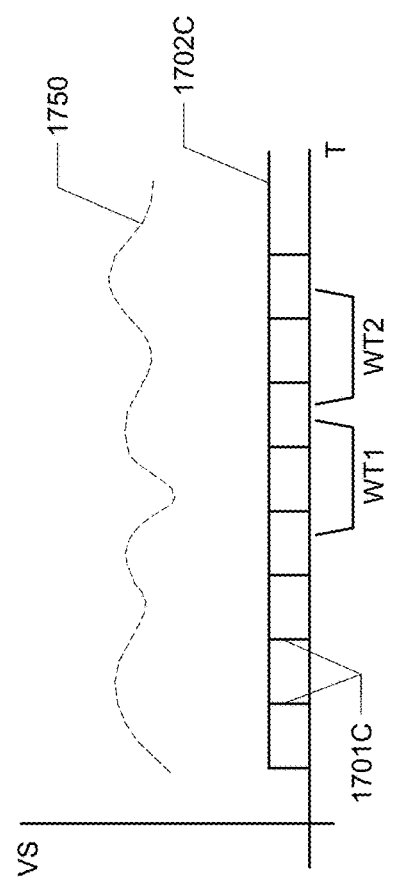

METHODS OF DATA ACQUISITION QUALITY AND DATA FUSION FOR PERSONAL PORTABLE WIRELESS VITAL SIGNS SCANNER

CROSS REFERENCE TO RELATED APPLICATIONS

This non-provisional patent application claims priority to U.S. provisional patent application No. 61/875,681; entitled SYSTEMS, METHODS, AND APPARATUS FOR PERSONAL PORTABLE WIRELESS VITAL SIGNS SCANNER filed by inventors Wenyi Zhao et al., on Sep. 9, 2013; and U.S. provisional patent application No. 61/924,230; entitled DATA ACQUISITION QUALITY AND DATA FUSION FOR PERSONAL PORTABLE WIRELESS VITAL SIGNS SCANNER filed by inventors Wenyi Zhao et al., on Jan. 6, 2014; both of which are incorporated herein by reference.

FIELD OF THE INVENTION

This invention generally relates to vital signs scanning with a portable device having multiple integrated vital sign sensors.

BACKGROUND OF THE INVENTION

Healthcare is a key element of any modern society. Over the years, it has brought people the benefit of the latest technological breakthroughs that are safeguarded by well-established regulatory process. The practice of medical practitioners has also evolved into highly specialized fields and subfields. One of the most important aspects of medicine is preventive care. A significant portion of healthcare costs could be reduced if ailments are diagnosed early. Yet many of the tools to diagnose early symptoms are unavailable to the average consumer.

Vital signs of one's body, such as temperature for example, form the base map of ones health. Fluctuations in our vital signs may be predictive of undiagnosed ailments. It's important to have easy access to their vital signs as frequently as needed. Yet the average consumer has no easy method of obtaining many of their vital signs without visiting a hospital or clinic. One of the easiest-to-measure vital signs is body temperature. Consumers are able to measure body temperature at home with an inexpensive home thermometer. However the average consumer still does not have easy access to devices for measuring the other important vital signs of ones body, such as blood oxygenation or blood pressure for example. The technology is available to measure the important vital signs, but typically limited to clinics and hospitals.

Consumers do not have a way to measure all of their important vital signs at home. Consumers cannot visit their physician five or more times a day to constantly monitor their vital signs. This has put the average consumer with a medical condition into a difficult situation, where they do not know what to do with their condition when they need vital signs information while at home or traveling. The few options the average consumer has with an unknown medical condition include staying calm and doing nothing, calling their primary care providers (PCP) to get an appointment, or visiting an emergency room (ER) and waiting for hours.

Even if the consumer opted to do one of the latter options, the PCP or ER may not be able to provide personalized advice without knowing the specifics about their patients. The physician may have some idea about one's health condition based on an annual exam but the data may be outdated and useless with a current medical condition.

As a result, the average consumer may not receive the best medical care due to the lack of information. And together, with PCPs, we also manage to add more cost to the healthcare system that is already very expensive as people live longer.

The problem, simply put, is that consumer access to basic health care is rather limited. It is desirable to improve the quality and access to basic health care for average consumers.

SUMMARY OF THE INVENTION

The embodiments of the invention are best summarized by the claims below. Insofar as a summary is required, one embodiment of the invention can be described as a portable vital signs scanner with an interactive user interface to improve scan data quality.

This summary is provided to efficiently present the general concept of one or more embodiments of the invention and should not be interpreted as limiting the scope of the claims.

BRIEF DESCRIPTION OF THE DRAWINGS

These and other features, aspects, and advantages of the present disclosure will now be described with reference to the drawings of embodiments, which embodiments are intended to illustrate and not to limit the disclosure, as are described in varying degrees of detail below.

FIG. 14A illustrates exemplary graphs of forming an envelope curve of vital signs data.

FIG. 14B illustrates an exemplary graph of determining quality of vital signs data with a pair of threshold levels.

FIGS. 17A-17C illustrates exemplary graphs to confirm the quality of vital signs data with an expected curve.

DETAILED DESCRIPTION

Figure 1A:
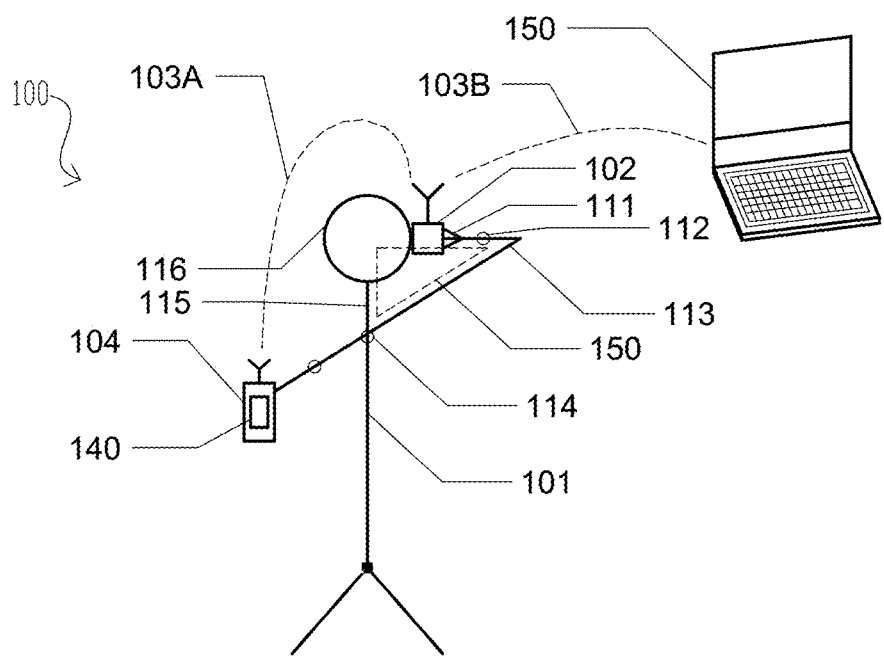
FIG. 1A is a diagram illustrating an exemplary vital signs scanning system with the scanner held at the forehead/temple.

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more particular embodiments may also be included in combination with another embodiment even though not expressly shown and described in that specific combination.

For purpose of efficiency, reference numbers may be repeated between the figures where they are intended to represent similar features between otherwise varied embodiments, though those features may also incorporate certain differences between embodiments if and to the extent specified as such or otherwise apparent to one of ordinary skill (such as differences clearly shown between them in the respective figures).

It is desirable for consumers to take greater control of their own basic health and work with their primary care providers (PCPs) to provide personalized healthcare. Some embodiments of the invention provide a consumer device that is small enough to be carried in a pocket or purse with which effortless vital signs scans can be performed, anytime, anywhere. The consumer device, referred to as a vital signs scanner, can transfer the vital signs results to a portable wireless multifunction device, such as a smartphone, for storage and display to a user over time to illustrate health trends. The vital signs scanner allows consumers to take greater control of their own basic health and work with PCPs to provide personalized healthcare.

The vital signs scanner allows users to efficiently measure multiple vital signs simultaneously. Vital signs scanning with the vital signs scanner is quick and easy and very convenient in that it can simultaneously capture a plurality of vita signs data with one scanning session (one or two vital signs scans) at a given time and date. The vital signs data is transferred to a user's own portable multifunction touch screen device, e.g. a smart phone. The portable multifunction device, with the assistance of vital signs scanning software, displays the scanning results in an intuitive user interface that is simple to understand.

The vital signs scanning device provides a method of vital signs scanning to help solve the missing information link so a user can take control of managing his/her own health. In addition to providing vital signs scanning, the vital signs scanner and system also stores the users vital signs measurements and trends over time of a day and date. The vital signs scanner and system provides easy access (almost anywhere at anytime) to important vital signs measurements such as blood oxygenation, blood pressure, heart rate, etc. The vital signs scanner and system can help share up-to-date vital signs data with a user's PCP for better diagnosis of medical conditions. Perhaps even more importantly, sharing of history and trends of vital signs data before and after an ailment with the user's PCP can provide clues to its cause and not just indicate the symptoms.

The personal wireless vital signs scanner combines aesthetic design with functionality. The personal wireless vital signs scanner is light weight and easily fits into one hand (e.g., handheld). The personal wireless vital signs scanner can be held and operated with just two fingers of one hand. The user's other hand is free to hold a smartphone with a vital signs scanning application running to control the vital signs scanning process and view the scanning results. Vital signs data of a users body can change at different times of each day. The personal wireless vital signs scanner is so small, light, and esthetically pleasing that a user may desire to take it with them to perform a plurality of vital signs scans at different times throughout his/her day over a plurality of days.

The vital signs scanner may fuse data together from various data sources, referred to as a fusion process, in different ways in order to increase measurement accuracy, increase quality control of data acquisition, and/or provide additional information to a user. The data that may be fused together includes concurrent information or data streams originating from different sensors in the vital signs scanner; different information in a data stream originating from the same sensor; information in an internal data stream from a sensor in the vital signs scanner and external generated data, such as data originating from a user's input, biometrics or one or more databases; or any combination thereof. To facilitate the fusion process, the data streams may be split, independently processed in parallel, and recombined or compared against each other depending on the needs for the information. For example, a fusion process may involve comparing scan data in independent data streams from a plurality of sensors to cross-validate the quality of their scan data.

A portable vital signs scanner and system may prove to be useful for healthcare professionals as well. For example, patients could scan for their own vital signs themselves in a busy hospital, clinic or doctors office, rather than wait in long lines just to get a simple checkup before seeing the doctor. The patients scans are then uploaded to a server at the hospital, clinic, or office. With these self-obtained vital signs scans of patients being uploaded to a server, medical assistants and nurses, ordinarily checking for vital signs, can better spend their time curing the ailments of the patients.

The self-obtained vital signs scans of patients may also serve to triage the patients that are waiting for medical care. For example, a self-obtained vital signs scan of a patient indicating an elevated or irregular heart rate may signal hospital staff to attend to this patient immediately or at least a higher priority in a queue of patients. In this manner, the self-obtained vital signs scans of patients provide a clinic staff with a sense of the severity of the condition of patients waiting and can make appropriate schedule priority adjustments, if needed.

Referring now to FIG. 1A, a diagram illustrating a vital signs scanning system 100 is shown. The scanning system 100 includes a portable wireless vital signs scanner 102 and a portable wireless multifunction device 104 in wireless communication with each other over a wireless communication channel 103A. The vital signs scanner 102 includes a plurality of sensors designed to read vital signs from a user's body 101. An instance or snap shot of vital signs, such as temperature, heart rate, blood oxygenation (SpO2), electrocardiogram (ECG), and possibly stress levels, all synchronously measured, can be reported to the device 104 by the scanner 102 in less than a minute. Exemplary methods and algorithms for determining one or more of these vital signs from the sensor data are described in International Application No. PCT/US2013/061046, filed by Scanadu Corporation on 19 Oct. 2012, having international publication no. WO 2013/066642, entitled AUTOMATED PERSONAL MEDICAL DIAGNOSTIC SYSTEM, METHOD, AND ARRANGEMENT, claiming priority to U.S. Patent No. 61/549,134 filed on 19 Oct. 2011, and is hereby incorporated by reference.

The algorithms and processes disclosed in International Application No. PCT/US2013/061046 are based upon one or more of the following references (all of which are incorporated herein in their entirety): *Pulse transit time: an appraisal of potential clinical applications*, Thorax 1999; 54:452-457 [doi:10.1136/thx.54.5.452] [http://thorax.bmj.com/content154/5/452.full]; U.S. Pat. No. 6,723,054; U.S. Pat. No. 6,527,728; U.S. Publication No. 2007/0276632; and U.S. Publication No. 2003/0199771; Severinghaus, John W., Honda Yoshiyuki (April 1987), "History of Blood Gas Analysis. VII. Pulse Oximetry", Journal of Clinical Monitoring # (2): 135-138; Millikan G. A. (1942). "The oximeter: an instrument for measuring continuously oxygen-saturation of arterial blood in man", Rev. Sci. Instrum 13 (10): 434-44 [doi:10.1063/1.1769941]; U.S. Pat. No. 6,385,471; U.S. Pat. No. 5,934,277; U.S. Pat. No. 5,503,148; U.S. Pat. No. 5,351,685; U.S. Pat. No. 5,259,381; U.S. Pat. No. 4,883,353; U.S. Pat. No. 4,824,242; U.S. Pat. No. 4,807,631; U.S. Pat. No. 4,796,636; U.S. Pat. No. 4,714,080; U.S. Pat. No. 4,623,248; and U.S. Pat. No. 4,266,554.

Integration of multiple sensors and scan quality algorithms make it possible to monitor the quality of the scanning process and then provide feedback to the user to control the interactive scanning process and provide a good user experience in the vital signs scanning process. As used herein, user feedback means feedback provided by the scanner and/or portable wireless device through the user interface or otherwise to the user, including any scan quality feedback that is provided to the user. User input means any input that a user provides to the scanner and/or portable wireless device.

The wireless vital signs scanner 102 may perform vital signs scans and display the results in under a minute. Generally scans may be completed in approximately ten seconds. The length of a scanning session may depend on the user's ability to correctly utilize the scanner 102. For example, if the user moves too much during the scanning session, the session will last longer as the device 104 prompts the user to remain still.

Different types of scans may also take different lengths of time. For example, in a standard ten second head scan where the scanner is held against a user's forehead or temple (forehead/temple), temperature, SpO2, ECG, heart rate, and blood pressure may be measured. For a thirty (30) second extended head scan, vital signs such as blood pressure and heart rate variability (related to emotional stress) may be captured. For a thirty second chest scan from a user's chest, respiration rate and body sounds may be measured or collected. In any case, the scanning sessions are still short and convenient.

Short scanning sessions have several advantages. A short scanning session allows a user to take a quick break from their daily activities to perform a scan anywhere and at any time. The ease and rapidness of performing a vital signs scan will encourage users to perform the scan multiple times a day, providing more complete and accurate trending data. The invention provides a consumer oriented scanner that a user can use anytime anywhere to obtain multiple vital sign measurements in seconds.

Short scanning sessions also conserve power. With ten second scans, the scanner may last approximately one week under normal usage with one full battery charge. If the power is on for a total of about 30 seconds for each scan, then total power-on time for each day is less than one hour with 100 scans per day. In this case, the scanner 102 may operate for a week at a time between battery recharging sessions.

Scanner 102 is an elegant consumer device that is portable. Unlike other vital sign monitors, scanner 102 does not need to be worn. Scanner 102 is perhaps the smallest consumer device that can measure multiple vital signs simultaneously. Measuring approximately 60 mm in diameter and 18 mm high, the scanner 102 can be easily places in a pocket or purse for use at any time convenient to the user. At any time the user has a moment to spare, the scanner 102 may be used to obtain multiple vital sign measurements by simply finger-holding it against the user's forehead/temple, and/or chest.

Using a multifunction device 104 to display the vital signs scanning results allows the scanner 102 to maintain a compact size and minimalist form. Multifunction device 104 may be any portable wireless multifunction device such as a smartphone, tablet PC, or the so called smart watches. Generally these devices are pre-owned and already available to the average consumer, so utilizing the display capabilities of multifunction device 104 does not detract from the portability of the invention. The ubiquity of smartphones also means that the average consumer does not need to pay more for a dedicated display device. Combining the vital signs scanner 102 with, a smartphone that a user already has, allows one to take control and greater responsibility for his/her health without sacrificing valuable time and money.

To display the vital signs scanning results, the portable wireless digital device 104 executes a vital signs scanning software application 140. The instructions of the vital signs scanning software application 140 are executable with the operating system, (e.g., Android and iOS), of the multifunction device 104. Once the software application is active, the user may power up the vital signs scanner 102. Upon power up, the vital signs scanner 102 is paired with the portable wireless digital device 104 to form the communication channel 103A between them. Accordingly, each of the scanner 102 and multifunction device 104 has a compatible wireless radio to form a compatible wireless communication channel. In one embodiment, the communication channel 103A is a Bluetooth version 4, a smart low energy (LE) supported channel that each wireless radio supports. The vital signs scanner 102 sends the vital sign information wirelessly to the portable wireless multifunction scanner 102 over the wireless communication channel 103A for storage and further analysis.

With the communication channel 103A available, the vital signs scanner 102 is pressed against a user's forehead/temple. The forehead/temple is identified as the single place with enough blood vessels and thin skin so that temperature, pulse oximetry and ECG can be obtained in sync and time-stamped. A scanning button is pressed on the user interface of the application 140 of the portable wireless multifunction device 104 to start the scanner 102 scanning for vital signs information of the user. After scanning for approximately 10 seconds or less, the vital signs scanner 102 sends the vital sign information wirelessly to the portable wireless multifunction device 102. The multifunction device 104 may display the results of the scan on a touchscreen display.

The vital signs scanner 102 is used periodically to scan for vital signs each day. Statistical information regarding a plurality of scans each day over a plurality of days can be generated and displayed on the touchscreen display device of the device 140. The vital signs scanning software application 140 informs a user of how those vital sign measurements may change during times of a day and over a plurality of days.

An important aspect of the invention is the quality of the scanning results. To optimize the scanning session results, the scanner 102 is designed to be easy to use to minimize user error. Similarly, the scanning software application is intuitive and easy to use. With minimal instruction, an average user can generate medical grade vital signs scans within minutes of using the invention for the first time.

To further optimize scanning results, scan quality algorithm monitor the vita signs scanning process and provides feedback (visual and/or audible) to the user through the multifunction device 104, and/or alternatively an optional sound generator (see audible sound generator 847 in FIGS. 8A-8B) in the scanner 102. The user feedback may help the user to perform a better vital signs scan with the wireless vital signs scanner and acquire good quality vital signs measurements.

Integration of multiple sensors allows for synergistic accuracy of vital signs scans. For example, integration of an accelerometer enables motion detection that is often associated with poor signals of pulse oximetry and ECG. In another example, abnormal signals of both pulse oximetry and ECG suggest the device is not held against the body properly. This can be further confirmed by comparing the surface temperature and ambient temperature of the sensor when not in touch with the user.

Quality checking of individual vital sign measurements is based on fusion of data from multiple differing sensors, including a motion sensor, such as an accelerometer. Signal quality may be checked based on dynamic range detection and thresholding, for example. To make the process more robust, known signal processing techniques, such as envelope detection, can be applied to the raw signals from the sensors as a preprocessing or screening step. Quality checking of raw sensor signals from the sensors makes sensor data fusion more robust by rejecting bad signals. Thus, fusing results of multiple sensors can provide better individual measurements of each vital sign.

The intuitive scanning user interface (UI) is designed, in combination with scan quality algorithms and the device's self-diagnostic capability, to help users to finish a vital signs scan successfully. There is the quality indicator from the quality algorithm, the progress bar, and texts that provides feedback to the user to ensure a successful scanning session. For example, suggestions to "hold still" or "hold device to your forehead/temple" may prompt the user to correct his/her poor scanning behavior.

The scanning system 100 is user friendly so that it can be used multiple times during the day to obtain data about a user's body 101. One person or one family can exclusively use the scanning system 100 and scanner 102 at home as a personal vital signs scanner. In this manner, a measure of one's personal health and medical data can be obtained right at home with the scanning system 100 without seeing a doctor or being admitted to a hospital. Each scan only lasts approximately ten to thirty seconds and obtains multiple vital sings measurements so users can take the scan repeatedly throughout the day without being inconvenienced.

The scanning system 100 can be used to personally analyze and track one's own vital signs to see various trends over time. Accordingly, the vital signs data can be accumulated over a plurality of days and a plurality of scans at various times each day, then stored in non-volatile manner with the device 104 so the data does not get lost. The vital signs data can also be backed up to a computer, a storage device, or storage server so it is not lost if the device 104 is lost or stolen. The storage server having greater storage may also be used to accumulate ones user data over a plurality of years when the device 104 is limited by its built-in storage capacity.

In operation, the vital signs scanning system 100 forms an electrical circuit 150 with the user's body 101. The circuit 150 is formed between first and second electrodes of the portable wireless vital signs scanner 102. From a first electrode of the scanner 102, the circuit 150 is made with the fingers 111, the hand 112, the arm 113, the chest 114, the neck 115, and the head 116 of the user's body 101 to a front electrode. Preferably, the portable wireless vital signs scanner 102 forms an electrical connection to the forehead/temple portion of the head 116 of a user's body 101. Fingers 111 not only serve to hold the scanner 102, but also as one contact point for one-lead ECG (the other one-lead ECG contact point is forehead/temple). Preferably the thumb finger 111 in one embodiment and the index finger in another embodiment forms an electrical connection with the portable wireless vital signs scanner 102.

The vital signs scanning system 100 may optionally include a personal computer 150 in wireless communication with the portable wireless vital signs scanner 102 over an alternate or additional wireless communication channel 103B.

Figure 1B:
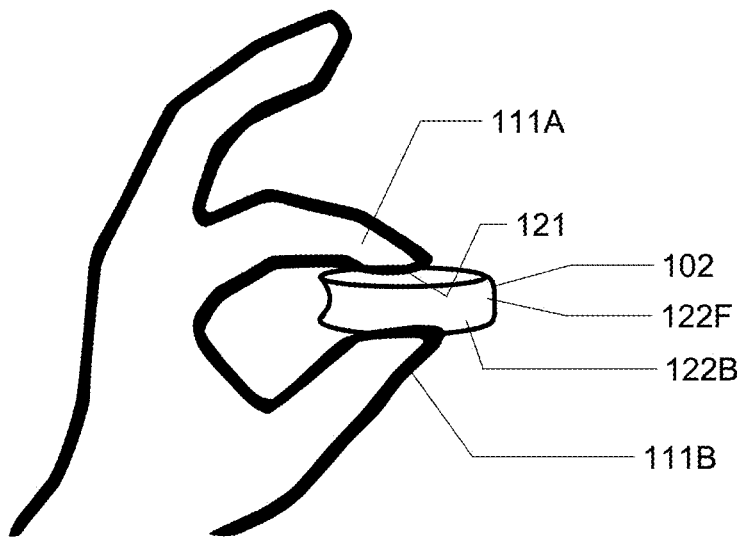
FIG. 1B is a perspective view of a user squeezing the exemplary vital signs scanner.

Referring now to FIG. 1B, a perspective view of a user's fingers 111A-111B squeezing the vital signs scanner 102 is shown. The vital signs scanner 102 is squeezed between the user's fingers to form at least one electrical connection. The front side sensors and a front electrode in the vital signs scanner 102 are then pressed against the user's forehead/temple to form an addition electrical connection. The small size 60 mm×60 mm×18 mm allows the scanner 102 to be held by just two fingers of one hand. At a weight of approximately 60 g (e.g., less than one pound), the scanner 102 may be used by just about any person, from a child to the very elderly. Finger-held form-factor, ten to thirty seconds per scan, scan quality algorithm with feedback and an intuitive scanning user interface on a personal portable multifunction device, all help make vital signs scanning fast and easy while producing quality results.

Preferably, the scanner 102 is held between the thumb 111B and forefinger 111A of the user's left hand. The forefinger 111A may also rest over a sensor 121 and forms an electrical connection to an electrode around the sensor in one embodiment. In another embodiment, the thumb finger 111B makes contact with a bottom electrode 122B. The thumb of the left hand couples to the bottom electrical contact (electrode) on the bottom-housing portion of the scanner.

The forefinger makes contact with a rectangular glass plate over an oximeter sensor 121 in one embodiment. In another embodiment, the oximeter sensor 121 is moved to the front side of the vital signs scanner 102 so that extraneous light is less likely to interfere with the its readings.

A front side electrode 122F makes contact with the user's forehead or temple (forehead/temple), when it is pressed up against his/her head. An infrared (IR) thermometer sensor is combined with the front side electrode 122F. The IR thermometer sensor makes temperature readings at the user's forehead/temple. An oximeter sensor may also be located near the front side electrode 122F.

With the thumb finger 111B in contact with the bottom electrode 122B, a circuit may be formed through the finger and the hand of the user and a portion of his body back to the front side electrode 122F in the vital signs scanner 102. Once proper placement of scanner 102 is made, a scan button is selected in the software application 140 of the device 104 to command the scanner to scan the vital signs from the user's body and forward them to multifunction device 104.

Figure 1C:
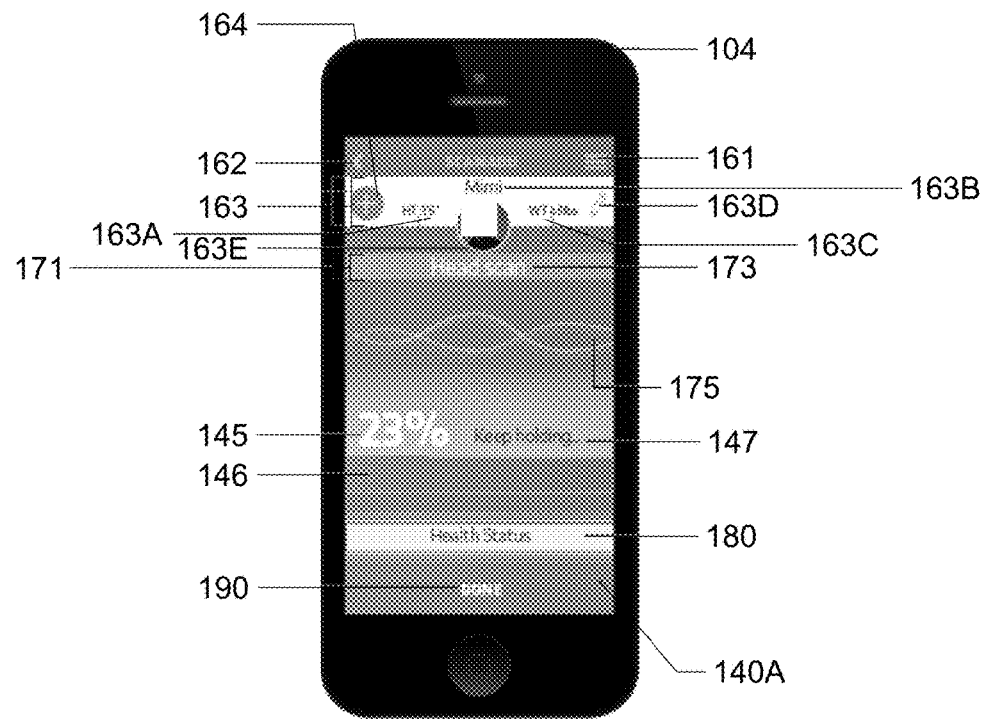
FIG. 1C is a diagram illustrating a portable wireless multifunctional device with a scan screen of a vital signs scanning user interface.

Referring now to FIG. 1C, an exemplary initial scan screen window 140A of the vital signs scanning application 140 is illustrated. The initial window 140A includes an instruction scan messaging 147 with instruction scan message text and optionally an instruction figure to show the user how the vital signs scanner 102 is utilized. As indicated by the instruction scan message, the user is to keep holding the scanner to the user's left temple for the best scan.

The initial window 140A further includes a menu button 161, a back button 162, an edit button 163D, a tag information button 164, a health status button 180, and a done button 190. The tag information button 164 is used to add user information as well as tag scans with the circumstances under which a scan was undertaken, such as after eating or after exercise. The initial window 140A includes a user information bar 163 including information regarding a user's height, user's name 163B, user's weight 163C, and a user's profile picture 163E. In this manner, the user is clear as to whom is logged into the vital signs scanner user interface and for who's body is to be canned. The initial window 140A further includes a scan type indicator 173, indicating a head scan type during a first scanning or a chest scan type during a second scanning period. The initial window 140A further includes a scan quality indicator 175, a scan progress bar 146, and a scan progress percentage indicator 146. The scan quality indicator is one form of quality feedback that may be employed by the scanning system to inform and train the user to acquire better scan data. The initial window 140A further includes a scan type slider 171 to select the type of scan that is to be performed. The menu button 161 can take the user to the next screen or a different screen within the vital signs scanning user interface. The edit button 163D can edit information and select options that are available in the vital signs scanning application 140.

The vital signs scanning application 140 may include an option to enter the user's symptoms by selecting the health status button 180. A photo may also be taken of the medical condition of a user by use of a camera in the device 104 and a photo button. Additionally, a user may add a note to his health status using the device 104 and an add note button.

The status of the scanner 102, such as powered on/off, Bluetooth connection, battery charge status, and/or ready to scan, may also be displayed in one or more of the user interface windows of the vital signs scanning application 140.

The scanner 102 can collect a diverse set of physiological information (e.g., vital signs) during one or two acquisition periods totaling approximately sixty seconds (head scan, extended head scan, and/or chest scan).

Figure 1D:
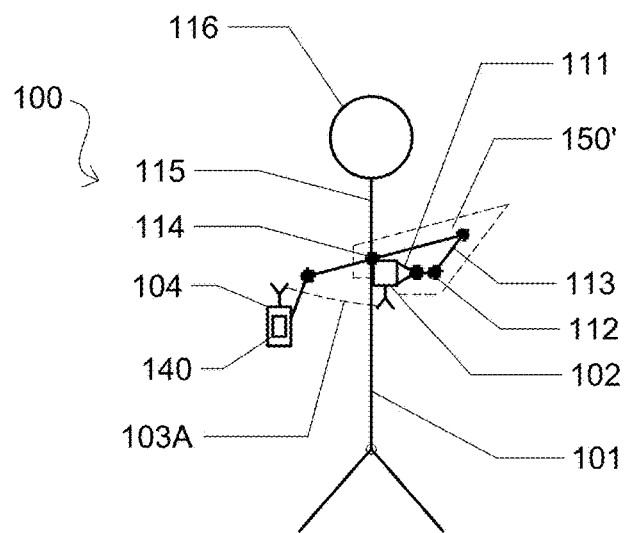
FIG. 1D is another diagram illustrating an exemplary vital signs scanning system with the scanner held at a chest position.

Referring now to FIG. 1D, a diagram of an exemplary vital signs scanning system with the scanner held at the chest position is illustrated. In this embodiment, vital signs are first acquired from a first scanning period (e.g., approximately 10-second scan) at the forehead/temple as shown in FIG. 1A. Vital signs may further be acquired by secondary scans. A longer or extended scan at the forehead/temple with the scanner 102 may be used to capture sensor data as shown in FIG. 1A during a second scanning period. Alternatively or additionally, a subsequent scan conducted near the chest of the user may be performed during another scanning period, such as shown in FIG. 1D.

A secondary extended scan at the forehead/temple may be over a range of time from about thirty seconds up to a minute so that measures of heart rate variability and respiration rate may be obtained. The secondary extended scan at the forehead/temple can also provide for a more robust and accurate measurement of blood pressure. In terms of using the scanner, the primary and secondary scans at the forehead/temple may occur in one single scan (e.g., 10-second or 30-second) or two separate scans (e.g., a first at 10 seconds and then a second at 30 seconds).

The secondary extended scan near the chest, a chest scan, is mainly to capture vital signs of respiration rate and additional physiological information from the captured body sounds. The vital signs scanned at the chest area may also include heart rate variability. Noise may also be captured in the signals captured by the sensors of the scanner that can be used to better extract the desired signal data. The secondary extended scan near the chest may last for a period from thirty seconds to a minute. The vital signs scanning application executed on the multifunction device 104 may prompt the user for one or both scan locations.

The secondary chest scan can be selected by the scan type slider 171 shown in FIG. 1C. A second or third scan may be selected with a finger swipe to perform the second scan or the third scan at the chest of the user. If only the first head scan was desired, a done button 190 may be selected to avoid the secondary scans. This may be because its inconvenient due to timing or to perform against ones chest with the vital signs scanner, such as when it is inconvenient to do so in public.

Figure 1E:
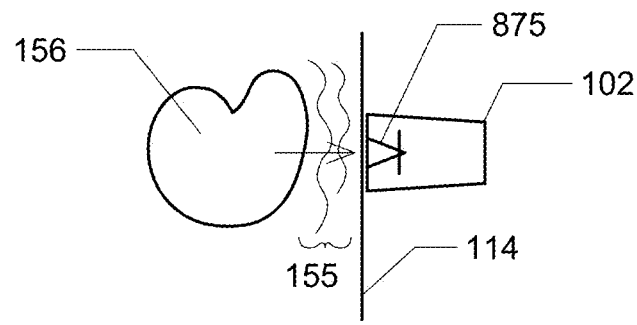
FIGS. 1E-1F are diagrams illustrating how microphones of the exemplary vital signs scanner can capture body sounds, such as from a user's heart or lung.
Figure 1F:
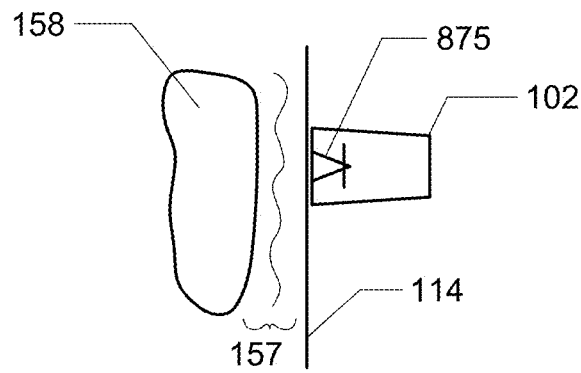

As mentioned herein, a chest scan may be performed with the scanner 102 as shown by FIGS. 1D, 1E, and 1F, for example. In FIG. 1D, a second circuit 150' may be formed with the users body 101 between the electrodes of the scanner 102. The second circuit 150' in this case includes the chest 114, the arm 113, the hand 112, and the finger 111 of the user.

Figure 1G:
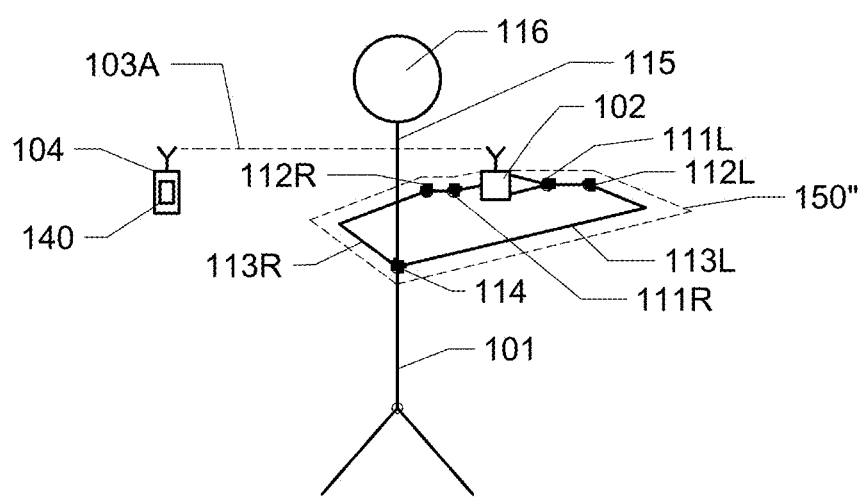
FIG. 1G is another diagram illustrating an exemplary vital signs scanning system with the scanner held in fingers of each hand.

In an alternate embodiment, another circuit 150" may be formed with the users body between the electrodes of the scanner 102 while the device 104 is nearby. This alternate circuit 150" is formed by fingers on different hands coupling to the electrodes of the scanner 102. A left finger 111L may couple to a bottom or top electrode in the scanner 102. A right finger 111R may be coupled to the front electrode of the scanner 102. From a left finger 111L in a left hand 112L of the user, the circuit in the body includes, the left finger 111L, the left hand 112L, the left arm 113L, the chest 114, the right arm 113R, the right hand 112R, and a right finger 111R, such as shown in FIG. 1G, to complete a circuit with the scanner 102.

In either case, the ECG circuitry in the scanner 102 may then obtain further data regarding heart activity of the user that can be combined/fused with the heart activity data of a first scan, to improve the measure of vital signs of heart activity. The vital sign measures of heart activity may then be sent to the device 104 for display to the user on its built-in touchscreen display.

Temperature of the body adjacent the user's chest 114, if reliable, may also be used by the scanner to improve scanning results of temperature. Temperature at the user's finger 111R, if reliable, may also be used by the scanner to improve scanning results of temperature.

With the scanner adjacent the users chest, near or over the heart during the chest scan, clothed or unclothed, an accelerometer (see accelerometer 885 in FIGS. 8A-8B) in the scanner 102 may be used to capture movement of the chest as a measure of respiration rate. The vital signs data from these measures are computed by the processor 840 and then sent to the device 140. With the accelerometer within the scanner 102, data for measuring heartbeat and respiration rhythm can be acquired over clothing, without the user needing to undress. Heartbeat and respiration rhythm based on scan data from the accelerometer has the added advantage of allowing cross-correlation with other data streams from other sensors.

FIGS. 1E and 1F illustrate the use of the microphones 875 in the scanner 102 to capture body sounds around the chest 114, such as heart sounds 155 and lung or breathing sounds 157. These body sounds may be recorded to capture another symptom of a user's medical condition. Body sounds that are captured may also be used to judge the quality of the vital signs scanning process. The recorded body sounds may be stored locally in the memory of the scanner and/or sent to the device 140 for storage with the vital signs data of the same time and date.

Scan data captured by the scanner may provide person-specific biometrics information. Phase spaces (poincare plots) of accelerometric data can provide an element of person-specific biometric data, an identification linked to person specific noise in the acquired signals. Using chaos mathematics and various analytic tools on cross-correlated or uncorrelated data streams from the human body, it is possible to obtain positive identification of any user linked to each person specific noise in the acquired data signals. This noise originates in the numerous minor and major anatomical and functional differences between the various users. The noise being person-specific acts like electronic fingerprints of a user.

Figure 2A:
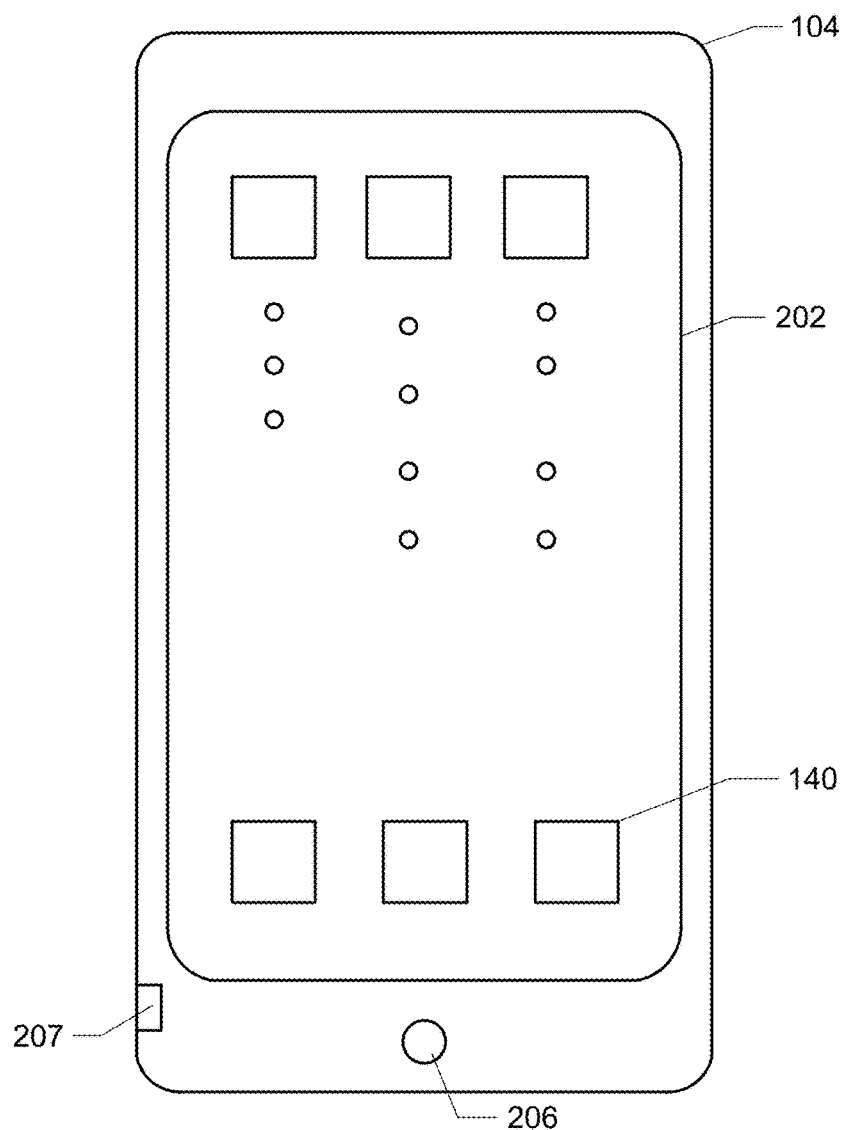
FIG. 2A illustrates an exemplary portable wireless multifunction device to execute the vital signs scanning application.

Referring now to FIG. 2A, a portable wireless multifunction device 104 is illustrated that can execute the vital signs scanning application 140. The portable wireless multifunction device 104 includes a text screen 202, at least one function button 206, and a power button or switch 207. The multifunction device 104 may display a plurality of application icons on the touch screen 202. One of these icons may be the vital signs scanning application software icon 140.

Figure 2B:
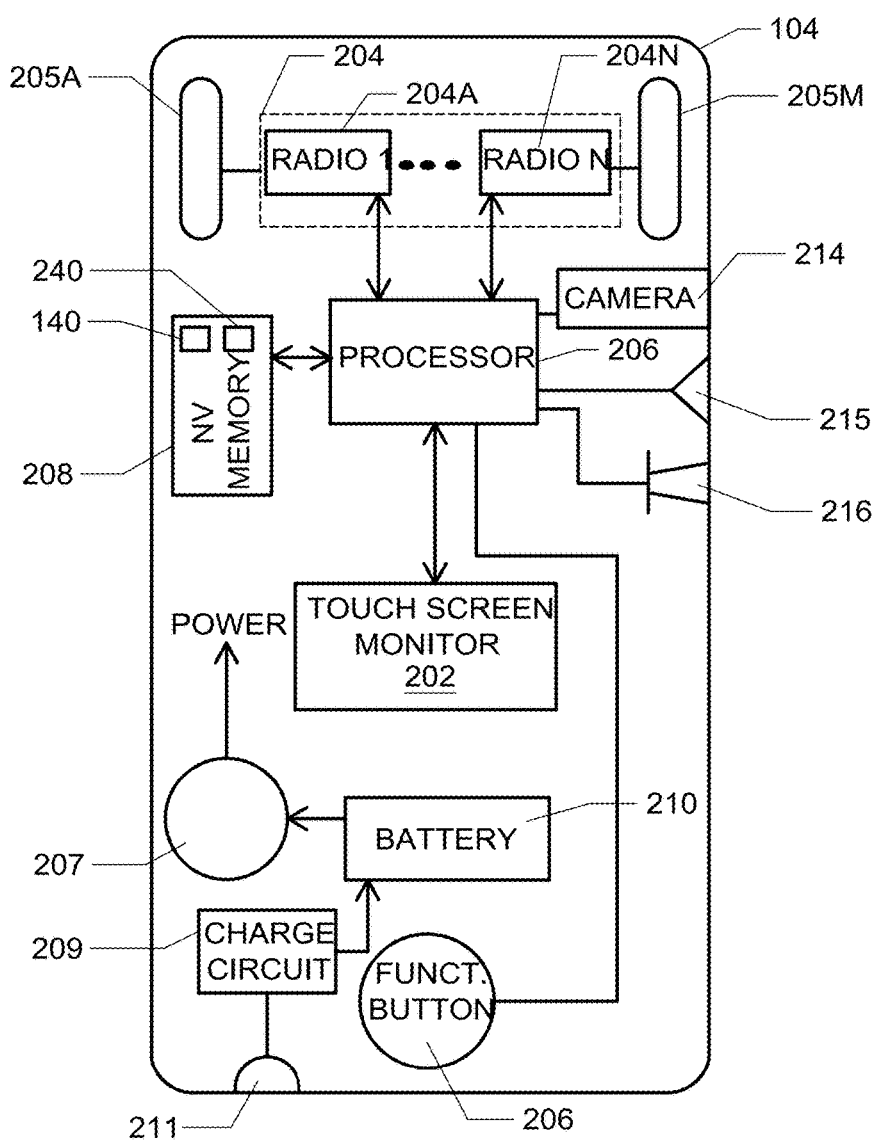
FIG. 2B illustrates a schematic representation of the components of the portable wireless multifunctional device.

Referring now to FIG. 2B, a block diagram of the personal wireless digital device 104 is illustrated. The portable wireless multifunction device 104 may be a smart phone, a tablet computer, a portable music player, or a wireless portable storage device, for example, that include a processor, a touch screen, and a memory from which application software instructions may be executed.

As shown in FIG. 2B, the portable wireless multifunction device 104 includes a touch screen monitor 202, one or more wireless radio transmitters-receivers (wireless radios) 204A-204M coupled to their respective antenna 205A-205M, a processor 206, non-volatile memory 208, at least one function button 206, and a cover button 207 that can switch power on to each electronic circuit within the portable wireless multifunction device 104. At least one of the wireless radios 204A-204M are compatible with the wireless radio in the wireless vital signs scanner 102.

The portable wireless multifunction device 104 may further include a camera 214, a microphone 215, and a speaker 216 coupled to the processor 206 as shown. Furthermore the portable wireless digital device includes a battery 210 coupled to the power button 207. Typically the battery 210 is a rechargeable battery such that an external power source may be coupled thereto via an external power connector 211 and a charge circuit 209.

Non-volatile memory 208 of the personal wireless digital device may store the vital signs scanning application software 140 and data 220 related to the vital signs scan application software. The processor 206 can read and write to the non-volatile memory such that the vital signs scanning application software can provide a user interface to a user via the touch screen display device 202. As discussed previously, the initial vital sign scanning window 140I may be provided as shown in FIG. 1C.

The camera 214 of the portable wireless digital device 104 may take photographs of a user's conditions or symptoms via the photograph entry button 175 of the user interface. The photographs may be stored as part of the data 240 in the non-volatile memory. The microphone 215 in the portable wireless multifunction device 104 may optionally be used to capture body sounds similar to the microphones in the scanner 102, as is shown in FIGS. 1E-1F.

The speaker 216 of the portable wireless digital device 104 may optionally be used to provide audible user feedback to the user of the vital signs scanner 102 to improve the vital signs scan quality as is discussed herein.

Figure 3A:
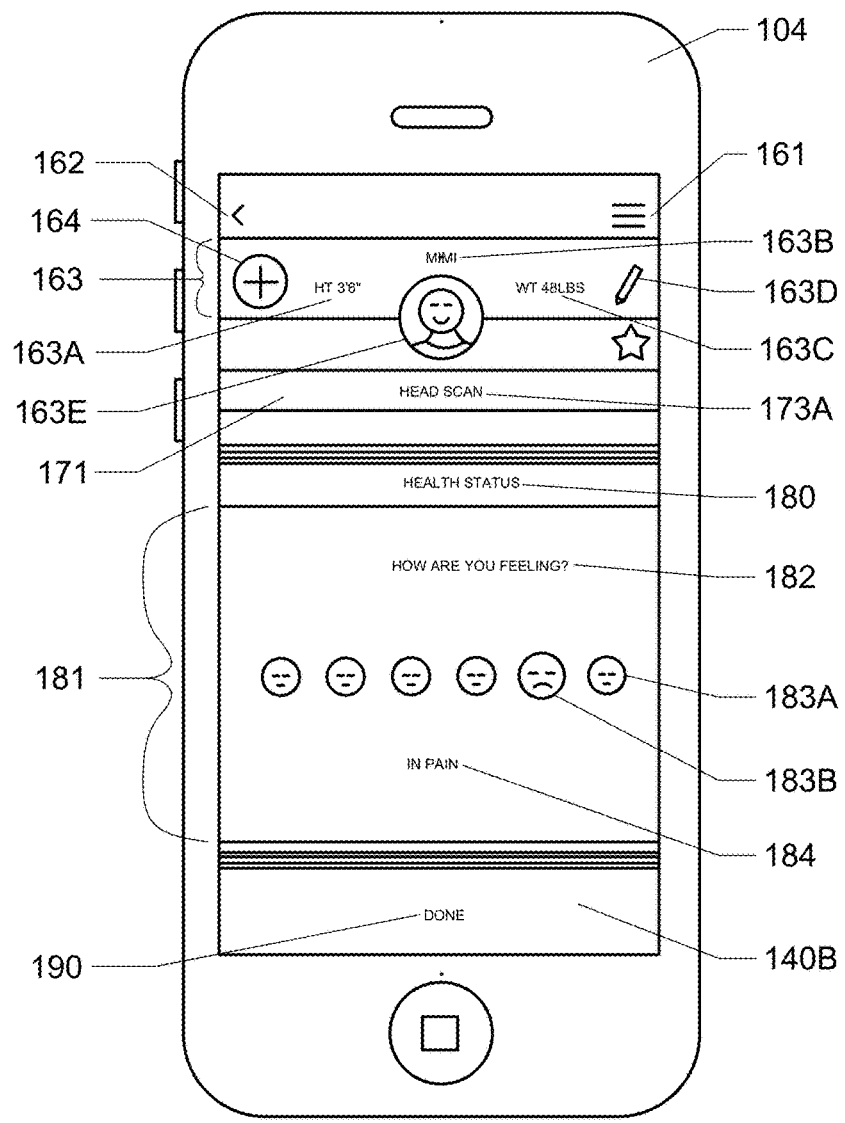
FIG. 3A is an exemplary health status window displayed on the portable wireless multifunctional device by the vital signs scanning user interface (VSUI).

Referring now to FIG. 3A, an exemplary scanning window 140A is shown being displayed by the touch screen display device 202 of the portable wireless multi-function device 104. The scanning application software 140 generates the various images consisting of a scanning progress bar 310, a scanning icon 312, a first vital signs graph 314A, a second vital signs graph 314B, one or more result buttons 320, and one or more status icons 324.

The status icon 324 may be a wireless connection status icon indicating that the portable wireless digital device 104 is connected to the vital signs scanner 102. The button 320 may be a results button to which to switch to another scanning window/screen of a user interface provided by the scanning application software 140. The scanning icon 312 may include the plurality of color bars 312A-312E that randomly vary in color and length to indicate that scanning is occurring. The scanning progress bar 310 illustrates the progress of the scanning session being performed by the portable wireless vital signs scanner 102. In this case data is being sent from the scanner 102 to the portable wireless multifunction device 104.

Briefly referring back to FIG. 1C, the initial window 140A includes a user menu button 161 that may be used to display a users menu on how to operate the vital signs scanner. The initial window 140A may further be changed to a graph window to show plots of prior scan data stored in the device 104. A graph button may be provided to do so or a finger swipe may be used.

The first vital signs can be displayed in graph form over different day granularity such as 1 day, 1 week, 1 month, 3 months, 9 months and 1 year. Graphs may be electrocardiogram (ECG) graphs to illustrate the electrical activity to show the user's heart rate or heart rate variability. The waveforms displayed in the graphs are captured by the scanning process of the portable wireless vital signs scanner 102. A second vital signs graph may be oxygenation graph related to photoelectric plethysmogram (PPG) from the data obtained by the pulse oximeter. The scanner captures a user's blood volume pulse of both oxygenated and deoxygenated blood. From the photoplesmography waveforms (oxygenated and deoxygenated) a user's oxygen saturation can be obtained and displayed in the oxygenation graph.

Referring now to FIG. 3A, a health status window/screen 140B of the user interface software 140 is shown being displayed by the touch screen display device 202 of the device 104. The screen 140B includes a number of similar items illustrated in screen 140A of FIG. 1B and are not repeated here. The health status slider window/screen 140B (it can be slid sideways) includes a health status button 180, a health status window 181. The health status slider window 181 includes a display of a health status question 182 to obtain further information from a user. To respond, the health status slider window 181 includes a plurality of selectable health status response indicators 183A. The user selects one which becomes highlighted over the others, such as health status response selected icon 183B. The health status slider window 181 further includes a health status selected response information 184, such as "In Pain", that is displayed to the user to confirm the selected health status response.

Figure 3B:
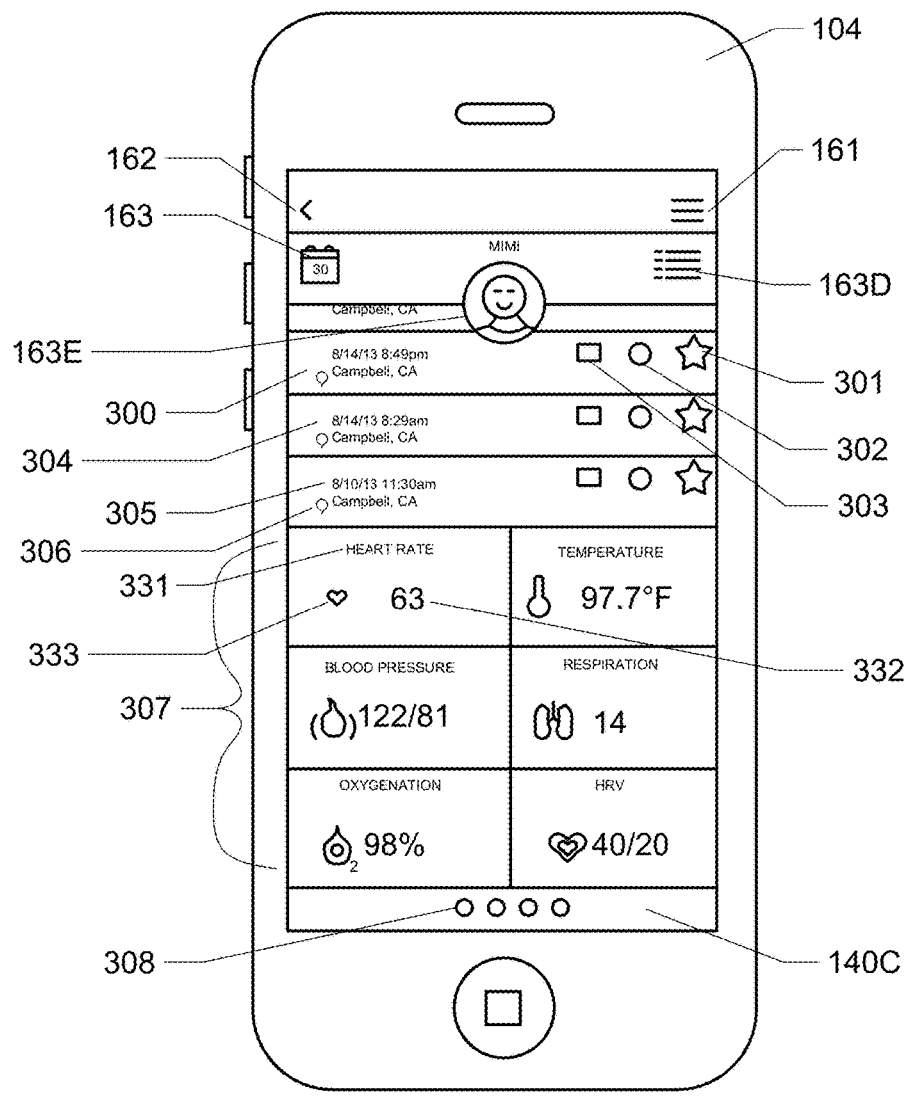
FIG. 3B is an exemplary scan results window displayed on the portable wireless multifunctional device by the vital signs scanning user interface.

Referring now to FIG. 3B, a scanning results window/screen 140C is shown being displayed by the touch screen display device 202 of the device 104. The screen 140C includes a number of similar items illustrated in screen 140A of FIG. 1C and are not repeated here. The exemplary scanning results window 140C may be generated by the user after selecting a results button under the menu button or by one or more sliding finger gestures (e.g., down and/or to the right).

The scanning results window 140C includes a results filter button 163D, and a calendar button 163. The scanning results window 140C displays one or more scanning sessions 300 each including a completed scan type indicator 301, an interpretive message indicator 302, a picture tag indicator 303, a date/time stamp 305, and a location time stamp 306. The scanning session that is selected for display on the device 104 is highlighted by a selected scan indicator 304. The scanning results window 140C further displays a results information slider window 307 and slider number indicators 308.

Figure 3C:
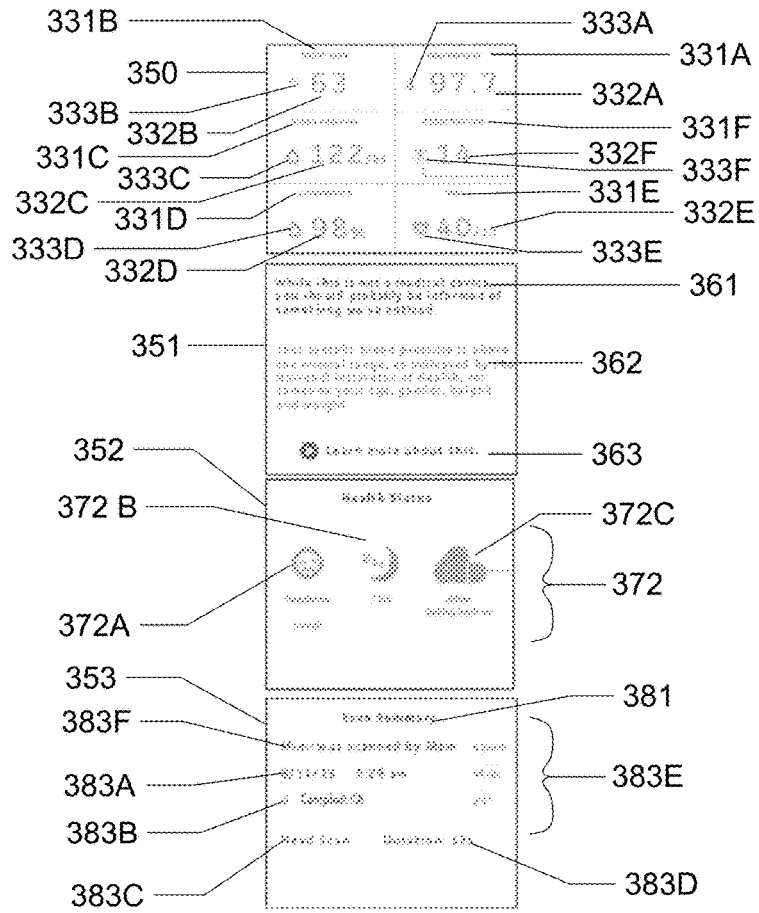
FIG. 3C illustrates exemplary slide windows generated on the portable wireless multifunctional device by the vital signs scanning user interface.

Referring now to FIGS. 3B-3C, the results information slider window 307 of the scanning results window 140C can be slid sideways by a user's finger to display different slides. As shown in FIG. 3C, the different slides or windows displayed in the slider window 307 include a vital sign measurements results slide 350, an interpretive message slide 351, a health status report slide 352, and a scan summary information slide 353.

The vital sign measurements results slide 350 includes a plurality of vital signs icons 333A-333F (collectively 333), a plurality of associated vital signs measurements 332A-332F (collectively 332), and a plurality of associated vital measured labels 331A-331F (collectively 331). The vital measured labels 331 and vital signs measurements 332 indicated in the slide may include heart rate 331B,332B; breathing (respiration) rate 331F,332F; temperature 331A, 332A; blood pressure 331C,332C; heart rate variability (HRV) 331E,332E; and blood oxygenation 331D,332D. The associated vital signs icons 333 may include a heart icon 333B, a breathing (lung) icon 333F, a thermometer icon 333A, a blood pressure icon 333C, a variable heart icon 333E, and an oxygenation icon 333D.

The actual measurements captured during the scanning process are illustrated by the numeric number values of the vital sign measurements 332. For example, the heart rate measurement 332B of sixty-three (63) is shown near the heart icon 333B and the heart rate text label 331B. The numeric values of the vital measurements 332 may be the average measurements captured during the scan that was immediately performed recently or that scan session is selected by the user. The measurements 332 are illustrated near their respective icons 333 and the respective text labels 331 indicating the vital sign that was measured. The results of the scan are typically automatically saved. However, a function button may be required to delete those scan results from the wireless portable multi-function device 104 or alternately a button to upload those results to a storage server.

The interpretive message slide 351 includes a medical information disclaimer 361, a medical interpretive message 362, and a learn more link 363. The medical information disclaimer 361A in the interpretive message slide 351 may be a message such as "while this is not a medical device, you should probably be informed of something we've noticed". The medical interpreter message 362 may be something such as "your systolic blood pressure is above the normal range, as indicated by the National Institutes of Health, for someone of your age, gender, height and weight." The learn more link 363 may include a selectable icon or text to transfer the user to a web browser and a health link where he may learn more about his or her condition indicated by the medical interpreter message 362.

The health status report slide 352 includes health status response buttons 372. Health status response buttons 372 may include a symptoms button 372A to enter health symptoms, such as a headache or a cough for example, when the scan was taken. A medication button 372C may be used to indicate a vital signs scan was performed after taking medication. A sleeping response button 372B may be used to indicate the number of hours of sleep for a night prior to performing the scan.

The scan summary information slide 353 includes a scan summary 381 of a selected scan session. The scan summary may include the time and date stamp 383A, the location 383B of the scan, the type of scan 383C (e.g., head or chest), and the duration 383D of the scan, such as thirteen (13) seconds. The scan summary 381 may further indicate user biometrics 383E such as the gender, age, weight, and height of the user being scanned. The scan summary may further indicate whom 383F performed the scan, such as the user or a family member. In the scan summary example in the scan summary slide 353 shown in FIG. 3C, the user Mimi was scanned by her Mom on Aug. 14, 2013 at 8:29 AM in Campbell, Calif. The scan of Mimi was a head scan having a duration of thirteen (13) seconds. Mimi's user biometrics indicates she is five (5) years old, weighs forty-eight (48) pounds, and a height of three feet, six inches (3', 6").

Figure 3D:
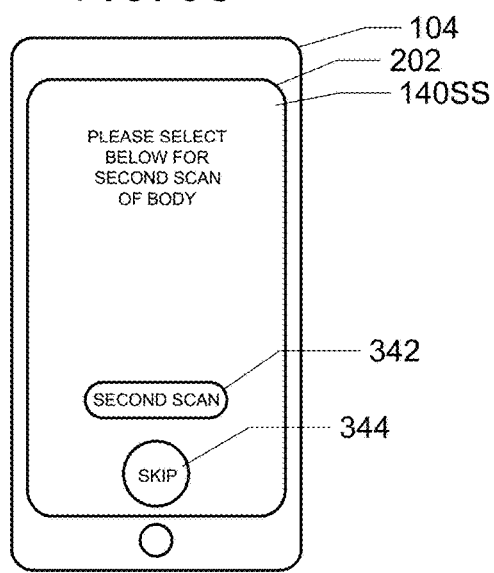
FIG. 3D illustrates an exemplary second scan selection window of the vital signs scanning application on the portable wireless device.

FIG. 3D is an illustration of an exemplary window of the vital signs scanning application on the portable wireless device. In this exemplary window displayed on touch screen 202 of the multifunction device 104, the vital signs scanning application 140 is prompting the user to select a second scan. A second scan may be selected by touching scan virtual button 342 or using a finger gesture on the touch screen. A third scan may also be selected after the second by touching scan virtual button 342 or using a finger gesture on the touch screen. The third scan may be performed at the chest region to measure respiration rate and collect body sounds. The user may desire to skip a secondary scan by touching a skip scan virtual button 344.

Figure 4A:
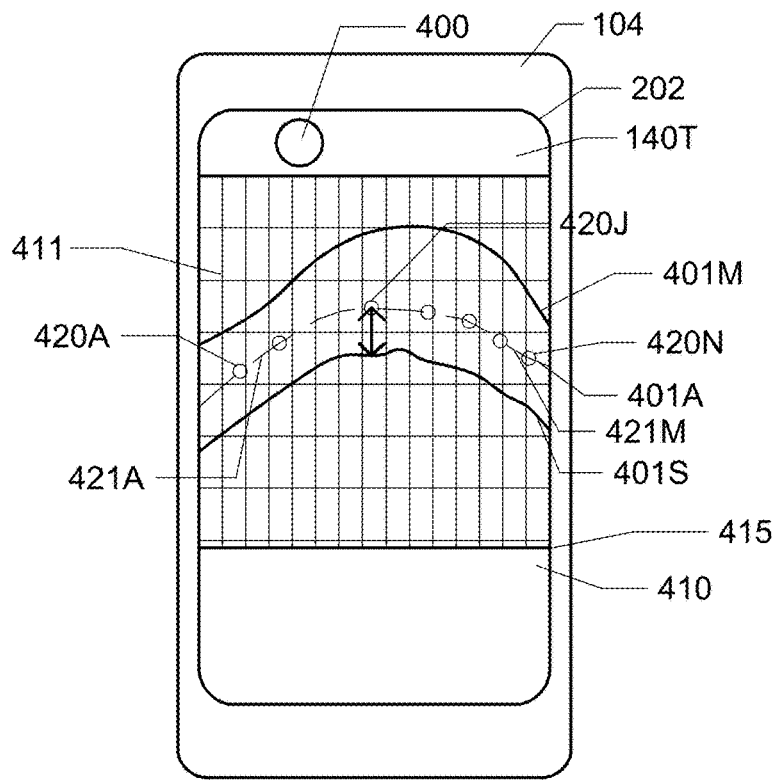
FIGS. 4A-4B illustrate a temperature averaging window generated in a touch screen of the portable wireless multifunction device by the vital signs scanning software application.
Figure 4B:
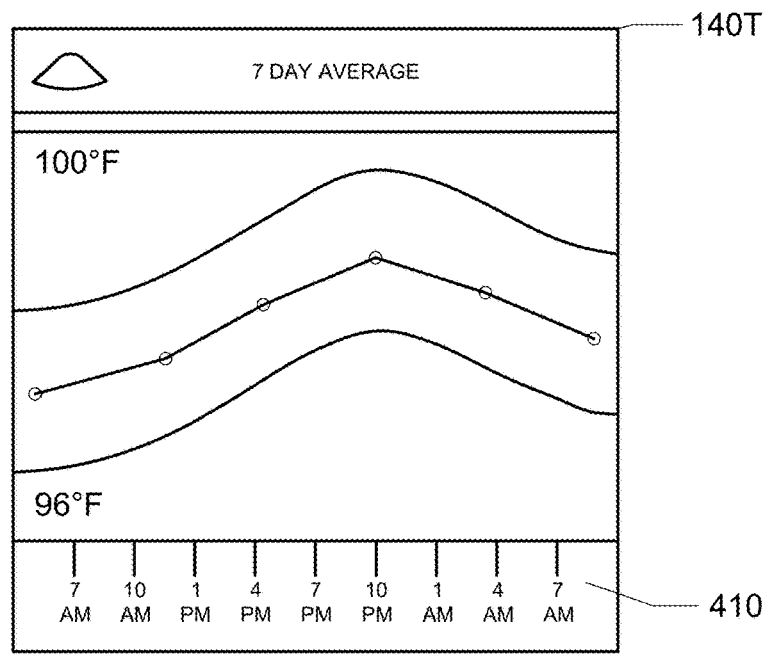

Referring now to FIGS. 4A-4B, a temperature averaging window 140T is shown being illustrated in the touch screen 202 by the scanning application software 140. This may be displayed as a result of selecting the graph button 165 of the initial scanning window 140I. The temperature averaging window 140T could include a textual heading 400 illustrating the types of graph that are plotted below. The textual heading 400 may recite "seven-day average" to let a user know that one or more seven-day average graphs are being displayed below. The portable vital signs scanner 102 may be used periodically throughout a 24-hour period each day. The seven day average may look back over a seven day window and time, plotting an average curve 401A, a maximum curve 401M, and a minimum curve 401S. The vital sign measurements are plotted on the Y-axis 411 and a time as the time of day on the X-axis 410. The portable wireless vital signs scanner 102 is expected to be used daily at multiple times during a day. In this, manner the vital signs of the user are captured periodically during the day by the vital signs scanner 102 and the personal portable wireless device 104 of the scanning system 100. The maximum curve 401M and the minimum curve 401S may be illustrating plots of the maximum value and minimum values over all scans that were previously performed. The time of day axis 410 illustrates periodic time values during the span of a 24-hour day. In one embodiment, the far most right point of the curves represents the given time of day 415 of a sliding window. In another embodiment, the time axis is fixed and the curve 401A grows from left to right during the time period as scans are made and time actually progresses. The scan points 420A-420N are illustrated along the average curve 401A. The scan points 420A-420N may represent actual scans during the day or some measure of average during the preceding seven-day period. Interpolation lines 421A-421M may be inserted between each scan point to show a trend line of how the vital sign that is measured varies during times of the day. For example, scanning point 420J may represent a scan that took place between 4:00 and 7:00 pm and how the body trends towards that during that time of day.

The illustrated seven day average graph illustrated in FIGS. 4A-4B shows a body temperature graph. This is for illustration purposes only. The vital sign measurement curves could be temperature curves, blood pressure curves, oxygenation curves, heart rate curves, breathing/respiration rate curves, for example, that represent measurements that are scanned by the vital signs scanner 102.

As more information is captured by the scanner 102 and stored in the personal portable multi-function device 104, additional results may be plotted over time to generate the vital signs curves for display by an averaging window, such as vital signs window 140T.

Figure 5A:
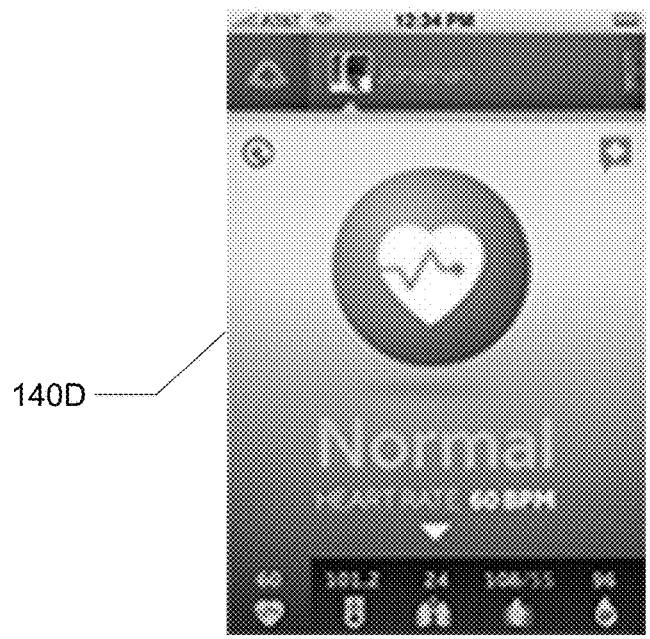
FIGS. 5A-5E illustrate prognosis windows for vital signs in a touch screen of the portable wireless multifunction device.
Figure 5B:
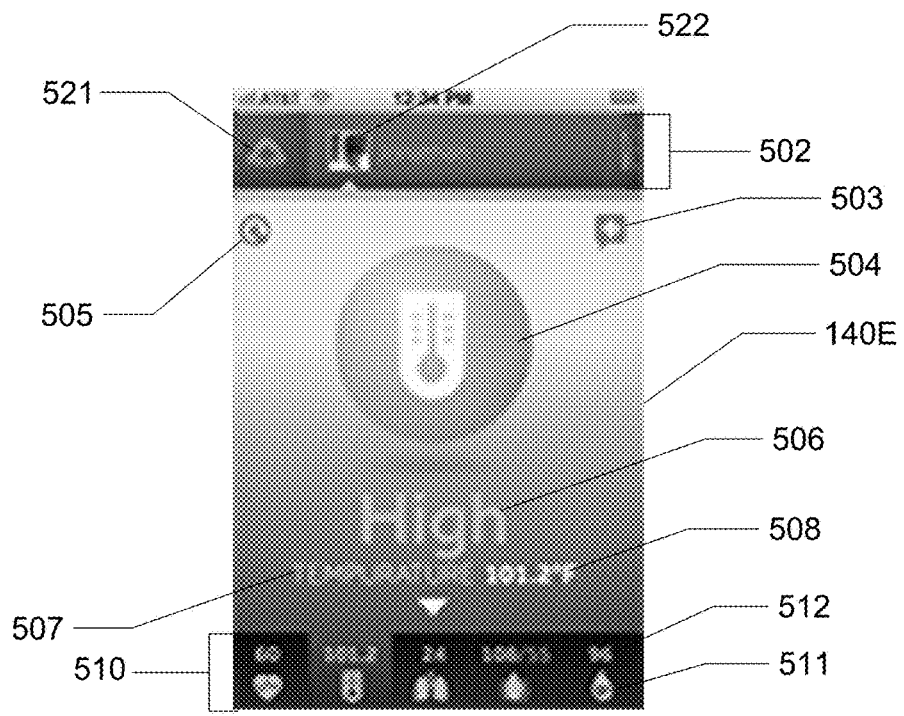
Figure 5C:
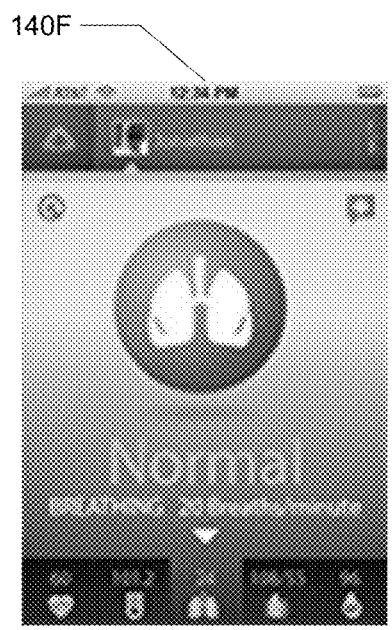
Figure 5D:
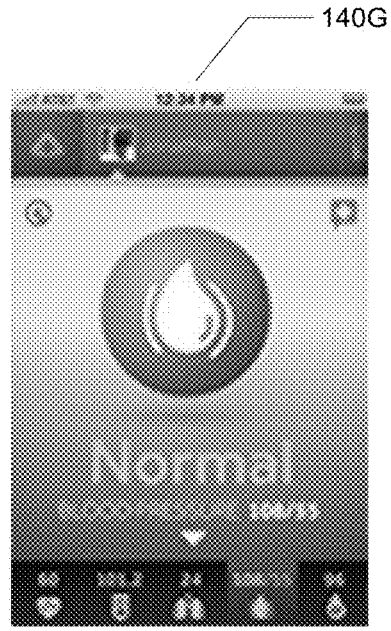
Figure 5E:
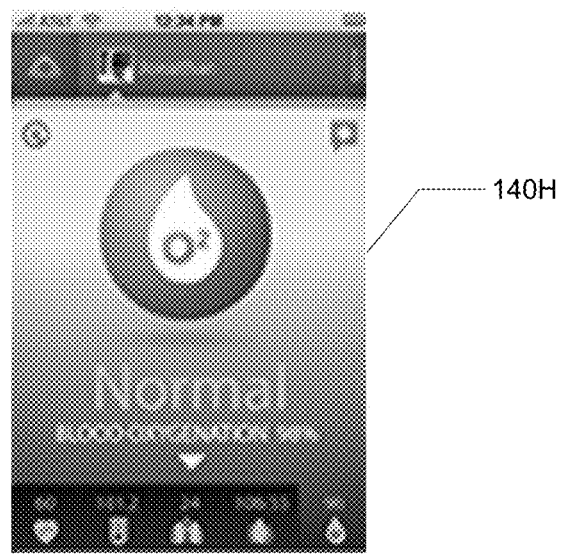

Referring now to FIG. 5A-5E, a plurality of prognosis windows 140D-140H are illustrated. In FIG. 5A, the heart rate prognosis window is shown. In FIG. 5B, the temperature prognosis window 140E is illustrated. In FIG. 5C, a breathing rate prognosis window 140F is illustrated. In FIG. 5D, a blood pressure prognosis window 140G is illustrated. In FIG. 5E, a blood oxygenation window 140H is illustrated. These windows may be selected through the use of the vital signs icons 333A-333E acting as buttons to display the respective prognosis window.

As illustrated in FIG. 5B, each prognosis screen 140D-140H, may include a navigation bar 502, one or more function buttons 503, a vital signs icon 504, a return button 505, a conditions indictor 506, a vital signs indicator 507, a measurements value indication 508, and a vital signs bar 510. The navigation bar 502 may allow a user to navigate the various screens of the vital signs application scanning software 140. For example, a scan screen icon/button 521 may be provided to jump to the scanning screen. A prognosis screen icon/button 522 may be provided to jump to the prognosis screens 140D-140H.

The vital signs bar 510 may be provided to navigate through the various vital signs prognosis windows/screens 140D-140H as well as providing a snapshot of the values of each of the vital sign measurements. In that case the vital signs bar 510 includes a measurement value indicator 512 and a vital signs icon 511 for each of the vital signs that are scanned and captured by the vital signs scanning system 100.

The return button 505 may be used to return to the previous screen that was displayed by the user interface of the scanning application software 140. The function button 503 may be an add a note button to add text about a user's condition or circumstances under which a scan was taken. The vital signs icon 504 indicates at a glance what prognosis window is being displayed.

The conditions indictor 506 for each prognosis screen will provide an indication of the most recent scan in comparison with an expected average value for a given user. For example, a temperature's vital sign is illustrated in FIG. 5B as having the condition indication of high due to a measured value of 101° F.

In the vital signs bar 510 the measurement indicator 512 and the vital signs icon 511 may be highlighted to indicate which prognosis screen is being illustrated at a glance.

Figure 6A:
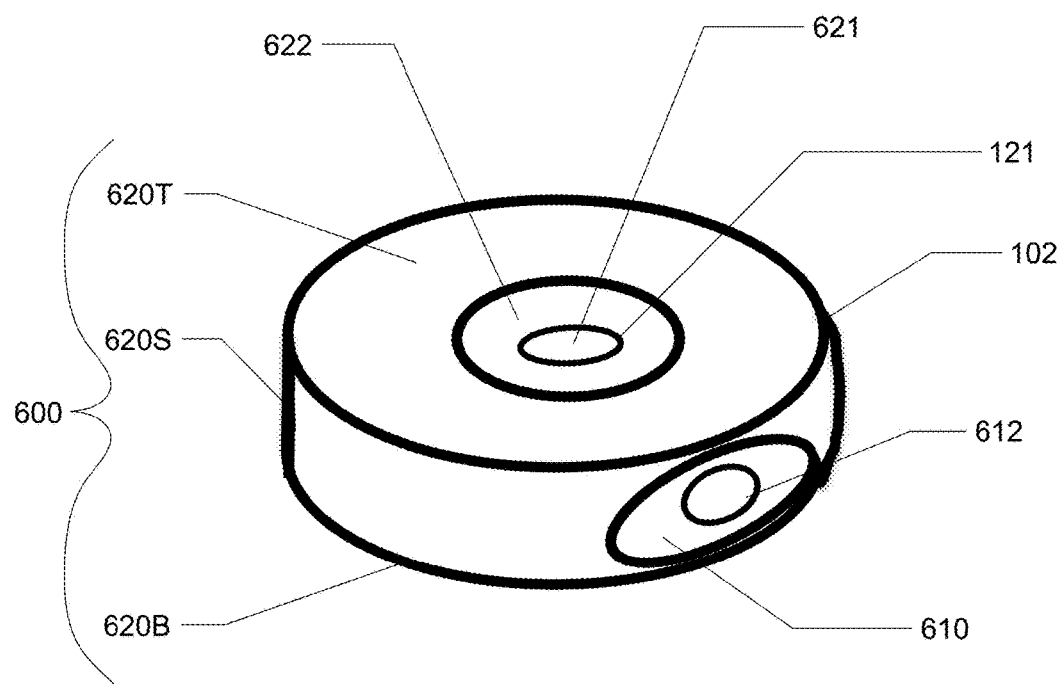
FIGS. 6A-6B are perspective views of an embodiment of the invention.

Referring now to FIG. 6A-6D, respective use of the portable wireless vital signs scanner 102 are illustrated. In FIG. 6A, a top front perspective view, the wireless vital signs scanner 102 includes a front electrode 610, and a front sensor 612 on a front side. The front electrode 610 is pressed against the user's forehead/temple, preferably at the temple, in order for the scanner 102 to make an electrical connection to the body of the user.

In one embodiment the scanner 102, a top sensor window 621 and a top electrode 622 are provided in the topside of the scanner 102. A top sensor 121 may be located underneath the top sensor window 621 to obtain a vital signs measurement from a user's finger that may be pressed on top of the window 621. A top electrode 622 may be used to form an electrical connection to a user's finger and complete a circuit of the user's body such as illustrated in FIG. 1A.

The housing 600 of the vital signs scanner 102 may generally be circular shaped and include a circular top housing 620G, a circular bottom housing 620B, and a hollow cylindrical surface 620S. The side cylindrical ring 620S may be concave, or convex over a portion of the surface. Alternatively, the cylinder side surface 620S may be a toroid shape over a portion of its body.

Figure 6B:
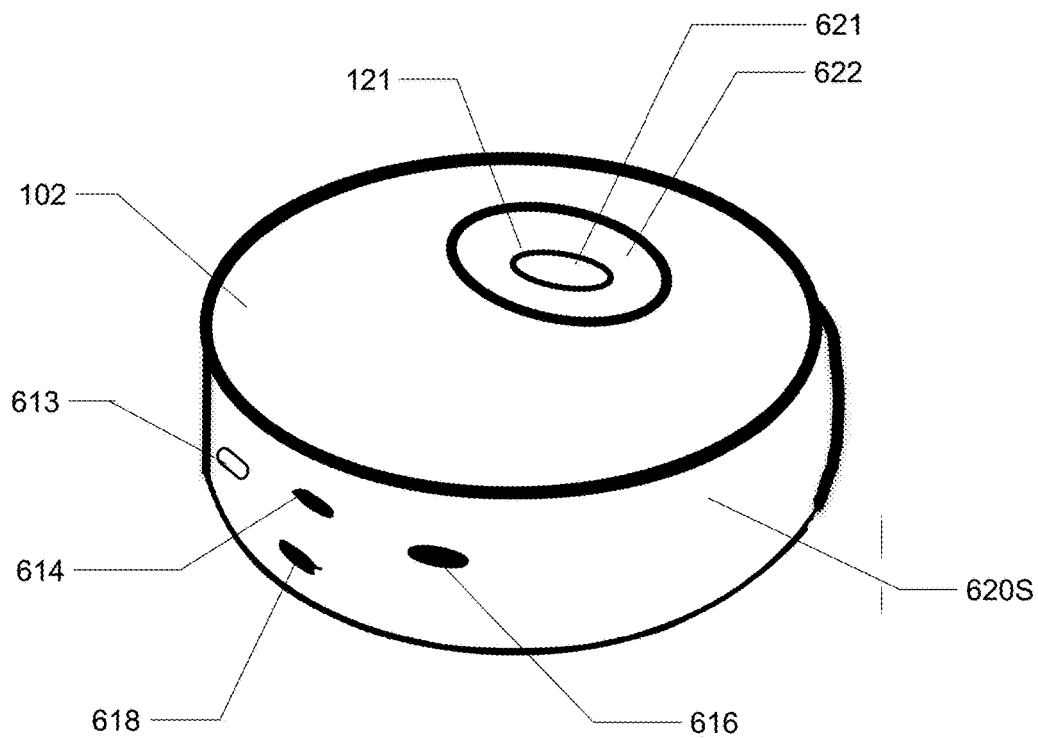

In FIG. 6B, a top back perspective view of the wireless vital signs scanner 102 is illustrated. The wireless vital signs scanner 102 illustrate various aspects of the invention in the side cylindrical surface 620S. The wireless vital signs scanner 102 includes a power button 613, a serial port connector 614, an optional wireless connection LED 618, and a power light-emitting diode 616. The power button 613 may be pressed to power the wireless vital signs scanner 102 on. The serial port connector 614 may be a micro universal serial bus connector to allow a micro USB cable to plug thereto. The micro USB port may provide an external power source to charge the rechargeable battery within the wireless vital signs scanner 102 and also may serve as a wired data port for updating firmware or transferring data to a computer or storage device. The optional wireless connection light-emitting diode 618 provides a visual indicator that the wireless vital signs scanner 102 is coupled to the wireless personal portable multi-function device 104 over its wireless communications channel 103A as illustrated in FIG. 1A. The power light-emitting diode 616 provides an indicator that the wireless vital signs scanner is powered on by the power button 613.

Figure 6C:
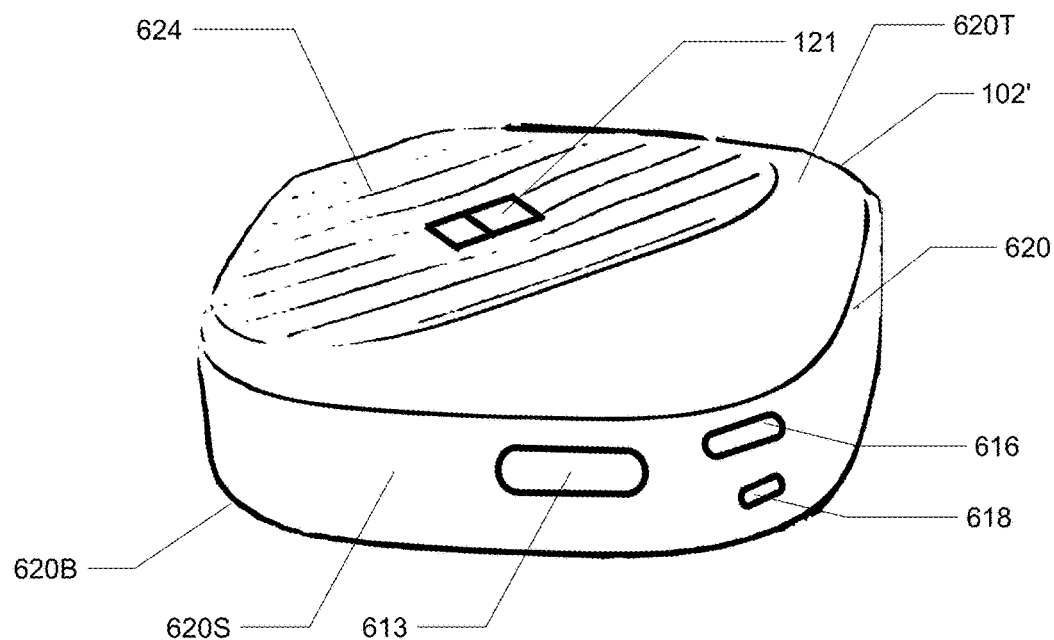
FIGS. 6C-6D are perspective views of another embodiment of the invention.

In FIG. 6C, a vital signs wireless scanner 102' is illustrated having a generally diamond shaped body housing 620. In this case the housing top 620T and the housing bottom 620B generally have a diamond or a square shape to match that of the side cylindrical surface 620S. The top or bottom housing portion 620T may each include a gripping surface 624 with corrugations or channels so that a user may comfortably and securely hold the wireless vital signs scanner 102'. The gripping surface 624 may be formed of a conductive material to aid the top and or bottom electrodes in forming an electrical connection to a user's body.

Figure 6D:
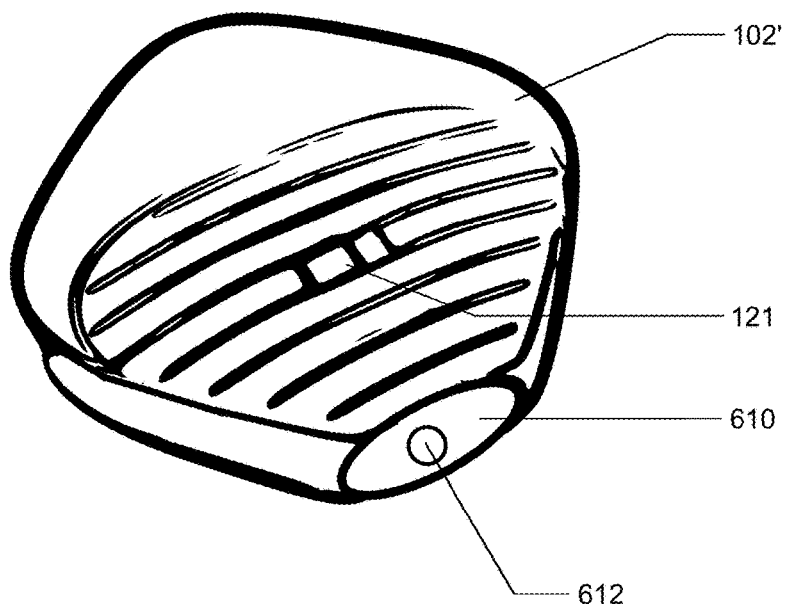

Referring now to FIG. 6D, a top front perspective view of the wireless vital signs scanner 102' is illustrated. The wireless vital signs scanner 102' includes the front electrode 610 and front sensor 612.

While the electrode 622 and the gripping surface 624 are illustrated in the top housing 620T, they may also be implemented in the bottom housing portion 620B instead of the top. Instead of an index finger making a connection with a top electrode 622, a thumb finger may couple to a bottom electrode (not shown) to provide a larger surface area contact to the body in the bottom housing portion 620B.

Figure 7A:
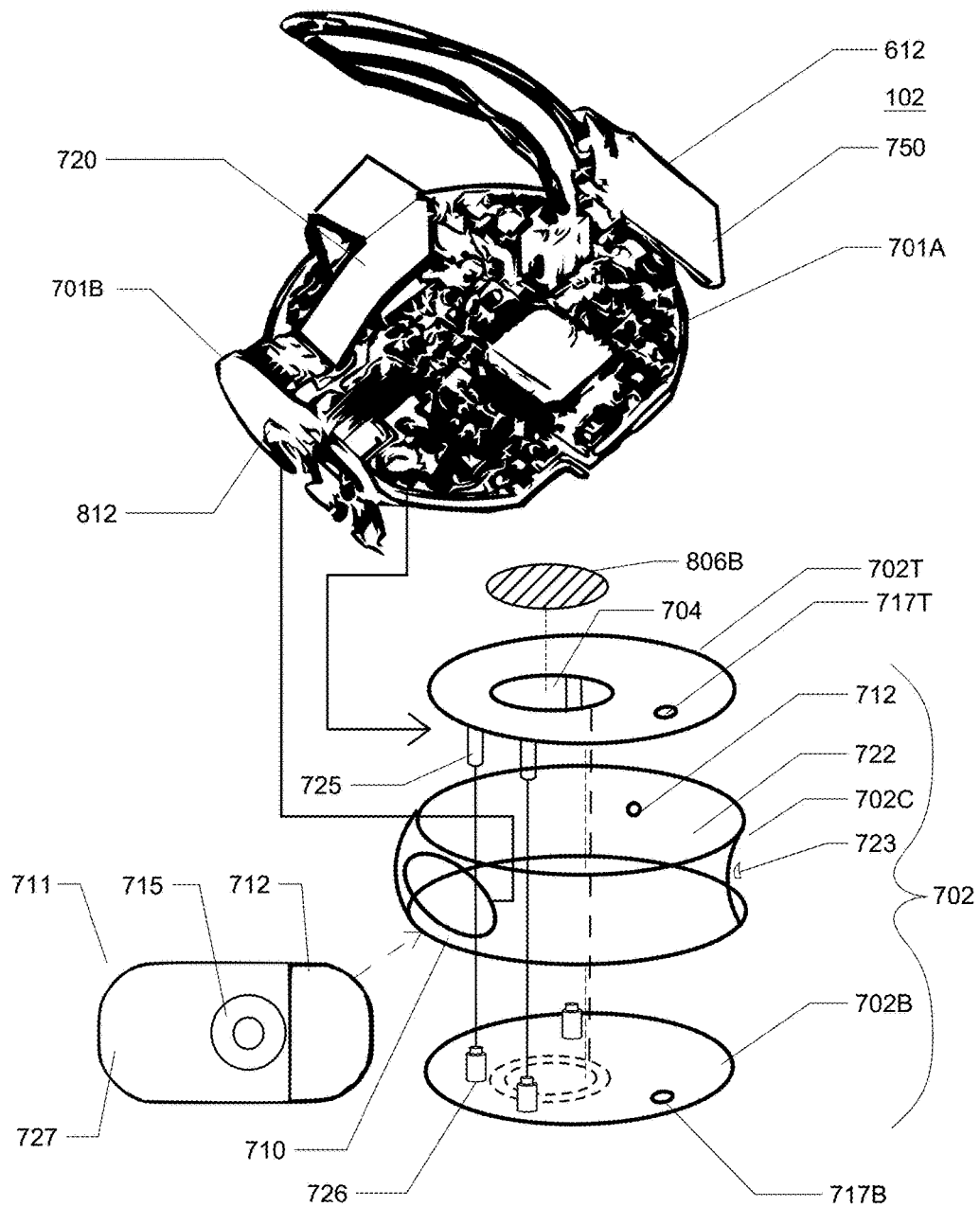
FIG. 7A is an exploded view of the exemplary portable wireless vital signs scanner.

Referring now to FIG. 7A, an exploded view of the wireless vital signs scanner 102 is illustrated. The exterior components of the wireless vital signs scanner 102 are formed of parts that can be wiped clean by a damp towelette or a disinfecting wipe. In this manner, the scanner 102 may be shared by users in a family with less worry about spreading bacteria and germs. Each user may have a personal profile or preferences stored in the scanning software application 140.

The wireless vital signs scanner 102 includes a main printed circuit board 701A and a daughter printed circuit board 701B coupled perpendicular to the main circuit board 701A. Because the scanner 102 is wireless, it includes a rechargeable battery and a connector port to which a cable may connect to recharge the battery. Preferably the battery may be charged in an hour or less. If the scanner 102 is used a few times a day, the charge of the rechargeable battery may last about a week. The main print circuit board 701A, the daughter printed circuit board 701B, and the rechargeable battery form an electronic sub-assembly 701.

The electronic sub-assembly 701 is inserted into a housing 702 of the vital signs scanner 102. The sensors on the front daughter board 701B are aligned into a front sensor opening 710 in the side housing ring 702C of the housing 702. A ribbon cable 720 electrically connects the front daughter board 701B to the main print circuit board 701A. A sensor 812 in the front daughter board 701B includes electrical leads that are coupled to the main printed circuit board 701A.

The main printed circuit board 701A is inserted into the housing ring 702C so that a serial bus connector 612 aligns with the connector opening 722 and the front sensor 812 is aligned into the front sensor opening 710. A top/bottom electrode 806B covers over an opening 704 and is electrically coupled to the main printed circuit board 701A and an ECG circuit mounted thereto.

The housing 702 of the wireless vital signs scanner 102 includes a top housing portion 702T with a top electrode 806B, a side housing ring 702C, and a base housing portion 702B. The orientation of the housing 702 for the scanner 102 may be altered such that the housing base 702B becomes the housing top 702T and the housing top 702T becomes the housing base 702B with a bottom electrode 806B to couple to a thumb. Electrodes may also be in both the housing base 702B and the housing top 702T to provide a lower resistive coupling to the user's body.

The top housing portion 702T includes a microphone opening 717T and a plurality of posts 725 and an electrical sensor opening 704. The housing base 702B may include a microphone opening 717B and a plurality of pillars 726 that can interface to the posts 725 when the housing is assembled together about the printed circuit boards.

The wireless vital signs scanner further includes a front cover 711 to fill in the front sensor opening 710 in the side housing ring 702C. The front side cover 711 includes a plastic cover portion 712 and a front electrode portion 727 with a lens 715 transparent to thermal wavelengths to allow the sensor 812 beneath it to capture a measure of temperature. The plastic cover 712 is also transparent to various wavelengths of light that are used by the vital signs sensors. The front electrode portion 727 of the front cover 711 is formed of a conductive material, such as stainless steel metal, to form a circuit when pressed up against the user's body at the forehead/temple, finger, chest or elsewhere. The shape of the front electrode 727 can vary with the shape of the wireless vital signs scanner 102.

The side housing ring 702C includes one or more LED openings 712 to receive the power light-emitting diode 616 and the optional wireless connection light-emitting diode 618. The side housing ring 702C further includes a power button opening 723 through which the power button 613 may extend.

Figure 7B:
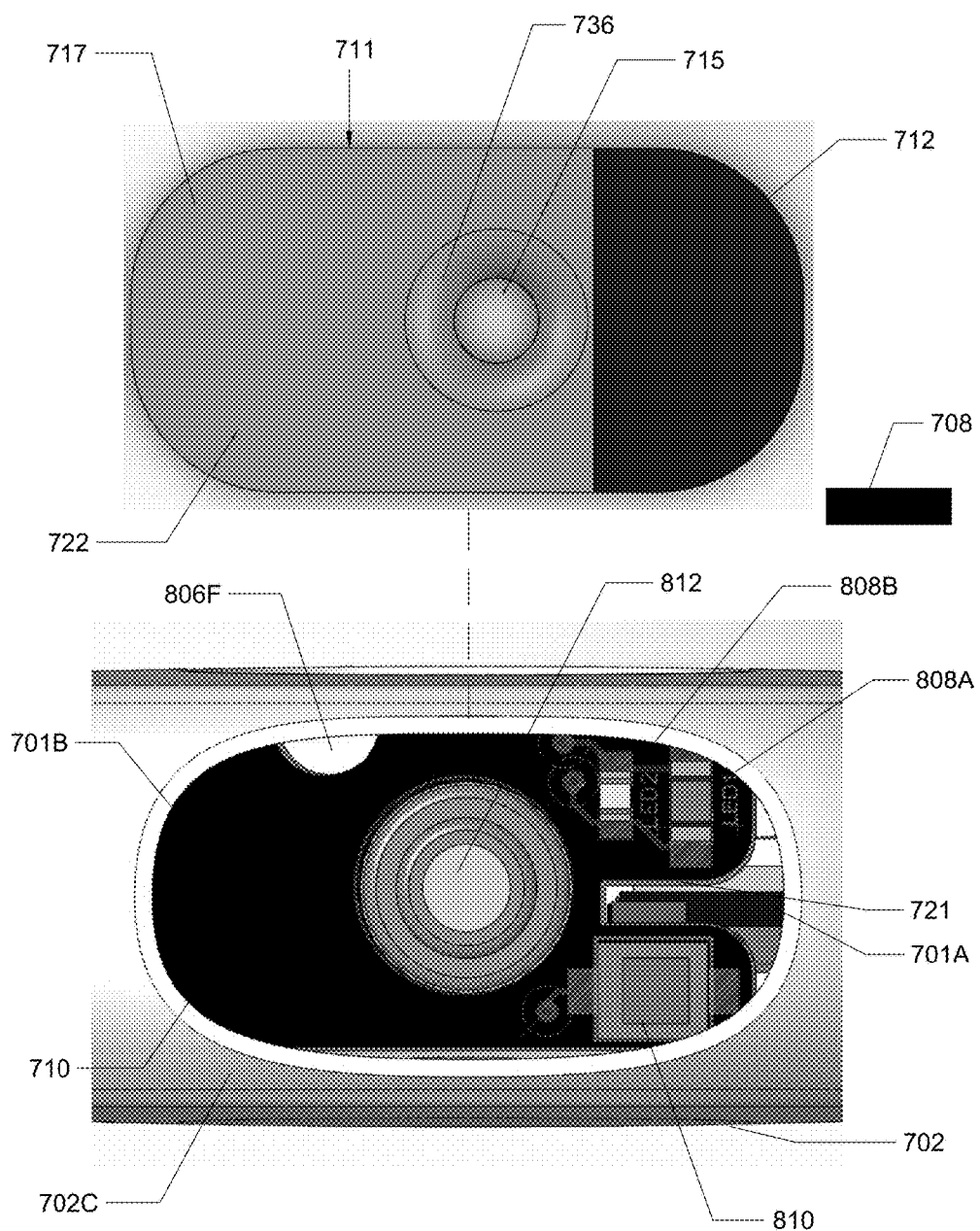
FIG. 7B illustrates a partially assembled exemplary portable wireless vital signs scanner

FIG. 7B illustrates a partially assembled wireless vital signs scanner 102. Through the front opening 710 in the side housing ring 702C, the front daughter printed circuit board 701B includes a slot opening 721. The slot opening 721 may be used to receive a shade 708 that separates the LEDs 808A-808B from the photo diode 810. The shade 708 deters light emitted by the LEDs 808A-808B from directly being impinged onto the photo diode 810. The wire (not shown in FIG. 7B) from the front electrode 727 may inserted through the opening 706 and then coupled to the main PCB and the ECG circuit. The front cover 711 can then assembled to cover over the front opening in the side housing ring 702C of the housing.

The daughter printed circuit board 701B is arranged to be substantially perpendicular with the main printed circuit board 701A. As previously discussed, the front cover 711 includes a transparent cover portion 712 and a metallic conductor portion 727, and the lens 715. The transparent cover portion 712 covers over one or more light-emitting diodes 808A-808B generating various wavelengths of light, and a photo diode 810 that receives various wavelengths of light. The light generated by the light-emitting diodes 808A-808B is shined onto the user's forehead/temple and reflected back to the photo diode 810. Light with known time periods may be generated by the light emitting diodes (LEDs) 808A-808B with different wavelengths and radiated onto a user's forehead/temple. The reflection is detected by the photo diode 810 to form an electrical signal that is analyzed. In this analysis of the signal generated by the reflected lights of different wavelengths, a measure of oxygenation in the blood stream may be generated.

The front side cover 711 includes the transparent lens 715 with a center aligned into the optical axis of the front side sensor 812 so that additional vital signs measurement may be made from the forehead/temple of the user. An opening 706 in the daughter board 701B allows a wire to pass through from the front electrode 727 and be coupled to a wire trace on the main PCB that is coupled to the ECG circuitry mounted thereto. When pressed against the user, the metallic electrode portion 727 of the front side cover 711 makes an electrical contact to the forehead/temple or other body portion of the user. An insulating ring 736 under the electrode portion 727 of the front side cover may be used to isolate any metal of the infrared thermometer 812 from the electrode portion 727.

Figure 8A:
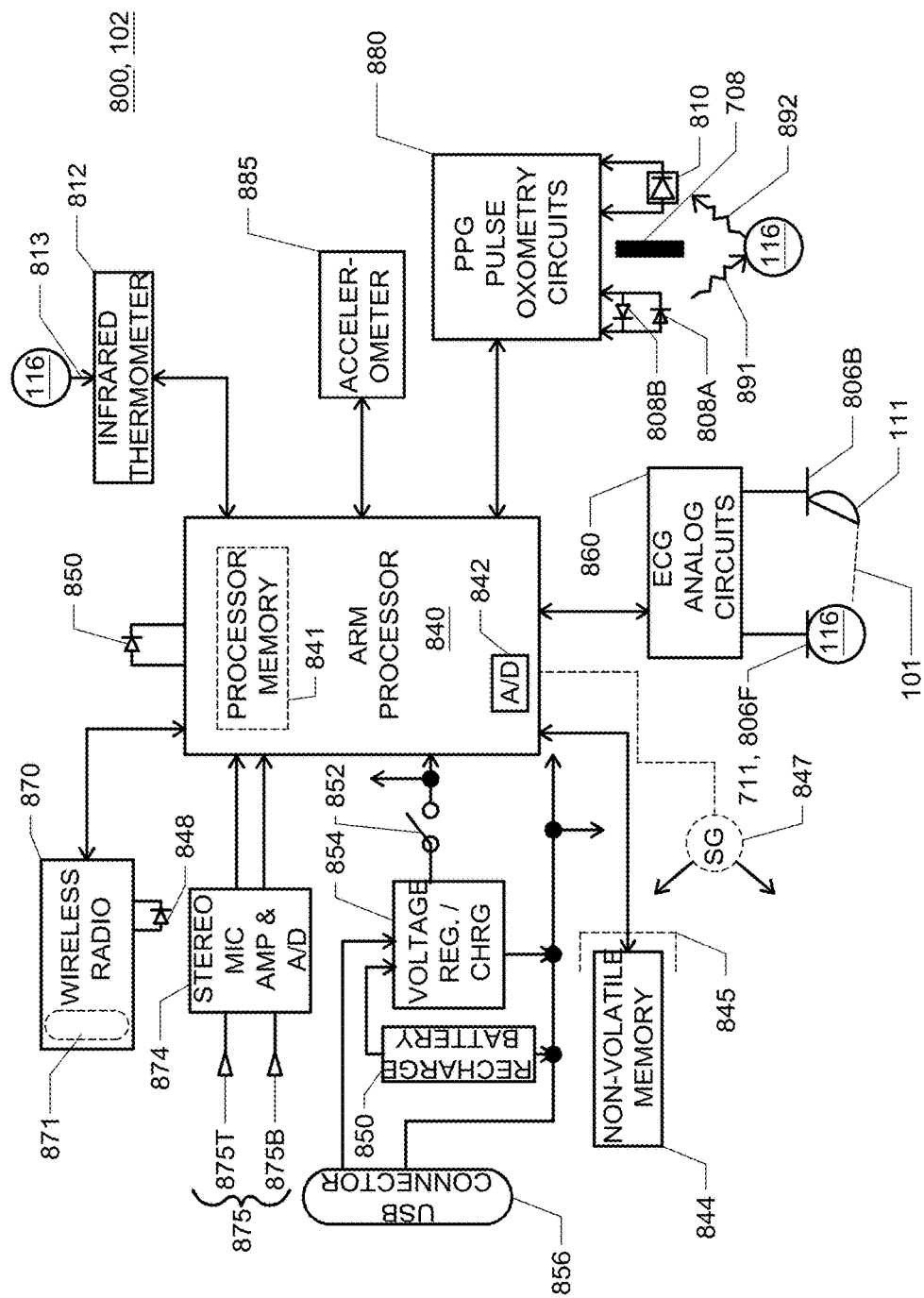
FIG. 8A illustrates a functional block diagram of electronic circuitry within the exemplary portable wireless vital signs scanner.

FIG. 8A illustrates a functional block diagram of electronic circuitry 800 within the portable wireless vital signs scanner 102. The personal portable wireless vital signs scanner 102 associated with a given user profile stored in the user data of the wireless personal multifunction device 104. The wireless communication channel 103A between the scanner 102 and the multifunction device 104 may be a secure connection with information passed between each. The devices are typically paired to each other by a code so that no other wireless device may utilize the wireless communication channel 103A. A different wireless communication channel 103B may be generated between the vital signs scanner 102 and a personal computer 150, for example. Each of the wireless communication channels 103A, 103B may be a Bluetooth communication channel, for example, in which case the signal strength between each over a Bluetooth communication channel is relatively short with a limited distance over a range between zero and twenty-five feet, for example.

Referring now to FIG. 8A, electronic circuitry 800 of the portable wireless vital signs scanner 102 includes a processor 840 at the heart of the system. The processor 840 may be a reduced instruction set processor operating with embedded operating system software. In one embodiment of the invention, the processor is an ARM processor operating with MICRIUM's embedded real time operating system (RTOS).

To provide the wireless communication channels 103A, 103B, a wireless radio 870 is coupled to the processor 841. The wireless radio 870 is coupled to an antenna 871 that could be internal, as part of an overall radio system, or external to the wireless radio 870. An optional light emitting diode 848, used as a wireless connection indicator, is coupled to the wireless radio to indicate a successful pairing with the personal portable wireless digital multifunction device 104. To scan for vital signs over a period of time such as 10 seconds, the electronic system 800 includes an infrared thermometer 812, an accelerometer 885, a pulse oximetry sensor and a pulse oximetry circuit 880, and analog electrocardiogram circuitry 860. Coupled to the electrocardiogram circuitry 860 is the bottom or top electrode 806B, the front electrode 711, bottom/top electrode connection, and the front electrode connection 806F. As shown in FIG. 1A, a portion of a human body is coupled to the front electrode 711 and the top/bottom electrode 806B to form a circuit.

The pulse oximetry circuit 880 is coupled to a pair of light emitting diodes 808A-808B. Each of these emit light patterns that are reflected off of the user's forehead/temple internally. The reflected light is captured by a photodiode 810 and coupled to the circuit 880. That is, incident light 891 from the light emitting diodes 808A-808B reflects internally off the user's head 116 as reflective light 892 which is received by the photodiode (PD) 810.

The infrared thermometer 812 detects the surface temperature of a use's forehead/temple (or elsewhere) by measuring thermal radiation (referred to as Blackbody radiation) 813 emanating from the head 116 (or other body portion to which the scanner is pressed) of a user.

To power the circuits in the system 800 of the personal portable wireless vital signs scanner 102, a rechargeable battery 850 and a voltage regulator and battery charge controller 854 are coupled together into the circuits in the system 800 when the switch 852 is closed. The battery charge controller 854 is coupled to power pins of a serial connector 856 to receive an external DC voltage supply. The external voltage supply may be used to recharge the battery and power the system 800 when it is connected. The rechargeable battery 850 may hold a charge for a period of seven days, even while scanning multiple times during each day, due to the low power consumption of the circuitry and the limited period of time needed to perform a scan of the vital signs of a user. That is, the vital signs scanner 102 is not expected to be continuously powered on during a day, but powered up periodically to perform the scans as needed.

The processor 840 may include a processor memory 841 to store system instructions to control the circuitry in the system to obtain the scans and process the information obtained through those scans into a proper user format. To store the user data from each of these scans, a nonvolatile memory 844 is coupled to the processor 840. The nonvolatile memory 844 may be soldered to a printed circuit board with the processor 840. In an alternate embodiment of the invention, a connector 845 is provided so that the nonvolatile memory 844 is a removable memory card so that a user's data may be transferred from one scanner to the next, if needed.

A power LED 851 may be coupled to the processor 840 to provide an indication that the electronic system 800 is powered up. The system can be manually shut down via the scanning software application 140 so that the scanner 102 powers off. However, the scanner 102 can also automatically shut off after a predetermined period of time to conserve power and a charge on the rechargeable battery 850. The user then just needs to press the power switch 852, once again, to turn the system back on and scan for vital signs of a user.

The processor 840 includes one or more analog digital converters 842 in order to receive analog signals from the infrared thermometer 812, accelerometer 885, pulse oximetry circuits 880, and ECG analog circuits 860. Electronic system 800 may further include a stereo microphone 875 consisting of a top microphone 875T and a bottom microphone 875B each coupled to a stereo microphone amplifier 874. The stereo microphone amplifier may have its own analog to digital converter, or the processor's analog digital convertor 842 may be used to convert analog signals into digital signals. For example, an ECG analog signal may be converted into digital signals with the analog digital convertor 842 of the processor. The stereo microphone 875 captures audio signals near the wireless vital signs scanner 102. The accelerometer 885 captures movement of the portable wireless vital signs scanner 102.

The combination of the audio information and the movement information may be utilized to determine the quality of the scanning information being obtained by the vital signs capturing circuitry. For example, the stereo microphone 875 may be used to capture noise from a user talking and plot that on a graph indicating noise spikes, or noise lines 330, such as shown in FIG. 3A. This provides feedback to a user about the quality of the scan at these intervals. The accelerometer 885 and the motion information may be similarly used to make a judgment about the quality of the vital signs scanned information being captured by the vital signs circuitry of the infrared thermometer 812, the pulse oximetry circuits 880, and the ECG analog circuits 860.

The microphones 875 in the portable wireless scanner 120 may also used to capture body sounds such as shown in FIGS. 1E-1F and store the captured body sounds in memory 844 as a potential symptom of a medical condition of the users body. For example, heart beat sounds 155 may be captured by the microphones 875 when the scanner 102 is positioned against skin of the chest 114 near ones heart 156, as is illustrated in FIG. 1E. As another example, lung or breathing of air entering and exiting ones lungs, respiration sounds 157, may be captured by the microphones 875 when the scanner 102 is positioned against skin of the chest 114 near a lung 158 in ones body, as is illustrated in FIG. 1F.

To further optimize scanning results, scan quality algorithm monitor the vita signs scanning process and can provide feedback (visual and/or audible) to the user, such as through the multifunction device 104.

An optional audible sound generator 847 in the scanner 102 may be coupled to the processor 840 to provide audible user feedback to the user during the scanning process. The user feedback may help the user to perform better vital signs scan with the wireless vital signs scanner 102 and acquire a higher quality of vital signs measurements. The audible sound generator 847 may generate alert sounds indicating when the scanning process begins and ends. It may also generate an error signal indicating to the user that he is not properly using the scanner 102 and look for instructions on the device 104.

Figure 8B:
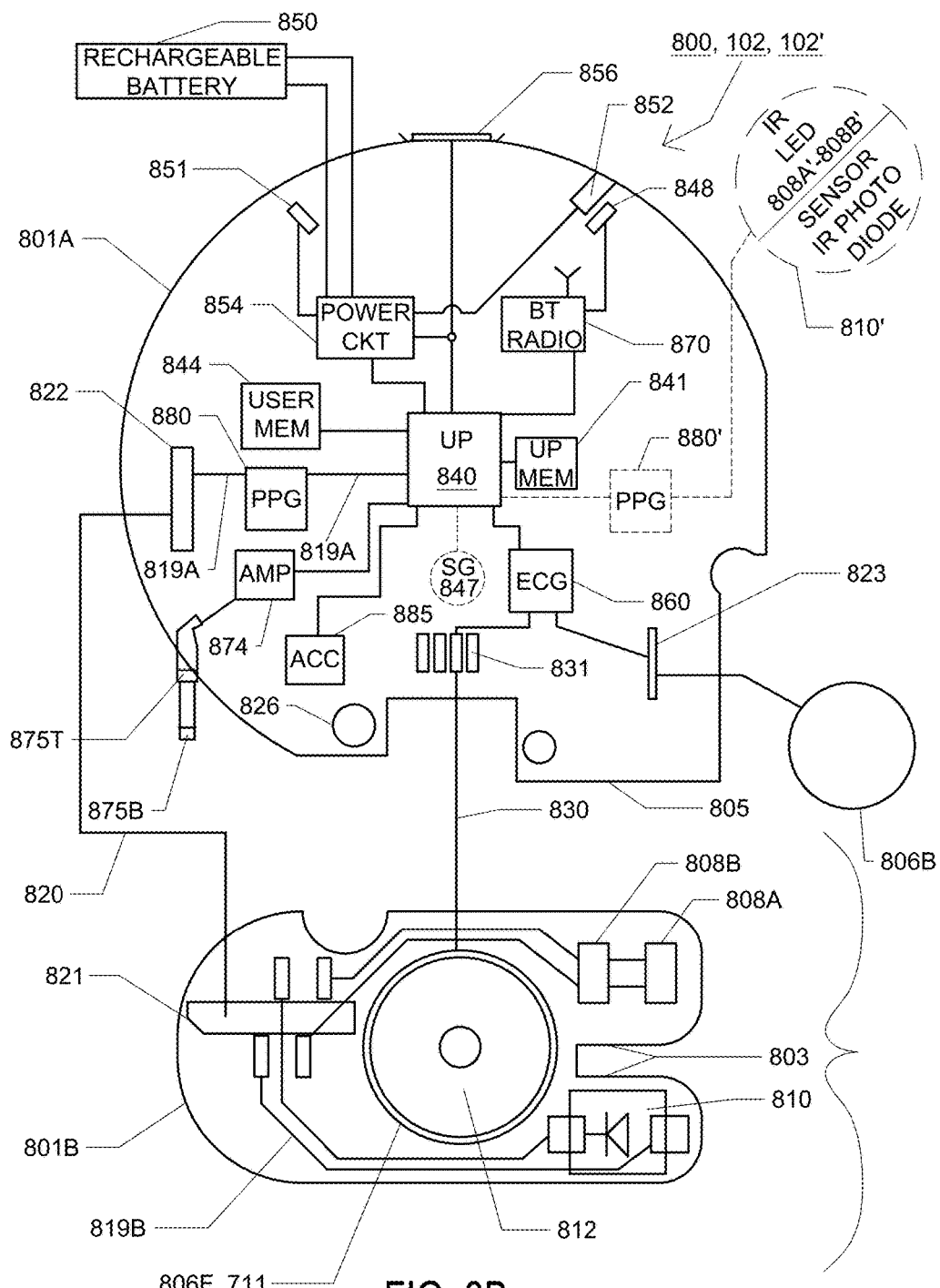
FIG. 8B illustrates a main printed circuit board coupled to a daughter printed circuit board with various electronic circuitry within the exemplary portable wireless vital signs scanner mounted to each.

Referring now to FIG. 8B, a block diagram of the electronic circuits 800 is shown mounted onto the main printed circuit board 801A and the daughter printed circuit board 801B. FIG. 8B also illustrates alternate locations for electronic circuits in the system 800 for alternate embodiments of the vital sign scanners 102, 102'.

A slot 803 in the daughter printed circuit board 801B receives a shade device 708. Light emitted by the LEDs 808A-808B is shaded by the shade device 708 so that it may not directly impinge onto the photo diode 810 in the daughter PCB 801B. Reflected light, reflected off the user's body, is desirable to be captured by the photo diode 810.

Wire leads 830 of the IR sensor 812 and the front electrode contact 806F are coupled to pads 831 of the main printed circuit board 801A. First and second LEDs 808A-808B and the photodiode 810 are coupled to connector 821 by conductive traces 819B on the daughter printed circuit board 801B.

The main printed circuit board 801A has a plurality of wire traces 819A coupling circuits mounted thereto together. The daughter printed circuit board 801B includes a plurality of traces 819B coupling circuits mounted thereto to connector 821. A ribbon cable 820 is used to couple signals between the daughter memory card 801B and the main printed circuit board 801A for the oximetry circuit 880. The oximetry electronic circuit 880 is coupled between the connector 822 and the processor 840 on the main printed circuit board 801A. One set of one or more wire traces 819A couple the oximetry electronic circuit PPG 880 to the connector 822. Another set of one or more wire traces 819A couple the oximetry electronic circuit PPG 880 to the processor 840.

In accordance with one embodiment of the invention, if the oximetry sensors are moved to a top portion of the housing to sense oximetry through a finger, with the IRLEDs 801A'-801B' and the IR photodiode 810', the oximetry circuitry may be moved to the opposite side as the oximetry electronic circuit PPG 880' coupled between the processors 840 and the LEDs 808A'-808B', IR photodiode 810' and mounted in the top portion of the housing.

The bottom or top electrode 806B is formed of stainless steel to provide a good connection to either a thumb finger or an index finger. The electrode 806B is coupled to a connector 823 and to the ECG circuitry 860 on the main printed circuit board 801A.

The main printed circuit board 801A includes the processor 840, the wireless radio 870, the microprocessor memory 841 (either internal or external as shown mounted to the printed circuit board), an accelerometer 885, an amplifier 874, oximetry circuitry 880, 880', user memory 844, and battery charge circuit 854.

Top and bottom microphones 875T and 875B extend out from the main printed circuit board 801A by ribbon cables so that they may be mounted into the respective openings in the housing top and housing bottom. The microphones 875T, 875B may be coupled to the amplifier 874 which in turn may couple audio signals into the microprocessor 840. Mounted to the main printed circuit board is the power LED 851 and the connection LED 848. Further mounted to the main printed circuit board is a power on/off switch 852 coupled to the voltage regulator battery charge circuit 854 to signal for it to turn power on or off to components with the scanner 102. Additionally, mounted to the main printed circuit board 801A is a serial connector 856 coupled to the microprocessor. In one embodiment invention, the serial connector 856 is a micro universal serial bus connector.

An optional audible sound generator 847 may be mounted to the main PCB 801A and coupled to the processor 840 as shown. To avoid interference, the sound generator 847 may be positioned away from the microphones 875.

Main printed circuit board 801A includes a plurality of openings 826 that receive the pillars 725, 726 of the housing top 702T and housing base 702 B.

The daughter printed circuit board 801B includes a connector 821, light emitting diodes 801A-801B, and a photodiode 810 mounted thereto. The IR sensor 812 is inserted through a hole in the daughter PCB 801B, attached thereto with an adhesive, and supported thereby. The front electrode 806F around the IR sensor 812 is attached with an adhesive to the daughter PCB 801B for support.

The ribbon cable 820 couples signals of the light emitting diodes 801A-801B and the photodiode 810 regarding oximetry between the daughter board 801B and the main printed circuit board 801A for the oximetry circuit 880. With the terminals 830 of the IR sensor 812 coupled to the pads 831 of the main PCB 801A, signals of the IR sensor 812 regarding temperature are coupled into the processor 840. With the terminals 830 of the front electrode 806F coupled to one or more pads 831 of the main PCB 801A, signals of the ECG circuit 860 to measure heart activity (e.g., heart rhythm, heart rate, etc.) may be coupled into and out of a users body.

Thus, the personal portable wireless vital signs scanner integrates a plurality of sensors and a controller/processor together to synchronously obtain a plurality of vital signs at different times during a users day. Despite the integration of multiple sensors and a controller/processor into the scanner, the vital signs scanning device has a relatively low production cost. The integration with a ubiquitous consumer electronic device pre-owned by many users, the personal wireless multifunction device (e.g. smartphones, tablets, etc.), to display the vital signs data with vital signs scanning software, also keeps the costs low of the overall personal vital signs scanning system. The low costs of production of the vital signs scanner can allow lower retail pricing and higher volume of sales, enabling an average consumer to afford the vital signs scanning system to personally scan and monitor trends of their vital signs for as an important part of preventive medical care of their own bodies.

Figure 9:
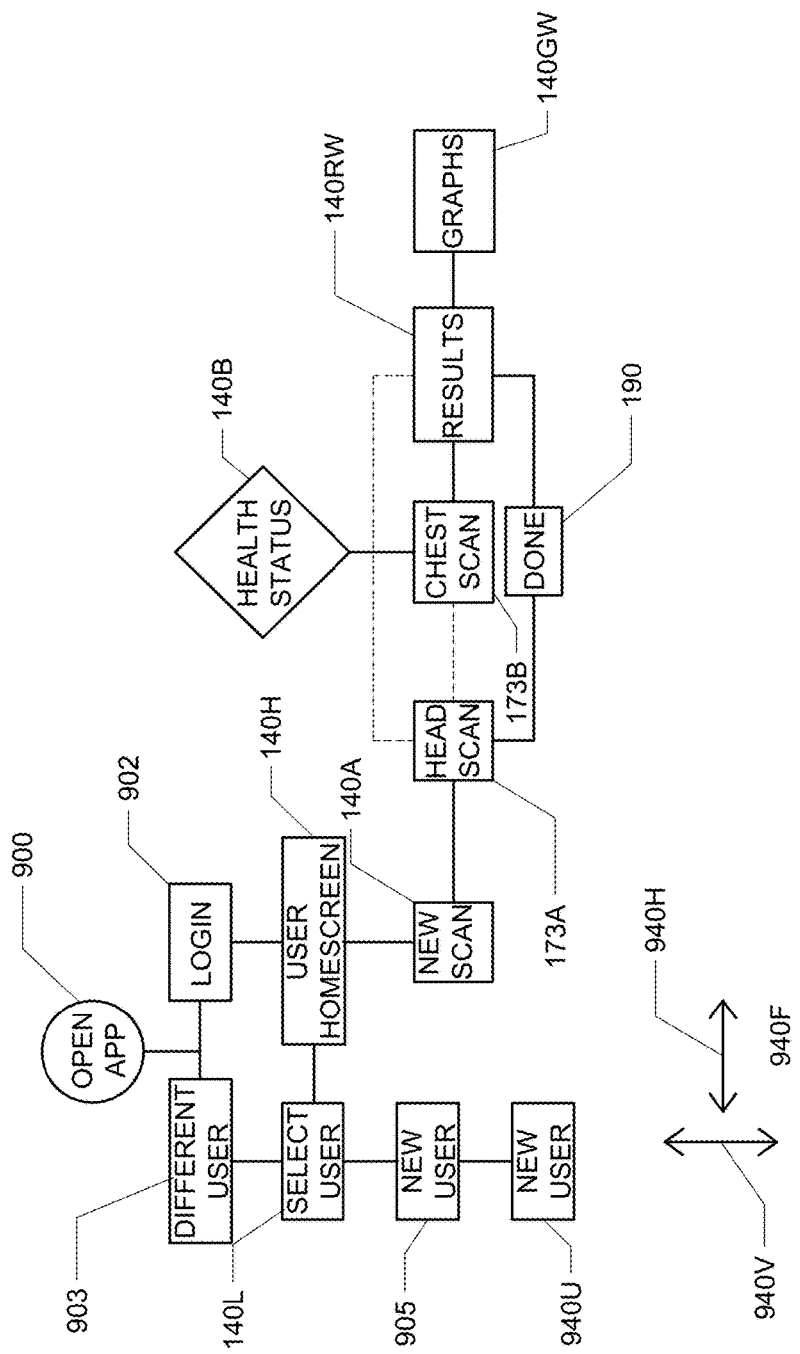
FIG. 9 illustrates an exemplary hierarchy of the vita signs graphical user interface provided by the vital signs scanning software application executed by the personal wireless multifunction device.

Referring now to FIG. 9, a diagram illustrating an exemplary hierarchy of windows provided by the scanning application software 140 is illustrated. A variety of vital sign scanning user interface windows of the scanning application software 140 have been described. The vital signs scanning application software 140 executed by a processor provides a user interface hierarchy of the vital sign scanning user interface (VSUI) windows. For example after the vital sign scanning application is opened at process 900, a scanning login button 902 may be presented to the user by the scanning application software 140. If the user is properly selected he chooses the login button to transition to a user home screen 140H.

In the user home screen 140H, a user inputs his login identification and password to gain access to personal vital signs scan data stored in the device 104. If the user is a different user a different user button 903 may be selected or a horizontal swipe finger gesture 940H may be used to go to a select user window 140L. If the user is not listed and is a new user, the select user window 140L may have a new user button 905 that jumps to a new user window 904U that is displayed to the user.

In the new user window 940U, the new user may input his login user ID and password that he desires to use with the scanning software application to identify his personal vital signs scan data. Other information, such as sex, height, weight associated with a time and date may be entered by the user. As the days and/or years go by, the user may update this information in the profile so that the vital signs scanning system better knows what conditions might occur for the given user. The login and profile windows can also allow the scanning system to be shared with other users in a family. After logging in with user ID and password through the home screen, the scanning system application may display the initial scanning window 140A.

By using a horizontal finger gesture 940H over the scan type slider 171, the user may select a head scan 173A, a chest scan 173B, the results window 940RW (e.g., windows 307,350-353 in FIGS. 3B-3C, windows 140D-140H in FIGS. 5A-5E)), or the graphs window 940GW (e.g., window 140T shown in FIGS. 4A-4B). If at any point in time the user feels the need to terminate the scanning process, the done button 190 in the user interface may be selected. By means of a vertical finger gesture 940V in the scanning window 140A during a head scan 173A or chest scan 173B, or the results window 940RW, the health status window 140B may be displayed. Alternatively, a health status button 180, such as shown in FIG. 1C, may be selected to display the health status window 140B.

Each of the screens/windows/slides of the vital signs scanning application may be navigated by pressing one or more virtual graphical buttons (e.g., back, done) and/or making one or more finger gestures 940F (e.g., vertically up/down 940V, horizontally left/right 940H) dragged across a touch screen. A navigation bar may alternatively be provided with navigation buttons to navigate between selected windows. The menu button may also be used to navigate to different windows. In other cases, pressing a button displays a different screen/window/slide such as the done button.

After scanning is completed, the scanning application software can automatically display the results window 140RW. Additional buttons in the results window 140RW may be used to navigate to various graph windows 140GW, such as the temperature graph window shown in FIGS. 4A-4B. Additional buttons in the results window 140RW may be used to navigate to various prognosis windows, such as prognosis windows 140D-140H shown in FIGS. 5A-5B. In this manner, vital signs data and information can be displayed to the user in various ways.

The scanning software application 140 includes a number of instructions and routines that are executed by a personal wireless multifunction device 104. The personal wireless multifunction device 104 may include a smart phone, an APPLE IPHONE 5, IPHONE 4S and SAMSUNG GALAXY S III that support Bluetooth Smart. To help everyone use the device, assistive technology may be added to the scanning software application 140.

The significant software routines of the scanning software application 140 include a scan procedure controller based on scan quality algorithm, UI implementation, wide area network interfacing to cloud services, scan results interpretation, and trend charting.

Interactive Scanning and Quality User Feedback

The forehead and temple (forehead/temple) of a user has been identified as place to concurrently acquire multiple vital sign measurements of a user's body over a period of time (e.g., a ten or thirty second scan). The relatedness in time between the multiple vital sign measurements allows them to be use together to determine scan quality. The scanner has integrated sensors for concurrent data capture, making the scanner more capable than a single sensor alone, not only for multiple vital signs measurements but also for quality feedback regarding data capture.

There are a number of operating conditions that may not provide optimal scan data and scan results when the portable vital signs scanner 102 is scanning. If these operating conditions can be avoided, the scan data and the scan results obtained therefrom can be improved. It is desirable to provide vital sign scan quality control for a better user experience. It is desirable to provide vital sign scan quality feedback to a user. The multiple sensors in the vital signs scanner 102 that concurrently acquire data enable a vital sign scan quality control. Integrated user interface devices (e.g., sound generator 847) in the scanner 102 and the vital signs user interface 140 provided by the portable multifunction device 104 and the software executed therein may provide an interactive scanning process to improve the user experience during a vital signs scan.

User feedback regarding the quality of a scan, quality feedback, can be provided in real time by the scanner 102 and the vital signs user interface 140 provided by the device. For example, a text message could be displayed or a voice message could be audibly generated such as "Please hold the scanner still for good scan" if the user's hand is detected to be shaking it. A text message could be displayed or a voice message could be audibly generated such as "Please touch the scanner against your forehead/temple to start scan", for example, if feedback suggest that the scanner is not touching the forehead/temple of the user.

Quality feedback can be provided by fusing motion detection of the scanner and individual evaluation of signal deviation of each vital sign sensor data from an expected normal range. There are three general observations that can be made into an algorithm regarding data capture quality in the portable vital signs scanner: 1) Significant motion from the accelerometer indicates that the data capture of ECG and Pulse oximetry data will not be good; 2) The signal quality from ECG, Pulse oximeter and IR thermometer sensors are independently evaluated; and 3) For high-quality data capture, data from all vital sign sensors should be good.

Figure 10A:
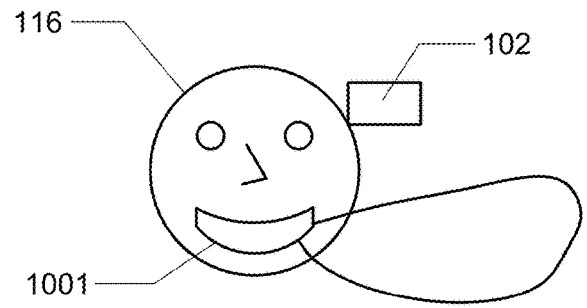
FIGS. 10A-10B illustrate diagrams of sources of movement of the vital signs scanner that can degrade data capture.
Figure 10B:
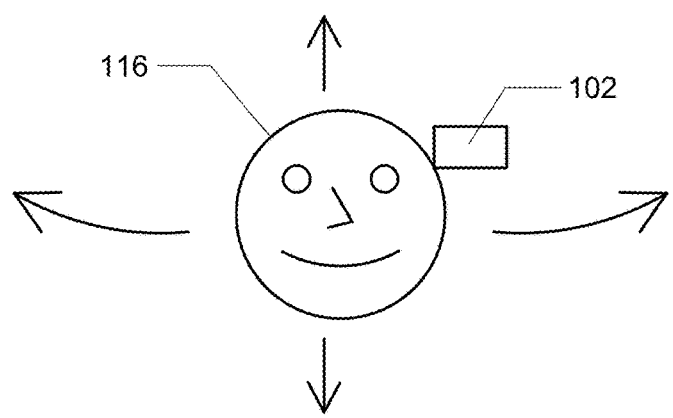

Referring now to FIGS. 10A-10B, sounds and movement of a user's head may affect the quality of information that can be captured by the vital signs scanner. In FIG. 10A, a user is talking and moving his mouth 1001 while holding the vital signs scanner 102 against his forehead/temple 116. The movement of the users mouth can create vibrations that may disturb the electrical connections between scanner and body as well as the infrared scans between the vital signs scanner 102 and the forehead/temple 116 of the users head. The microphone 875 in the vital signs scanner 800 can help detect people talking during forehead/temple scan.

Referring now to FIG. 10B, a user may also shake his head and forehead/temple 116 left and right as shown by the left and right arrows, such as when talking with another or lacking in attention. A user may also nod his/her head and forehead/temple 116 up-and-down as shown by the up and down arrows, such as when talking or lacking in attention. The movement of a user's head and forehead/temple can also cause the vital signs scanner 102 to unreliably record vital signs data.

Figure 11A:
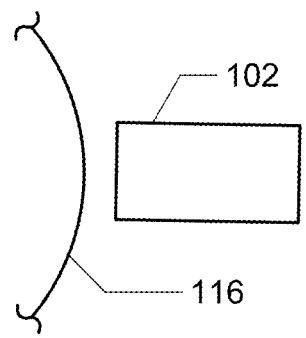
FIGS. 11A-11C illustrate diagrams of sources of various degraded quality in the capture of vital signs data by the vital signs scanner.
Figure 11B:
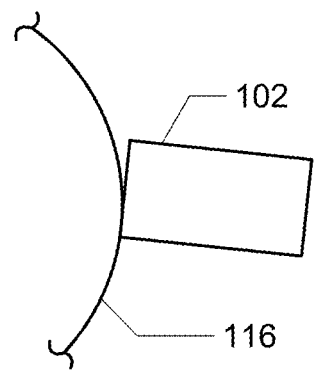
Figure 11C:
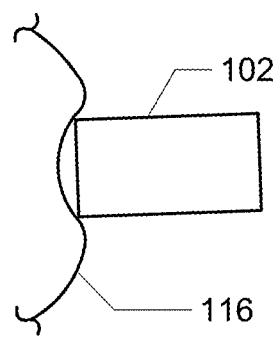

Referring now to FIGS. 11A-11C, the degree to which the vital signs scanner 102 is pressed against the user's forehead/temple 116 can also affect the reliability of the data recorded by the vital signs scanner 102.

In FIG. 11A, the vital signs scanner 102 does not touch the forehead/temple 116 of the user, making no contact, and thus the scanner cannot complete a circuit with the body or reliably detect temperature. Scan data captured by the vital signs scanner 102 in this case would not be valid.

In FIG. 11B, the vital signs scanner 102 only lightly touches the forehead/temple 116 of the user being too gentle such that a poor contact is made between the vital signs scanner and the user's body. The electrical connection between the forehead/temple and the vital signs scanner is overly resistive. The angle the infrared scanner makes with the skin of the users forehead/temple is not substantially perpendicular. In this case, the vital signs data captured by the vital signs scanner are poor and unreliable.

In FIG. 11C, the vital signs scanner 102 is pressed overly hard against the user's forehead/temple 116. In this case, the vital signs scanner 102 may be pressed too hard against skin causing it to bulge inward away from the sensors/contacts and/or cut off blood circulation in a vein underneath the sensors. With reduced skin contact, the electrical connection between the forehead/temple and the vital signs scanner may be overly resistive and the ECG scan data may be poor or invalid. A distance the infrared scanner makes with the skin of the user's forehead/temple may be overly large such that poor temperature measurements may be made. With reduced blood circulation underneath the pulseOX sensor, the pulseOx scan data may be poor. In this case, the vital signs data that is captured by the vital signs scanner is poor and unreliable.

It is desirable, to provide an interactive scanning system with user feedback. When the vital signs scanner 102 is being improperly utilized, user feedback may be provided so that the user can alter his/her manner of using the vital signs scanner 102 so that better data quality is achieved to enable reliable vital signs data capture.

As shown in FIG. 8A, The vital signs scanner 102 includes a processor 840 and a memory 841,844 to store software program instructions for execution by the processor. The software program instructions may provide an interactive scanning process and user feedback (with or without the digital device 104 and its scanning user interface) to improve the quality of scanning data and results.

The microphone 875 in the vital signs scanner 800,102 may be used to detect the sounds of a human body to determine new vital sign values or information when placed at an appropriate body part, for example, neck or chest. The audio samples can be analyzed for and detect specific sounds of the human body. The information obtained from the sounds may be fused together with other data to determine a new vital sign value or a diagnosis of a user's body. The microphone 875 may optionally be used to detect sounds of a user talking during a forehead/temple scan, for example, to aid in improving the quality of vital signs measurements and vital signs data.

The scanner 102 includes an accelerometer 885. The accelerometer 885 senses acceleration due to the movement of the scanner. The accelerometer 885 can be used to improve the quality of vital signs data. For example, the accelerometer 885 in the vital signs scanner 800, 102 can be used to detect movement of the users head and forehead/temple 116 that is to contact the scanner. The accelerometer is preferably a three-axis accelerometer measuring acceleration (in units of gravity g) in three orientations generating three acceleration output signals. With three-axis accelerometer information, the orientation of the scanner with respect to earth and user can be determined in the typical scan scenario. The three-axis accelerometer information can help determine whether the user is using the scanner properly. To measure the total acceleration without knowing the specific orientation of the accelerometer in the scanner, the square root of sum of squares (RSS) formula may be applied to all three outputs to form a single acceleration measurement of the scanner. As the gravitation force (g-force) at the surface of the earth is typically one (1) g (9.80665 meters per second squared), the relative acceleration of the scanner 102 may be determined by simple comparison of the single acceleration measurement with earth's surface gravitational force of one g.

The measured relative acceleration by the accelerometer 885 may be categorized into relative degrees of motion based on the results of the comparison earth's gravitational surface force of one g. The relative degrees of motion that may be detected by the accelerometer 885 and the vital signs scanner 800, 102 are still (also referred to as no motion) 1217S, small or minor motion 1217M, and big or significant motion 1217B. Significant or big motion 1217B may be on the order of one tenth g (0.1 g) or greater deviation from one g (1 g), for example. Small or minor motion 1217M may be on the order from two hundredths g (0.02 g) up to one tenth g (0.1 g) deviation from one g (1 g), for example. Still or no motion 1217S may be a smaller deviation on the order of less than two hundredths g (0.02 g) deviation from one g (1 g), for example.

The detected motion by using the relative acceleration by the accelerometer 885 can be combined or fused together with the sensor data from the vital sign sensors to be a collaborative decision regarding the quality of vital signs data during a scanning session by the user.

One of a user's fingers not only serves to hold and support the scanner 102, but also as one contact point for the ECG circuit 860 (the other one-lead ECG contact point is forehead/temple). The ECG circuit 860 and its electrodes 711, 806F,806B may be used to determine how well (resistivity) an electrical contact is formed with the forehead/temple and finger of the user's body during the scanning process over a period of time.

Scan data from the PPG sensor and/or the ECG sensor and their respective circuits may also be used to determine scan data quality. If the PPG scan data is off scale (saturated), then it provides an indication that there is no or too loose of a contact of the scanner 102 with a users' skin. If there is no PPG scan data signal but a good ECG scan data signal is present, this provides an indication that too much pressure being is applied and hence no pulse recording is possible to generate PPG scan data. Accordingly, the ECG scan data and the PPG scan data can be checked in this manner, fusing together the outcome to determine if an appropriate amount of pressure is being applied to the scanner to press it against the user's body to obtain quality scan data for ECG and PPG measurements.

The vital signs scanning user interface 140 executed by the portable digital device 104 is used to provide user feedback on its touchscreen display device 202 or its speaker 216. The user uses one hand to hold the vital signs scanner 102 while his/her other hand holds the portable wireless device 104 (e.g., a smartphone) to view the touchscreen display device 202. Alternatively or additionally, the audio sound generator 847, a speaker, in the vital signs scanner 102 may be used to provide user feedback.

User feedback may also be visually provided to a user by use of text messages on the display 202 of the device 104 during the interactive scanning process and data acquisition by the scanner 102. User feedback may also be visually provided to a user by use of color coding on the display 202 of the device 104 during the interactive scanning process and data acquisition by the scanner 102. For example, the color code of green on a field or an object in the user interface can indicate that the proper amount of pressure is being applied to the scanner to press it against the user's body. A color code of red on a field or an object in the user interface, for example, may indicate that too much pressure is being applied to the scanner to press it against the user's body. A color code of yellow on a field or an object in the user interface, for example, may indicate that not enough pressure is being applied to the scanner to press it against the user's body.

Figure 12:
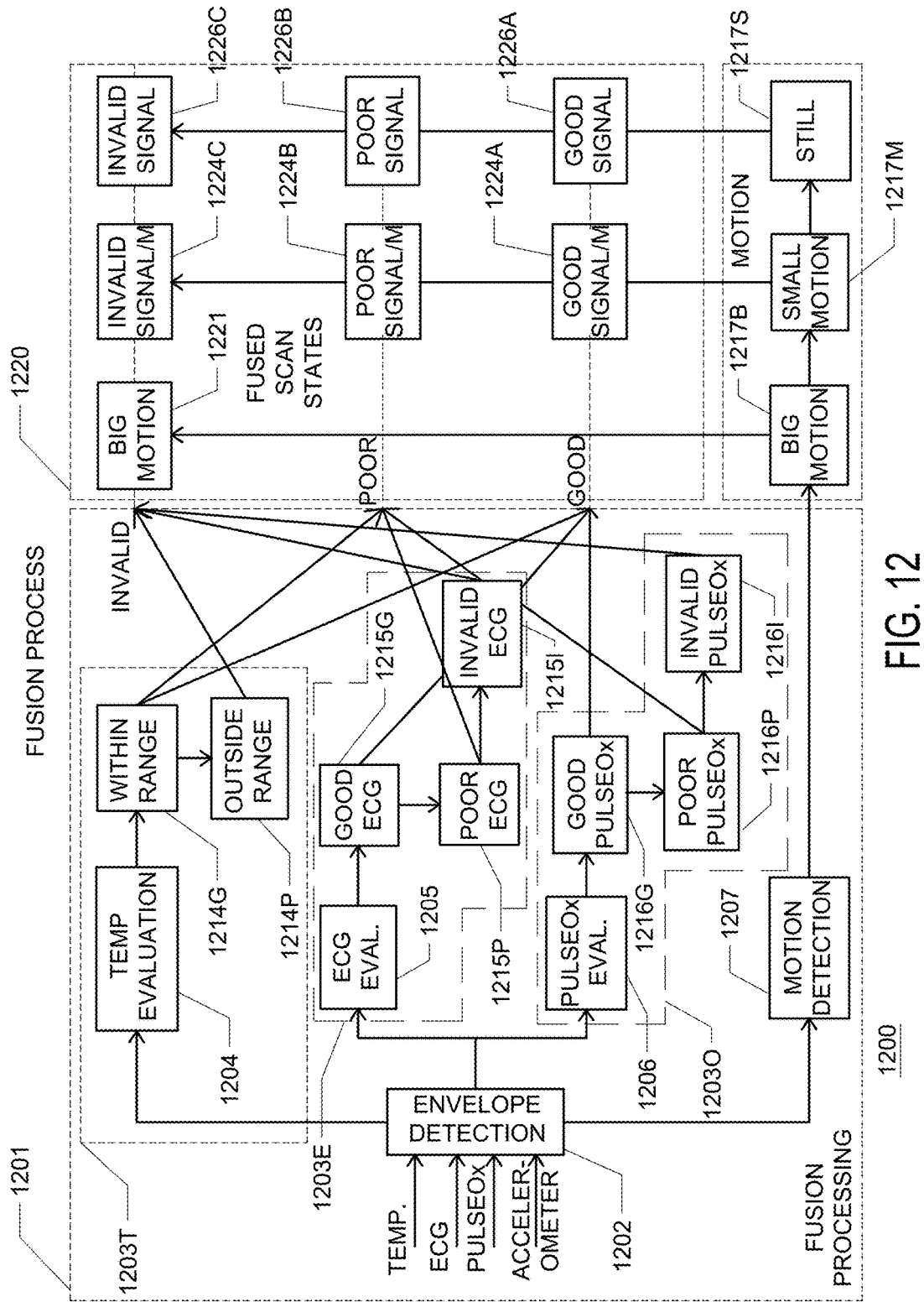
FIG. 12 illustrates a functional block diagram of the interactive scanning system.

Referring now to FIG. 12, a functional block diagram of an exemplary interactive vital signs scanning control system 1200 is illustrated. The vital signs scanning control system 1200 is a quick screening process before measurement are taken to decide in advance if a scan of vital signs data would be good, poor, or invalid. The screening process evaluates one or more short screening windows of time (e.g., WT1, WT2) to determine the quality of vital signs data that is being captured. The one or more short screening windows of time may be on the order of a second or two for example. Assuming a one second window and a sampling rate or frequency of 500 Hertz (Hz) or a two second window and a sampling frequency of 250 Hz, 500 data samples are used for the screening process. After the initial screening process provided by the interactive vital signs scanning control system 1200 determines that good signal data is being captured, a valid vital signs data capture occurs with the vital signs scanner. The data samples in the one or more short screening windows of time may be shared or overlap with the valid vital signs data capture if good signal data is being captured.

The vital signs scanning control system 1200 is executed by the vital signs scanner 102 in communication with the portable wireless device 104 (e.g., a smartphone). The vital signs scanning control system 1200 may be implemented in software, firmware, hardware, or a combination thereof. As mentioned herein, the vital signs scanning user interface 140 executed by the portable digital device 104 may be used to provide visual user feedback through the touchscreen display device 202 and audible user feedback through its speaker 216. Alternatively or additionally, the audio sound generator 847 of the vital signs scanner 102 may also be used to provide audible user feedback.

The vital signs scanning control system 1200 includes a sensor data fusion process 1201, and a scan state machine 1220 coupled in communication together. Data samples from the ECG sensor, the pulse oximeter sensor, and the accelerometer are received by the vital signs scanning control system 1200. Data samples from the ECG sensor are used in an ECG data evaluation process 1203E in the sensor data fusion process 1201. Data samples from the pulse-oximeter are used in a PulseOx data evaluation process 1203O in the sensor data fusion process 1201. Data samples from the accelerometer are used in a motion detection process 1207 in the sensor data fusion process 1201. Data samples from the temperature sensor may optionally be used in a temperature data evaluation process 1203T in the sensor data fusion process 1201.

The fusion process 1201 combines or fuses together the results of the ECG data evaluation process 1203E and the PulseOx data evaluation process 1203O to determine good, poor, or invalid scan signal data for each. The results of temperature data evaluation process 1203T may also be combined or fused together with that of the ECG data evaluation process 1203E and the PulseOx data evaluation process 1203O. As further described herein, the results may be logically fused together to determine good, poor, or invalid scan signal data.

The vital signs scanning control system 1200 further fuses together the results of the motion detection process 1207 with the ECG data evaluation process 1203E, the PulseOx data evaluation process 1203O, and optionally the temperature data evaluation process 1203T through the use of a state machine 1220.

The vital signs scanning control system may perform a signal processing technique of envelope detection 1202 upon the data samples associated with ECG, pulse oximeter, accelerometer, and optionally temperature. Envelope detection can be used to determine signal quality without having to analyze the content details of the signals. Envelope detection helps to remove signal variations of high frequency. While envelope detection and other techniques and processes are described herein, other known signal processing techniques may be used by the one or more embodiments of the invention to implement the data quality screening process. For example, a mean value may be subtracted from a sensor signal that may reach full range/scale or maximum amplitude values (e.g., digital 8 bit signal with 256 maximum value), for simpler processing. For example, a constant of 128 (256/2) may be subtracted from the signal value at each time step to reduce the signal range after forming an absolute value to be between 0 and a maximum value of 128. For motion detection, a mean constant of one (1) g may be subtracted from values generated by the accelerometer. After subtracting the mean value, envelope detection may be performed.

One method of implementing envelope detection is to apply a mathematical function to the input signals and then a low pass filter on the resultant mathematical signal output to form a portion of an envelope curve so that the envelope data can be further evaluated. A Hilbert Transform method of envelope detection may alternatively be used. After performing envelope detection 1202, the interactive vital signs scanning control system then performs various evaluations 1204-1207 on the detected envelope curves.

Generally, the system performs a temperature evaluation 1204 upon the temperature envelope curve. The system performs an ECG evaluation 1205 on the ECG envelope curve. The system also performs a pulse oximeter evaluation 1206 on the pulse oximeter envelope curve. The system further performs a motion detection 1207 upon the acceleration envelope curve. The system then makes a determination of the quality of the evaluations made of each envelope curve. The determination of the quality of the vital signs data may be made based upon a range of expected data, based upon an expected curve, or based upon one or more threshold numbers. Other known methods of determining the quality of the vital signs data may be used. Exemplary methods of how to determine the quality of the vital signs data are now described.

Figure 13A:
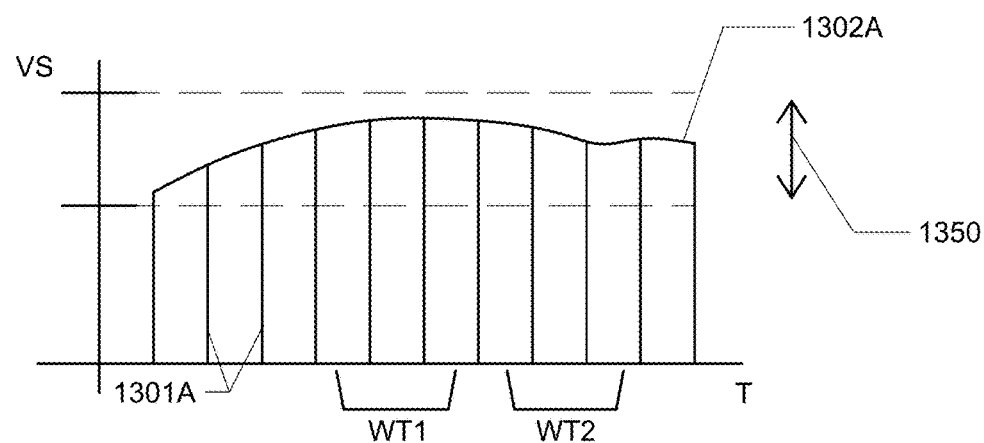
FIGS. 13A-13B illustrates exemplary graphs of determining quality of vital signs data within an expected range.
Figure 13B:
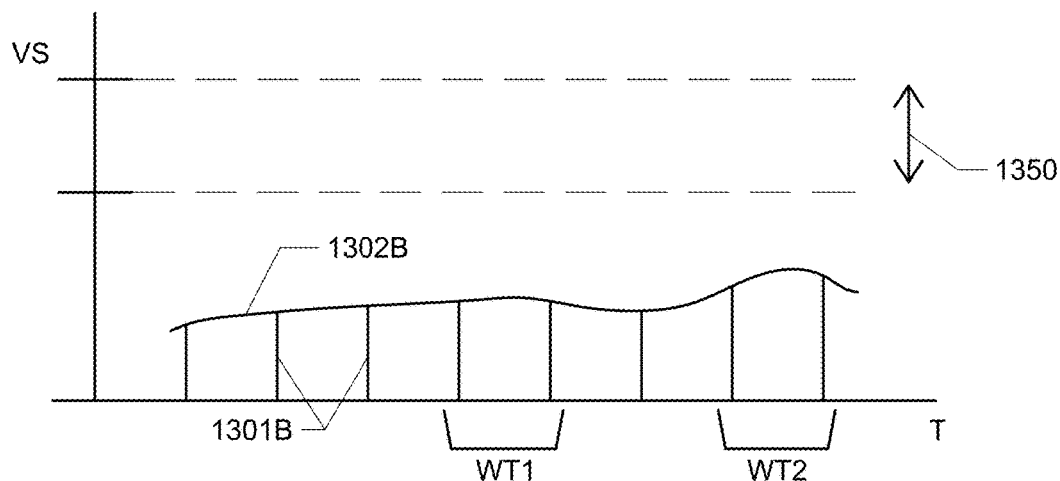

Referring now to FIGS. 13A-13B, the quality of a vital sign VS is determined using an expected range 1350. In FIG. 13A, data samples 1301A of the vital sign VS captured by the vital signs scanner 102 are plotted against an axis of time T or data sample number. The data samples 1301A undergo envelope detection to generate an envelope curve 1302A of measured data. The envelope curve 1302A is compared with the expected range 1350. If the envelope curve 1302A over a given period of time (e.g., time windows WT1,WT2) is within the expected range 1350, then the vital sign is determined to be within range 1214G. For example, an expected temperature range may be between 80 and 115 degrees Fahrenheit. An envelope curve for temperature measurement within this expected range would be deemed within temperature range 1214G.

In FIG. 13B, data samples 1301B of the vital sign VS are plotted against the axis of time T. The expected range 1350 remains the same. However, the envelope detection 1202 generates an envelope curve 1302B of measured data. In this case, the envelope curve 1302B over a period of time (e.g., time windows WT1,WT2) is outside the expected range 1350. In which case, the quality of the vital sign VS is determined to be outside range 1214P. Consider for example, the same expected temperature range between 80 and 115 degrees Fahrenheit. An envelope curve for temperature measurement well below 80 degrees Fahrenheit, such as shown at time periods WT1,WT2 of FIG. 13B, would be unexpected and deemed outside temperature range 1214P.

When screening data samples of the vital signs scanner, it is desirable to quickly determine the quality. Thus, the sample size is somewhat small and does not lend itself to be properly aligned in time with an expected curve. An expected range may be used to determine quality of the vital sign data samples.

Referring now to FIGS. 14A-14B, the quality of a vital sign VS is determined using envelope detection and thresholds. In FIG. 14A, data samples 1401A of the vital sign VS captured by the vital signs scanner 102 over a window of time (a number of samples) are plotted against an axis of time T to form the curve 1410. The data samples 1401A undergo envelope detection to generate an envelope curve 1430 for the sampled data. In this case, intermediate data and its curve 1420 can be generated from the data samples 1401A of curve 1410 using a mathematical function. An exemplary mathematical function for intermediate data (ID) is $ID=\sqrt{(RD-EA)^2}$ where the difference between raw data samples (RD) 1401A and an expected average value (EA) 1412 is squared and then a square root is taken to determine an intermediate data value (ID) 1402A for the intermediate curve 1420. Squaring shifts half the energy of the signal to higher frequency and half towards zero frequency or direct current DC signal. A low pass filter may then be used to filter out high frequency energy to determine the envelope curve 1430. Down sampling may also be employed to assist in the generation of the envelope curve 1430 and its amplitude values of its data samples 1403A.

Referring now to FIG. 14B, after envelope detection, threshold levels 1460-1461 may be used to distinguish between good, poor and invalid signal quality in the vital signs sensor data. A poor threshold level 1461 and an invalid threshold level 1460 may be established to distinguish between good, poor and invalid signal quality. The levels may be established based on the expected range around an expected average.

In one embodiment, if the actual measurements are fully or substantially saturated, the signal quality is deemed invalid. Assuming an 8 bit amplitude signal, a maximum value is 256. Further assume that the expected average is 128. An invalid signal with full saturation would be the outside range of positive 128 and negative 128 around the expected average of 128. Assume that a range within positive 50 and negative 50 around the expected average of 128 to be good signal quality. Translating this example to the envelope curve, amplitude values between zero and 49 may be good signals, amplitude values between 50 and 127 may be poor signals, and amplitude values from 128 and above may be invalid signals. Accordingly, the poor threshold level 1461 would be set to 50 and the invalid threshold level set to 128, for example.

The data samples 1403A during time window WT1 are substantially at the invalid threshold level 1460, in some cases exceeding it. If the circuit generating these sample values was expected to generate signal levels well below a saturation level, then the quality of the signals being generated substantially at or above the saturation level may be deemed as having an invalid signal or data quality.

The data samples 1403C during time window WT3 are below the invalid threshold level 1460 and meet or exceed the poor threshold level 1461. Accordingly, the data samples 1403C during time window WT3 may be deemed having a poor signal or data quality.

The data samples 1403B during time window WT2 are below the poor threshold level 1461. A signal with data samples below the lower threshold level 1461 may be deemed to have a good signal or data quality.

In this manner, quality of initial scan data from vital sign sensors during an interactive screening process can be quantified into invalid, poor, or good signal data.

Regarding the Pulse oximeter sensor, the RED and IR output signals for its RED LED and IR LED are expected to be good signals because the controller is designed to control the current used by the RED and IR LEDs. In accordance with one aspect of the invention, the RED and IR output signals have a good dynamic range and avoid full signal saturation during normal measurements. Thus, the evaluation of invalid signal quality for pulse oximetry may be based on whether or not the actual signal measurements are fully saturated. If not fully or substantially saturated, the signal quality of the pulse oximeter sensor data is not invalid. If fully or substantially saturated, then the signal quality of the pulse oximeter sensor data may be deemed invalid. For poor signal quality of the pulse oximeter sensor data, the data samples may meet or exceed a lower poor threshold level but not the full saturation level. For good signal quality of pulse oximeter sensor data, the data samples may not meet or exceed both the lower poor threshold level and the full saturation level.

Similar to the Pulse oximeter, in accordance with one aspect of the invention, the ECG circuitry in the scanner is designed to output signals that have good dynamic range and avoid full saturation. Accordingly, the evaluation of invalid ECG data can be based on whether or not the actual measurements are fully saturated or substantially saturated. If not fully or substantially saturated, the signal quality of the ECG sensor data is not invalid. If fully or substantially saturated, then the signal quality of the ECG sensor data may be deemed invalid. For poor signal quality of the ECG sensor data, the data samples may meet or exceed a lower poor threshold level but not the full saturation level. For good signal quality of ECG sensor data, the data samples may not meet or exceed both the lower poor threshold level and the full saturation level.

Referring back to FIG. 12, other known methods may be used to quickly determine a quality of scan data (e.g., good, poor, or invalid scan signal data) that is being captured by each sensor. Regardless, the results of the evaluation processes 1203E and 1203O, and optionally the results of the temperature evaluation process 1203T, may be logically fused together to determine an overall quality of good, poor, or invalid scan signal data being captured by the vital signs scanner.

To determine overall that good signal data is being captured, a logical AND operation is performed ANDing together the conditions of good PulseOX 1216G and good ECG 1215G. Optionally, the condition of temperature within range 1214G may also be ANDed together with good PulseOX 1216G and good ECG 1215G to determine that good scan signal data is being obtained. For example, if all of temperature within range 1214G, good PulseOX 1216G, and good ECG 1215G are generated, then the overall scanned signal result is good. This overall result can then be fused together with the detected motion condition through the state machine 1220 to further refine the state and quality of scan signal data being captured by the vital signs scanner.

To determine overall that poor signal data is being captured, a logical OR operation is performed ORing together the conditions of poor PulseOX 1216P and poor ECG 1215P. Optionally, the condition of temperature within range 1214G may also be ANDed with the logic OR of the poor PulseOX 1216P and the poor ECG 1215P to determine that poor scan signal data is being obtained. Even though good temperature data may be scanned within temperature range 1214G, poor PulseOX 1216P or poor ECG 1215P due to the scanner being pressed too hard or too light, the overall scanned signal data result is poor. This overall result can then be fused together with the detected motion condition through the state machine 1220 to further refine the state and quality of scan signal data being captured by the vital signs scanner.

To determine overall that invalid signal data is being captured, a logical OR operation is performed ORing together the conditions of invalid PulseOX 1216I and invalid ECG 1215I. For example, if either invalid PulseOX 1216I or invalid ECG 1215I are generated or true, the overall scanned signal result is invalid. Optionally, the condition of temperature outside range 1214P may also be logically ORed together with invalid PulseOX 1216I and invalid ECG 1215I, to determine that invalid scan signal data is being obtained. In this case, if temperature outside range 1214P, invalid PulseOX 1216I, or invalid ECG 1215I are generated or true, the overall scanned signal result is invalid. The overall scan signal result can then be fused together with the detected motion condition through the state machine 1220 to further refine the state and quality of scan signal data being captured by the vital signs scanner.

After evaluation of the acceleration envelope curve by the motion detection process 1207, a condition 1217B,1217M, or 1217S of the detected motion can be assigned during the interactive scanning process. The detected motion conditions of the current scanning process include significant motion (big motion) 1217B, minor motion (small motion) 1217M, or no motion (still) 1217S.

The detected motion condition may be assigned based upon an analysis of the envelope curves for the overall acceleration of the scanner in comparison with normal gravity. If there is a significant change or difference in overall acceleration of the scanner in comparison with gravity in a window of time, then significant or big motion 1217B may be assigned. If there is a minor variation in overall acceleration of the scanner in comparison with gravity over a window of time, then the condition of minor motion 1217M may be assigned. If there is little difference in overall acceleration of the scanner in comparison with gravity over a window of time, e.g., a steady state, then still or no motion 1217S may be assigned.

The concurrent detected motion condition and the evaluation of each vital signs measurement for the given scanning session are combined together by a scan state machine 1220 to be a collaborative decision on the quality of the given scanning session. In response to the detected motion condition and the initial quality screening of vital signs data, the current interactive scanning process may be assigned a state within the scan state machine 1220. Evaluation of the audio sounds captured by the microphone of the scanner or portable device may also be considered in assigning a state for the scan state machine 1220.

If the detected motion condition is significant or big motion 1217B, none of the vital sign measurements are deemed accurate. The scan state machine 1220 may be assigned a scan state of significant motion 1221, regardless of the results of the sensor data quality screening.

If the detected motion condition is small or minor motion 1217M or no motion (still) 1217S, the vital sign data quality plays a role in determining the fused scan state of the scan state machine 1220. Methods of determining how the data quality states of good ECG data 1215G, poor ECG data 1215P, and invalid data ECG 1215I were previously described. Methods of determining how the data quality states of good PulseOX data 1216G, poor PulseOX data 1216P, and invalid PulseOX data 1216I were previously described. Methods of determining how the data quality states of within temperature range 1214G and outside temperature range 1214P were previously described.

If the detected motion condition is minor motion 1217M, the quality of the vital signs data can cause the scan state machine 1220 to have the states good signal with motion 1224A, poor signal with motion 1224B, or invalid signal with motion 1224C depending upon the screened quality of the vital sign data. If either the pulse oximeter data has a data quality state of invalid PulseOX data 1216I or the ECG data has a data quality state of invalid ECG data 1215I, then the scan state machine 1220 of the interactive scanning process may be assigned the scan state of invalid signal with motion 1224C. If the pulse oximeter data has a data quality state of poor PulseOX data 1216P, the ECG data has a data quality state of poor ECG data 1215P, or the temperature data has a data quality state of outside temperature range 1214P, then the scan state machine 1220 of the interactive scanning process may be assigned the scan state of poor signal with motion 1224B. If the pulse oximeter data has a data quality state of good PulseOX data 1216G, the ECG data has a data quality state of good ECG data 1215G, and the temperature data has a data quality state of within temperature range 1214G, then the scan state machine 1220 of the interactive scanning process may be assigned the scan state of good signal with motion 1224A.

If the detected motion condition is still or no motion 1217S, the quality of the vital signs data can cause the scan state machine 1220 to have the scan states of good signal 1226A, poor signal 1226B, or invalid signal 1226C. If either the pulse oximeter (PulseOX) data has a data quality state of invalid PulseOX data 1216I or the ECG data has a data quality state of invalid ECG data 1215I, then the scan state machine 1220 of the interactive scanning process may be assigned the scan state of invalid signal 1226C. If the pulse oximeter data has a data quality state of poor PulseOX data 1216P, the ECG data has a data quality state of poor ECG data 1215P, or the temperature data has a data quality state of outside temperature range 1214P, then the scan state machine 1220 of the interactive scanning process may be assigned the scan state of poor signal 1226B. If the pulse oximeter data has a data quality state of good PulseOX data 1216G, the ECG data has a data quality state of good ECG data 1215G, and the temperature data has a data quality state of within temperature range 1214G, then the scan state machine 1220 of the interactive scanning process may be assigned the scan state of good signal 1226A.

If the scan state machine 1220 reaches the scan state of good signal 1226A, the interactive scanning process continues with the data being evaluated and measures a plurality of vital signs data that is saved and delivered to the digital device 104 from the scanner 102. If any other state is assigned, user feedback may be generated to instruct the user on how to reach the good signal state 1226A.

Figure 15A:
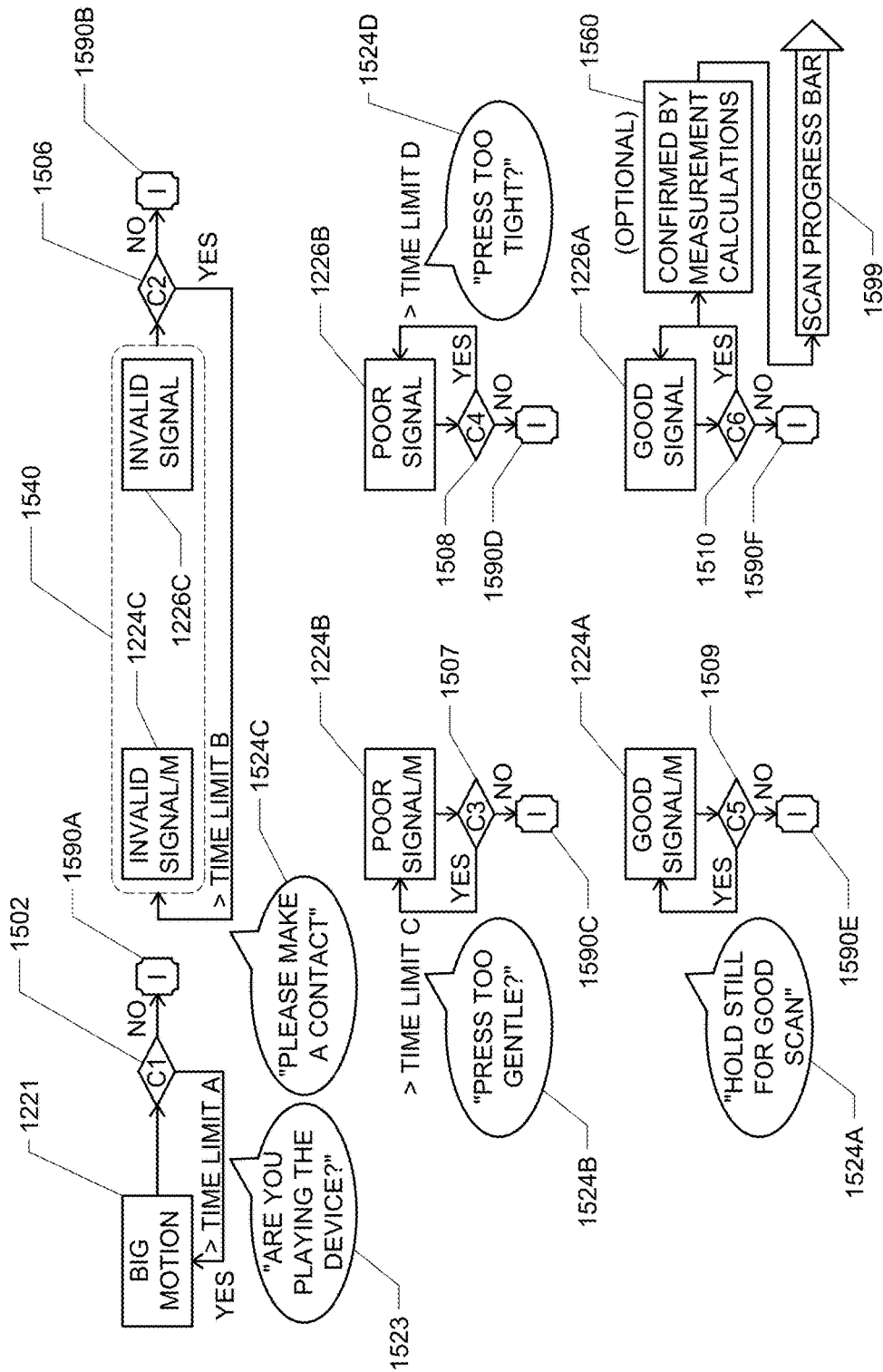
FIG. 15A illustrates a functional block diagram of the interactive scanning process and user feedback (feedback to the user from the scanner and/or portable wireless device) when remaining in the same scan state.
Figure 15B:
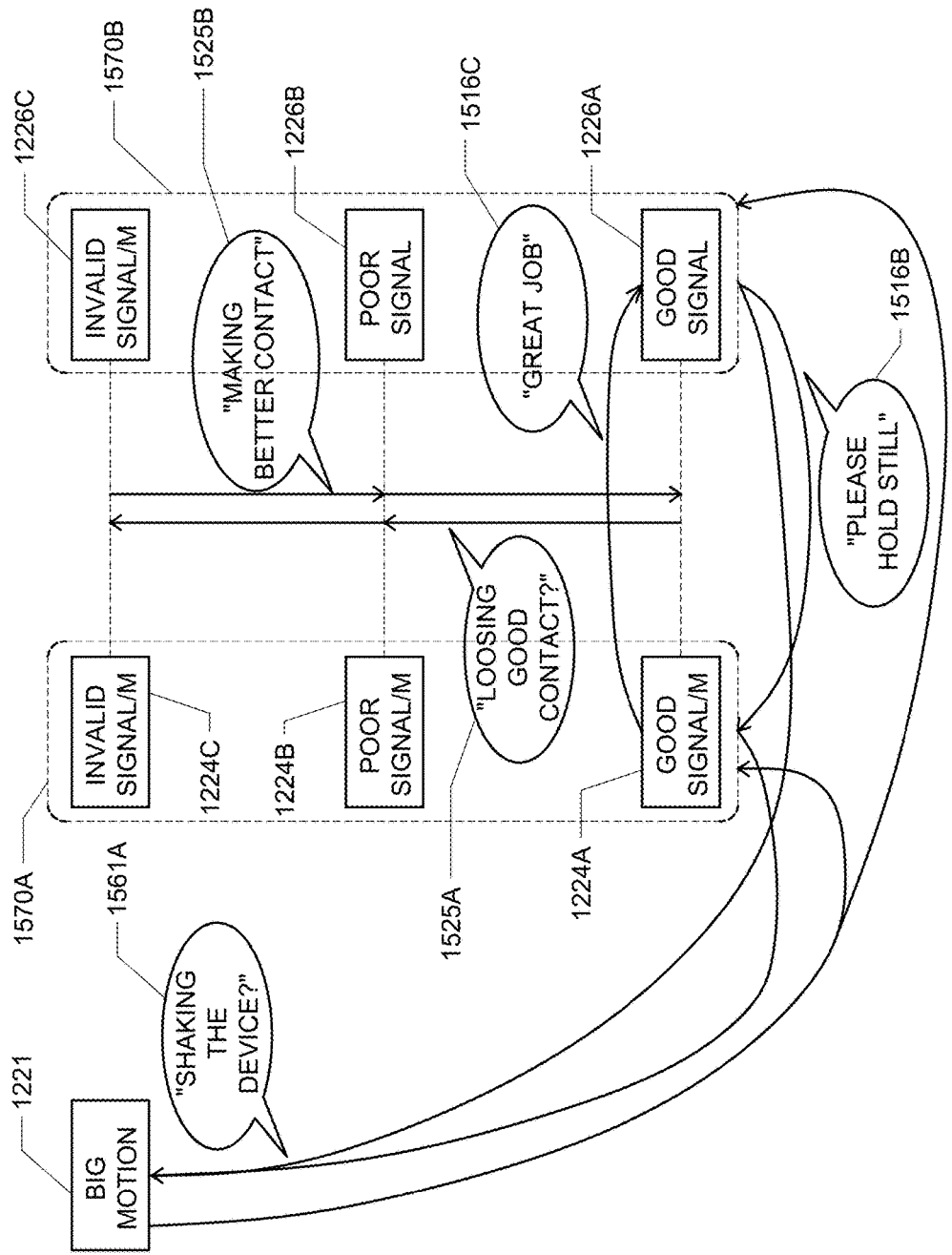
FIG. 15B illustrates a functional block diagram of the interactive scanning process and user feedback (feedback to the user from the scanner and/or portable wireless device) when transitioning to a different scan state.

Referring now to FIGS. 15A-15B, state diagrams for the scan state machine 1220 are illustrated to further explain the interactive scanning process provided by the portable vital signs scanner 102 and the vital signs scanning user interface 140. FIG. 15A illustrates the interactive scanning process, user feedback, and determinations made to maintain the same state. Previously the logic used to enter the states of the scan state machine 1220 was described in response to the quality of vital signs data and the motion detected of the scanner 102. If the quality of scan data changes or the motion condition changes, the state machine transitions from one scan state to another. FIG. 15B illustrates the interactive scanning process and the user feedback that may be generated during transitions between scan states.

An element of time (e.g., number of time windows, or a number of data samples) may be used by the state machines to determine if the scan state remains the same or transition to another states as the screening process continues. Furthermore, different user feedback may be generated in response to the scan state to interactively instruct the user on how to more properly use the scanner 102 and obtain better data quality. The scan state machine keeps track of the current scan state and the number of time windows over which the state machine has been in the current scan state. Time limits may be used in order to determine when to re-evaluate the current scan state (e.g., see determination blocks 1502,1506-1510 in FIG. 15A) and if a transition to another scan state should be made. If a transition to another scan state is made, the time window count of the current scan state is reinitialized (e.g., see initialization blocks 1590A-1590F in FIG. 15A), such as to zero. The state machine may further keep track of history of past scan states to make various decisions regarding the user feedback to be generated.

The scanning process is initiated by the user by pressing the scan button in the user interface 140 on the device 104. The scanner 102 is moved by the user towards his/her forehead/temple for the primary scan or his/her chest for the secondary scan. The accelerometer sensor senses the substantial motion made to position the scanner 102 against the user's body establishing a big motion condition 1217B. As the scanner 102 is pressed against the user's body, the motion detected by the accelerometer and the interactive scanning process over a time window may be reduced to the small motion condition 1217M or the no motion condition 1217S. With an initial motion condition of the big motion condition 1217B, the state of the scan state machine 1220 has a big motion scan state 1221 as its initial state.

Assume the state of the scan state machine 1220 is the big motion scan state 1221. After a first time limit A has been exceeded while in the big motion scan state 1221, a determination is made at process 1502 if the scan state continues to be the big motion scan state 1221. If yes, user feedback 1523 is generated asking the user if he/she is playing with the scanner. The counter is incremented to keep a current count of the number of time windows the state machine remains in the big motion scan state 1221. If the scan state is no longer in the big motion scan state 1221, the counter is cleared or reinitialized by the initialization block 1590A. The scan state may no longer be in the big motion scan state 1221 if the accelerometer sensor no longer senses big motion. The scan state machine goes to a different scan state in response to the fused scan data quality and the motion condition.

The invalid signal with motion state 1224C and the invalid signal state 1226C form an invalid super state 1540. Assume the scan state is in the invalid super state 1540 of either the invalid signal with motion state 1224C or the invalid signal state 1226C. Next at process 1506, after a second time limit B has been exceeded while in the super state 1540, a determination is made if the fused scan data quality and motion condition continues to form the invalid super state 1540. If yes, user feedback 1524C is generated asking the user to please make contact with the scanner. The counter is incremented to keep a current count of the number of time windows the state machine remains in the invalid super state 1540. If the scan state is no longer in the invalid super state 1540, the counter is cleared or reinitialized by the initialization block 1590B. The scan state may no longer be in the invalid super state 1540 if a better scan data quality is determined by the screening process. For example, the scan state machine may go to a poor signal with motion state 1224B or a poor signal state 1226B. Alternatively, with still better scan data quality, the scan state machine may go to a good signal with motion state 1224A or a good signal state 1226A.

Assume the scan state machine is in the poor signal with motion state 1224B. At process 1507, after a third time limit C has been exceeded while in the poor signal with motion state 1224B, a determination is made if the fused scan data quality and motion condition continues to form the poor signal with motion state 1224B. If yes, user feedback 1524B is generated asking the user if he is pressing too gently in order to prompt him to press harder to make better contact. The counter is incremented to keep a current count of the number of time windows the state machine remains in the poor signal with motion state 1224B. If the scan state is no longer in the poor signal with motion state 1224B, the counter is cleared or reinitialized by the initialization block 1590C. The scan state may no longer be in the poor signal with motion state 1224B if either the accelerometer sensor no longer senses small motion and the scan state machine goes to the poor signal state 1226B in response to the change in the motion condition or to a different scan signal state in response to a better scan data quality or worse can data quality. For example, the scan state machine may go to a poor signal state 1226B if motion condition goes to a still or no motion condition 1217S. With better scan data quality, the scan state machine may go to a good signal with motion state 1224A or a good signal state 1226A if the motion condition also changes to the no motion condition 1217S. With poorer scan data quality, the scan state machine may go to the invalid signal with motion state 1224C or the invalid signal state 1226C if the motion condition also changes to the no motion condition 1217S.

Assume the scan state machine is in the poor signal state 1226B. At process 1508, after a fourth time limit D has been exceeded while in the poor signal state 1226B, a determination is made if the fused scan data quality and motion condition continues to form the poor signal state 1226B. If yes, user feedback 1524D is generated asking the user if he is pressing too tight in order to prompt him to press less hard to make a better contact. The counter is incremented to keep a current count of the number of time windows the state machine remains in the poor signal state 1226B. If the scan state is no longer in the poor signal state 1226B, the counter is cleared or reinitialized by the initialization block 1590D. The scan state may no longer be in the poor signal state 1226B, if the accelerometer sensor no longer senses absence of motion and either the scan state machine goes to the poor signal with motion state 1224B in response to the change in the motion condition, or the scan state machine goes to a different scan signal state in response to a better or worse can data quality. For example, the scan state machine may go to a poor signal with motion state 1224B if motion condition goes to a small or minor motion condition 1217M. With better scan data quality, the scan state machine may go to a good signal state 1226A or a good signal with motion state 1224A if the motion condition also changes to the minor motion condition 1217M. With poorer scan data quality, the scan state machine may go to the invalid signal state 1226C or the invalid signal with motion state 1224C if the motion condition also changes to the minor motion condition 1217M.

Assume the scan state machine is in the good signal with motion state 1224A. At process 1509, after a fifth time limit E has been exceeded while in the good signal with motion state 1224B, a determination is made if the fused scan data quality and motion condition continues to form the good signal with motion state 1224A. If yes, user feedback 1524A is generated asking the user to hold still for a good scan. The counter is incremented to keep a current count of the number of time windows the state machine remains in the good signal with motion state 1224A. If the scan state is no longer in the good signal with motion state 1224A, the counter is cleared or reinitialized by the initialization block 1590E. The scan state may no longer be in the good signal with motion state 1224A if either the accelerometer sensor no longer senses small motion and the scan state machine goes to the good signal state 1226A in response to the change in the motion condition or to a different scan signal state in response to worse scan data quality. For example, the scan state machine may go to a good signal state 1226A if the motion condition goes to a still or no motion condition 1217S. With poorer scan data quality, the scan state machine may go to the poor signal with motion state 1224B or the poor signal state 1226B, or the invalid super state 1540.

Assume the scan state machine is in the good signal state 1226A. At process 1510, a determination is made if the fused scan data quality and motion condition continues to form the good signal state 1226A. If yes, user feedback may be generated in the form of a scan progress bar 1599 or otherwise inform the user that good scan data quality is being achieved. The counter is incremented to keep a current count of the number of time windows the state machine remains in the good signal state 1226A. If the scan state is no longer in the good signal state 1226A, the counter is cleared or reinitialized by the initialization block 1590F. The scan state may no longer be in the good signal state 1226A if the accelerometer sensor no longer senses absence of motion and the scan state machine goes to the good signal with motion state 1224A in response to the change in the motion condition. The scan state may no longer be in the good signal state 1226A in response to a poorer can data quality. For example, the scan state machine may go to the poor signal state 1226B, the poor signal with motion state 1224B, or the invalid signal supper state 1540.

Referring now to FIG. 15B, user feedback (positive user feedback or negative user feedback) may be generated and presented to a user as the scan data quality causes a transition between scan signal states or the motion condition changes to cause a transition between scan signal states. As mentioned previously, audible user feedback may be generated by a speaker or audible generator in the scanner 102 or the device 104. Visual user feedback may be generated by the user interface 140 on the display of the device 104.

Scan signal states 1224A-1224C associated with the minor motion condition 1217M may be collectively referred to as a minor motion super state 1570A. Scan signal states 1226A-1226C associated with the still motion condition 1217S may be collectively referred to as a no motion super state 1570B.

User feedback may be generated and presented to a user as a change in the motion condition causes a transition between scan states. The occurrence of big motion 1217B can result in a jump to the big motion scan state 1221 from either the minor motion super state 1570A or the no motion super state 1570B. User feedback 1516A may be generated asking the user audibly and/or visually if he/she is shaking the scanner 102.

If the scan state is one of the no motion super states 1570B and if motion is detected by the accelerometer over a time window such that the interactive scanning process reverts back to one of the scan states in the minor motion super states 1570A, user feedback 1516B may be generated. The user feedback 1516B may be presented to the user audibly and/or visually asking him/her to please hold still.

If in the good signal with motion scan state 1224A, the motion detected by the accelerometer and the interactive scanning process over a time window is substantially reduced to still or no motion, the scan state may transition to the good scan state 1226A. In this case, user feedback 1516C may be generated during the transition providing positive user feedback, such as great job, and presented to the user audibly or visually on the display device 202 of the device 104.

In FIG. 15B, user feedback may be generated and presented to a user as the scan data quality causes a transition between scan signal states. For example, a transition from either the invalid signal with motion state 1224C or the invalid signal state 1226C to a better level of scan data quality and scan state, positive user feedback 1525B may be generated and inform the user that he/she is making better contact to reinforce the improvement. On the other hand, a transition from either the good signal with motion state 1224A or the good signal state 1226A to a poorer level of scan data quality and scan state, negative user feedback 1525A may be generated and inform the user that he/she is losing good contact with the scanner 102 to alter the behavior of the user.

Referring now back momentarily to FIG. 15A, if the vital signs control system goes to the good signal state 1226A, then the scanning process can continue and start making measurement calculations for the vital signs. Some of the data in the screening process if of good quality may be used to perform the calculation. If not, added time is used to obtain the needed data to perform the calculations. In the good signal state 1226A, user feedback 1599 is generated by displaying a scan progress bar to user, for example. While in the good signal state 1226A, the scan state is continuously revaluated by the state machine 1220. For example if small motion 1217M or big motion 1217B are detected, measurement calculations may be paused due to a transition away from the good signal state 1226A. The scan states may revert to states other than the good signal state 1226A. In which case, the scan progress bar 1599 is interrupted and additional user feedback may be provided on how to continue or restart the scanning process. For example, the scan progress bar 1599 may be reset if the scanning process is restarted from the beginning.

Referring now back momentarily to FIG. 15A, before measurement calculations are presented to the user, the scan quality may optionally be confirmed at block 1560 of the interactive scanning process. If the scan quality cannot be confirmed, the scan progress bar may be interrupted and additional user feedback may be provided on how to continue or restart the scanning process. For example, the scan progress bar 1599 may be reset if the scanning process is restarted from the beginning.

Scan quality can be confirmed by performing additional measurement calculations. Alternatively or additionally, scan quality can be confirmed by using multiple time windows. The multiple time windows may be fused together to confirm that the scan data is really good by measuring the scan data against expected curve. An element of time is aligned between the scan data curve and an expected curve. Time alignment between curves is possible for both ECG and PPG curves because the shape and peaks of the curves are distinct and can be detected, for example, by match filtering.

Referring now to FIGS. 17A-17C, the quality of a vital sign VS measurement calculations that were made can be confirmed using an expected curve 1750. In FIG. 17A, data samples 1701A of the vital sign VS captured by the vital signs scanner 102 are plotted against an axis of time T. The data samples 1701A undergo envelope detection to generate an envelope curve 1702A of measured data. The envelope curve 1702A is compared with the expected curve 1750. If the pattern of the envelope curve 1702A over a given period of time matches the pattern of the expected curve 1750, then the good quality of the vital sign is confirmed.

In FIG. 17B, data samples 1701B of the vital sign VS captured by the vital signs scanner 102 are plotted against an axis of time T. The data samples 1701B undergo envelope detection to generate an envelope curve 1702B of measured data. The envelope curve 1702B of the vital sign is compared with the expected curve 1750. If the pattern of the envelope curve 1702B over a given period of time does not match the pattern of the expected curve 1750, then the good quality of the vital sign is not confirmed.

In FIG. 17C, data samples 1701C of the vital sign VS captured by the vital signs scanner 102 are plotted against an axis of time T. The data samples 1701C undergo envelope detection in an attempt to generate an envelope curve 1702C of measured data. The envelope curve 1702C of the vital sign is compared with the expected curve 1750. If the pattern of the envelope curve 1702C over a given period of time has no bearing whatsoever to the expected curve 1750, then again the good quality of the vital sign is not confirmed.

The quality of the sensor data for the ECG sensor and the quality of the sensor data for the pulse oximeter sensor may both be determined by comparing against expected curves.

If the pattern of the envelope curve of the sensor data for the ECG sensor over a given period of time matches the pattern of an expected ECG curve, then the quality of the ECG data for the ECG vital sign is confirmed to be good. If the pattern of the envelope curve of the sensor data for the ECG sensor over a given period of time does not match the pattern of the expected ECG curve, then the good quality of the of the ECG data is not confirmed. If the pattern of the envelope curve of the sensor data for the ECG sensor over a given period of time has no bearing whatsoever to the expected ECG curve, then a good quality of the of the ECG data for the vital sign is not confirmed.

If the pattern of the envelope curve of the sensor data for the pulse oximeter sensor over a given period of time matches the pattern of an expected pulse oximeter curve, then the quality of the pulse oximeter data for a vital sign is confirmed to be good. If the pattern of the envelope curve of the sensor data for the pulse oximeter sensor over a given period of time does not match the pattern of the expected pulse oximeter curve, then a good quality of the of the pulse oximeter data for the vital signs is not confirmed. If the pattern of the envelope curve of the sensor data for the pulse oximeter sensor over a given period of time has no bearing whatsoever to the expected pulse oximeter curve, then a good quality of the of the pulse oximeter sensor data for the vital signs is not confirmed.

If the measurement calculations are optionally confirmed at block 1560 during the interactive scanning process, the measurement calculations may be presented to the user.

Sensor Data Fusion for Improved Vital Signs Measurements

While user feedback may be used during an interactive scanning process to improve scan quality, the plurality of different types of vital signs data may also be used to improve the data quality by combining or fusing data together.

Figure 16:
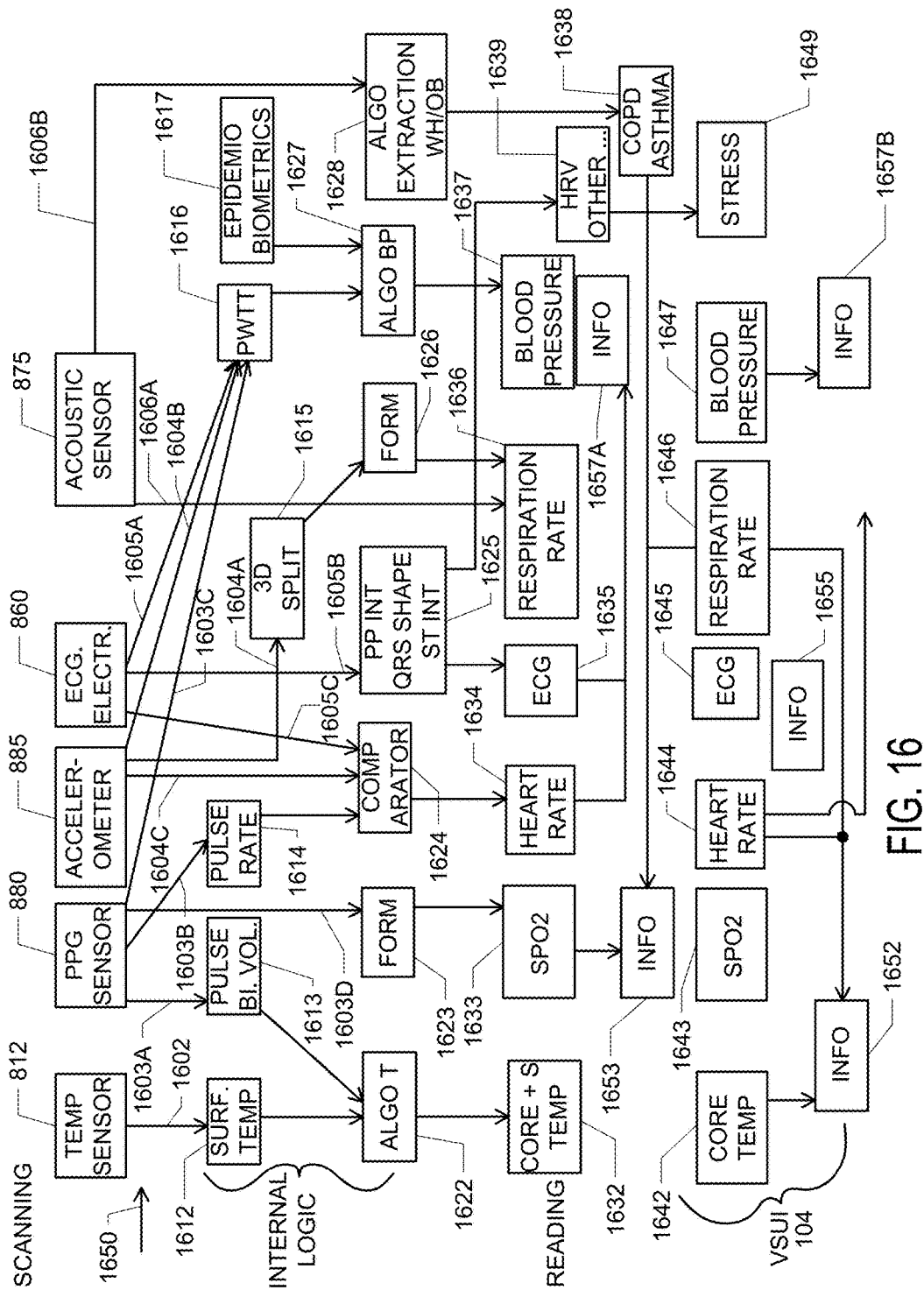
FIG. 16 illustrates a functional block diagram of the methods of data fusion for improving vital sign measurement quality.

Referring now to FIG. 16, a flow chart of methods including sensor data fusion to improve vital sign measurements is illustrated. The vital signs scanner 120 integrates a plurality of vital sign sensors 812, 880, 885, 860, 875 into a low cost finger held device. The plurality of vital signs sensors concurrently sense data over one or more periods of time generating sensor data 1650 associated with vital signs of a human body. The sensor data 1650 includes sensed data 1602, 1603A-1603D, 1604A-1604C, 1605A-1605C, 1606A-1606B from each of the respective vital signs sensors 812, 880, 885, 860, 875.

The sensed data 1602, 1603A-1603D, 1604A-1604C, 1605A-1605C, 1606A-1606B from each of the respective vital signs sensors 812, 880, 885, 860, 875 is used to concurrently determine a plurality of vital signs values for a respective plurality of vital signs for a given time and date. Internal logic within the vital signs scanner 120 generates values for vital signs such as surface temperature 1612, pulse blood volume 1613, and pulse rate 1614, for example.

As the vital sign data is concurrently determined from each sensor, they are related by time and date. There may be a further relatedness between two or more sensed data types or two or more vital sign values. This relatedness may be exploited by fusing together two or more types of sensed data or two or more vital sign values together to improve accuracy/quality or to form a new, different, or related vital sign.

For example, PPG sensor data 1603C, accelerometer data of the chest area, and ECG sensor data 1605 may be fused together to determine pulse wave transit time (PWTT) 1616 that is directly related to blood pressure. PWTT can also be calculated non-invasively from ECG sensor data and SpO2 sensor data. The technology employed for blood pressure measurement may be based on the PWTT technology described in U.S. Pat. No. 5,564,427 filed by Aso et al. incorporated herein by reference. The PWTT technology described in U.S. Pat. No. 5,564,427 may be modified to improve PWTT measurements. 42

The precision of a PWTT measurement may be enhanced by particular methods of cross-correlation. Additionally, epidemio biometrics (user biometrics) 1617 may also be fused together with the PWTT data 1616 (derived from accelerometer data, ECG data, and PPG sensor data) by a blood pressure algorithm 1627. For example, one or more of a user's biometrics of age, height, and weight (user biometrics) may be fused together with the PWTT data 1616 to determine blood pressure. Large scale curated datasets or databases of hypertension may be fused along with the blood pressure. Likewise temperature may be used as an additional input in order to enhance the accuracy of both systolic and diastolic blood pressure measurements.

Two or more vital sign values of different vital signs may be fused together by mathematical algorithms to improve the accuracy or quality of the values of the one or more vital signs. Alternatively, two or more vital sign values may be fused together by mathematical algorithms to form a value for a new and different vital sign for which data is not sensed. For example, surface body temperature 1612 sensed by the infrared thermometer sensor 812 may be fused together with pulse blood volume 1613 sensed by the PPG sensor 880.

Knowing the volume of blood at a core temperature that enters the microcirculation under a probed region, and knowing the external surface body temperature, the value of core temperature Tcore can be obtained. Internal core temperature can be computed if the ambient temperature and the Skin surface temperature are known both of which we get from the Melexis sensor. Heat flux q passes from the core temp ($T_c$) through the skin to the ambient environment ($T_a$) where the skin surface temp ($T_s$) is held at some intermediary temp between core and ambient temp. An equation for core temperature is $T_c=(h/pc)(T_s-T_a)+T_s$ where h/pc is a weighting coefficient that weights the difference in skin surface and ambient temperature and is determined empirically on a statistical basis over different patients and different clinical situations.

In this manner, the surface body temperature and the pulse blood volume may be fused together by the temperature algorithm 1622 to determine core body temperature as well as improve the surface temperature 1632. U.S. Pat. No. 7,787,938 issued to Franceso Pompei on Aug. 31, 2010 describes further details of determining temperature in this manner and is incorporated by reference.

Acceleration data (motion) 1604A from the accelerometer 885 and acoustic sensor data 1606A from the stereo microphone 875 may also be fused together by mathematical algorithms, with or without the vital sign values from the vital sign sensors, to improve the accuracy or quality of vital sign values or form a value for a different vital sign. For example, a fusion formula 1626 may be used to fuse acoustic sensor data 1606A and an axis of acceleration data to determine respiration rate 1636. A 3D splitter 1615 splits up three axes of data from a tri-axis accelerometer 885.

The formula 1623 that may be used to convert PPG sensor data 1603A-1603D into SPO2 data 1633 is described for example in "Pulse Oximetry: Theory and Applications for Noninvasive Monitoring" by Yitzhak Mendelson, CLIN. CHEM. 38/9, 1601-1607 (1992); and Noninvasive Pulse Oximetry Utilizing Skin Reflectance Photoplethysmogmphy" by Yitzhak Mendelson and Burt D. Ochs, IEEE Trans. On Biomedical Engineering, Vol. 35, No. 10, October 1988, pages 798-805.

A comparator formula 1624 can fuse pulse rate 1614, accelerometer data 1604, and ECG sensor data 1605 together to obtain heart rate information 1634. Electrocardiogram (ECG) data 1605 can be further evaluated with formulas 1625 to obtain the PR interval, the QRS shape, the ST interval, and more ECG information 1635 that is used to determine heart activity. This ECG information can be further processed by algorithms 1639 to determine heart rate variability (HRV), the variation in the time interval between heartbeats, or other conditions of a users heart, as well as stress 1649.

One or more algorithms 1628 may be used to extract sound signals from well defined frequency bands relative to wheezing and murmurs. Wheezings and murmurs have very different pitches and can be easily separated on a frequency basis, even without their full spectral envelopes. The extracted sounds of wheezings and murmurs may be used diagnose chronic obstructive pulmonary disease (COPD) or asthma 1638.

The vital signs user interface (VSUI) 140 can be used to store and present much of the vital signs data to a user including core temperature 1642, SPO2 data 1643, heart rate 1644, ECG data 1645, respiration rate 1646, blood pressure 1647, and stress levels 1649.

Additional information may be requested by the user by using the vital signs user interface (VSUI) through information requests 1643, 1652, and 1657A-1657B to better diagnose a condition.

CONCLUSION

Various specific materials, designs, dimensions, etc. are provided and are considered highly beneficial embodiments of the present disclosure in one regard. However, in other regard, such specifics are also merely illustrative of broader aspects of the present disclosure and should not be considered to necessarily limit to such broader aspects unless expressly specified to be required. In particular, the various specific dimensions provided as such examples are intended to be about any particular values provided, with typical tolerances and ranges of suitable alternatives as would be apparent to one of ordinary skill. Where particular combinations of such dimensions are provided for exemplary illustration of certain embodiments, the relative relationships between them are also contemplated as having been herein disclosed as additional beneficial aspects (even if the specific values of the relative dimensions change). For example, certain lengths, widths, and/or depths of particular components shown and described for a particular assembly provide overall geometries which may be varied by changing certain sub-sets of such dimensions, but may also be fixed relative to the ratios of these values despite the valued changing (so long as their general relationship remains). Similarly, such dimensions of different component parts also have similar relative relationships which are similarly contemplated, also as apparent to one of ordinary skill.

When implemented in software, the elements of the embodiments of the invention are essentially the code segments or instructions to perform the functional tasks described herein. The code segments or instructions are executable by a processor, such as processor 206, 840, and can be stored in a storage device or a processor readable storage medium, such as memory 208, 841, awaiting execution. The processor readable storage medium may include any medium that can store information. Examples of the processor readable storage medium include an electronic circuit, a semiconductor memory device, a read only memory (ROM), a flash memory, an erasable programmable read only memory (EPROM), a floppy diskette, a CD-ROM, an optical disk, a hard disk. The code segments or instructions may be downloaded via computer networks such as the Internet, Intranet, etc. into the processor readable storage medium.

Various combinations and sub-combinations, and modifications as may be made, of the presently disclosed components and embodiments and aspects are contemplated whether or not specifically disclosed hereunder, to the extent and as would be apparent to one of ordinary skill based upon review of this disclosure and in order to suit a particular intended purpose or application.

While certain embodiments of the disclosure have been described, these embodiments have been presented by way of example only, and are not intended to limit the scope of the disclosure. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by patented claims that follow below.

What is claimed is:

1. A method comprising:
concurrently scanning for a plurality of vital signs with a plurality of sensors of a portable vital signs scanner to generate vital signs scan data;
detecting movement with an accelerometer of the portable vital signs scanner during the scanning for the plurality of vital signs;
generating first scan data from the vital signs scan data, the first scan data comprising a first category of health status information;
based upon the first scan data, selecting a first scan state from a set of stored scan states;
tracking a number of time windows for the first scan state, the time windows being for measuring a quality of the vital signs scan data;
comparing the first scan data to a stored predetermined range for the first category of health information to generate a scan comparison; and
in response to the scan comparison and the detected movement, determining a measure of quality of the vital signs scan data.

2. The method of claim 1, further comprising:
generating user feedback to present to a user in response to the determined measure of quality of the concurrent scan for the plurality of vital signs.

3. The method of claim 1, further comprising:
generating user feedback to present to a user in response to determining an invalid or unreliable measure of quality of the concurrent scan for the plurality of vital signs.

4. The method of claim 1, further comprising:
generating user feedback to present to a user in response to determining a reliable measure of quality of the concurrent scan for the plurality of vital signs and minor movement of the portable vital signs scanner.

5. The method of claim 1, further comprising:
generating user feedback to present to a user in response to determining significant movement of the portable vital signs scanner, regardless of the measure of quality of the concurrent scan for the plurality of vital signs.

6. The method of claim 1, further comprising:
generating user feedback to present to a user in response to repeatedly determining a reliable measure of quality of the concurrent scan for the plurality of vital signs without movement of the portable vital signs scanner.

7. The method of claim 6, wherein
the measure of quality of the scan for the plurality of vital signs during the period of time is reliable if the scan data for a pulse oximeter vital sign and the scan data for an electrocardiogram (ECG) vital sign is evaluated to be reliable scan data.

8. The method of claim 6, wherein
the measure of quality of the scan for the plurality of vital signs during the period of time is reliable if the scan data for a pulse oximeter vital sign is evaluated to be reliable scan data, the scan data for an electrocardiogram (ECG) vital sign is evaluated to be reliable scan data, and if scan data for a temperature vital sign is within an expected range.

9. The method of claim 6, wherein
the user feedback that is generated is a scan progress bar that is filled in as a fraction of progress is made in generating measurements for the plurality of vital signs.

10. The method of claim 9, wherein
the fraction is each tenth of progress made in generating measurements for the plurality of vital signs.

11. The method of claim 9, wherein
during a second period of time, the measure of quality of the scan for the plurality of vital signs becomes unreliable; and
the scan progress bar is paused or reset in response to the unreliable measure of scan quality.

12. The method of claim 3, wherein
the measure of quality of the scan for the plurality of vital signs during the period of time is unreliable if either the scan data for a pulse oximeter vital sign or the scan data for an electrocardiogram (ECG) vital sign is evaluated to be unreliable scan data.

13. The method of claim 3, wherein
the measure of quality of the scan for the plurality of vital signs during the period of time is unreliable if scan data for a temperature vital sign is within an expected range and either the scan data for a pulse oximeter vital sign is evaluated to be unreliable scan data or the scan data for an electrocardiogram (ECG) vital sign is evaluated to be unreliable scan data.

14. The method of claim 2, further comprising:
determining that significant motion of the portable vital signs scanner was detected during a period of time; and
wherein the user feedback is generated to inquire of a user if he is playing with the portable vital signs scanner.

15. The method of claim 2, further comprising:
determining that the measure of quality of the scan for the plurality of vital signs during a period of time is invalid; and
wherein the user feedback is generated to instruct a user to make contact with the portable vital signs scanner to the user's body.

16. The method of claim 15, wherein
the measure of quality of the of the scan for the plurality of vital signs during the period of time is invalid if either scan data for a pulse oximeter vital sign or scan data for an electrocardiogram (ECG) vital sign is evaluated to be invalid scan data.

17. The method of claim 15, wherein
the measure of quality of the scan for the plurality of vital signs during the period of time is invalid if either scan data for a pulse oximeter vital sign is evaluated to be invalid scan data, scan data for an electrocardiogram (ECG) vital sign is evaluated to be invalid scan data, or scan data for a temperature vital sign is outside an expected range.

18. The method of claim 2, further comprising:
determining that the measure of quality of the scan for the plurality of vital signs during a period of time is unreliable with minor motion; and
wherein the user feedback is generated to inquire if a user is pressing the scanner too lightly and instruct the user to press the portable vital signs scanner tighter against the user's body.

19. The method of claim 2, further comprising:
determining that the measure of quality of the scan for the plurality of vital signs during a period of time is unreliable without motion; and
wherein the user feedback is generated to inquire if a user is pressing the scanner too tightly and instruct the user to press the scanner with less force against the user's body.

20. The method of claim 2, further comprising:
determining that the measure of quality of the scan for the plurality of vital signs during a period of time is reliable with motion; and
wherein the user feedback is generated to instruct a user to hold still for a reliable scan.

21. The method of claim 2, further comprising:
determining that the measure of quality of the scan for the plurality of vital signs transitions between levels of quality from reliable to unreliable or unreliable to invalid; and
the user feedback is generated to instruct a user that the portable vital signs scanner is losing reliable contact.

22. The method of claim 2, wherein
determining that the measure of quality of the scan for the plurality of vital signs transitions between levels of quality from invalid to unreliable or unreliable to reliable; and
the user feedback is generated to instruct a user that the portable vital signs scanner is making better contact.

23. The method of claim 2, further comprising:
determining that the measure of quality of the scan for the plurality of vital signs transitions between from reliable with motion to reliable without motion; and
the user feedback is generated to instruct a user that he/she has done a great job reaching the reliable scan state.

24. The method of claim 23, wherein
determining that the measure of quality of the scan for the plurality of vital signs transitions between from a still super state to a minor motion super state; and
the user feedback is generated to instruct a user to please hold still.

25. The method of claim 2, further comprising:
determining that the measure of quality of the scan for the plurality of vital signs transitions between from a still super state to a big motion state or from a minor motion super state to the big motion state; and
the user feedback is generated to inquire of a user if he/she is shaking the portable vital signs scanner.

26. The method of claim 1, wherein
the concurrent scanning for the plurality of vital signs with the portable vital signs scanner generates a plurality of data samples of each vital sign; and the determining of the measure of quality of the scanning for the plurality of vital signs includes
  detecting an envelope curve of amplitude from the plurality of data samples for each vital sign.

27. The method of claim 26, wherein
the detecting of the movement of the portable vital signs scanner includes
  detecting acceleration of the portable vital signs scanner to obtain a plurality of data samples associated with movement of the portable vital signs scanner, and
  detecting an envelope curve of amplitude from the plurality of data samples associated with the movement of the portable vital signs scanner.

28. The method of claim 27, wherein
the detecting of the movement of the portable vital signs scanner further includes
  determining a level of movement of the portable vital signs scanner.

29. The method of claim 28, wherein
the level of movement of the portable vital signs scanner is big motion if the detected acceleration is greater than or equal to one-tenth of gravitational force.

30. The method of claim 28, wherein
the level of movement of the portable vital signs scanner is minor motion if the detected acceleration is greater than or equal to two hundredths of gravitational force and less than one-tenth of gravitational force.

31. The method of claim 30, wherein
the level of movement of the portable vital signs scanner is no motion or absence of motion if the detected acceleration is less than two hundredths of gravitational force.

32. The method of claim 26, wherein
the determining of the measure of quality of the scanning for at least one vital sign includes
  comparing an amplitude of a data sample of the at least one vital sign with a first threshold level to determine an invalid scan data quality.

33. The method of claim 32, wherein
the determining of the measure of quality of the scanning for at least one vital sign further includes
  comparing the amplitude of the data sample of the at least one vital sign with a second threshold level to discriminate between an unreliable scan data quality and a reliable scan data quality for the at least one vital sign.

34. The method of claim 26, wherein
the at least one vital sign is body temperature, and
the normal average body temperature taken at a forehead of an adult is ninety-seven and seven-tenths degrees Fahrenheit (97.7 F) with an expected range of plus and minus twelve degrees Fahrenheit (12 F) such that the expected temperature range is between one-hundred nine and seven-tenths degrees Fahrenheit (109.7 F) and eighty-five and seven-tenths degrees Fahrenheit (85.7 F).

* * * * *